(12) United States Patent
Gangoiti Munecas et al.

(10) Patent No.: US 11,149,258 B2
(45) Date of Patent: Oct. 19, 2021

(54) BRANCHED ALPHA GLUCANS

(71) Applicant: SOCIETE DES PRODUITS NESTLE S.A., Vevey (CH)

(72) Inventors: Joana Gangoiti Munecas, AG Groningen (NL); Sander Sebastiaan Van Leeuwen, AG Groningen (NL); Tjaard Pijning, AG Groningen (NL); Lubbert Dijkhuizen, AG Groningen (NL); Christina Vafeiadi, Lausanne (CH); Stephane Duboux, St-Prex (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/494,014

(22) PCT Filed: Mar. 13, 2018

(86) PCT No.: PCT/EP2018/056188
§ 371 (c)(1),
(2) Date: Sep. 13, 2019

(87) PCT Pub. No.: WO2018/167032
PCT Pub. Date: Sep. 20, 2018

(65) Prior Publication Data
US 2020/0123510 A1    Apr. 23, 2020

(30) Foreign Application Priority Data
Mar. 15, 2017    (EP) .................................... 17161087

(51) Int. Cl.
*C12P 19/04*    (2006.01)
*C12P 19/18*    (2006.01)
*C12N 9/10*    (2006.01)

(52) U.S. Cl.
CPC ............ *C12N 9/1051* (2013.01); *C12P 19/04* (2013.01); *C12P 19/18* (2013.01)

(58) Field of Classification Search
None
See application file for complete search history.

(56) References Cited

FOREIGN PATENT DOCUMENTS

| WO | 0190311 | 11/2001 |
| WO | 0190372 | 11/2001 |
| WO | 03008618 | 1/2003 |
| WO | 2010128859 | 11/2010 |

OTHER PUBLICATIONS

Meng et al. "Structure-function relationships of family GH70 glucansucrase and 4,6-alpha-glucanotransferase enzymes, and their evolutionary relationships with family GH13 enzymes" Cellular and Molecular Life Sciences, 2016, vol. 73, pp. 2681-2706.

Leemhuis et al. "Isomalto/Malto-Polysaccharide, A Novel Soluble Dietary Fiber Made Via Enzymatic Conversion of Starch" Journal of Agricultural and Food Chemistry, 2014, vol. 62, pp. 12034-12044.

*Primary Examiner* — Rebecca E Prouty
(74) *Attorney, Agent, or Firm* — K&L Gates LLP

(57) ABSTRACT

The present invention relates to the field of poly- and oligosaccharides and their dietary effects. In particular it relates to a method of producing a branched α-glucan. Further aspects of the invention are a branched α-glucan comprising linear segments of (α1→4) linked D-glucose units interspersed with (α1→6) glucosidic linkages and having (α1∴4,6) branching points; a food composition; and the use of an α-glucanotransferase enzyme for reducing the digestible carbohydrates of a starch containing food material.

5 Claims, 14 Drawing Sheets
Specification includes a Sequence Listing.

Fig. 1

| Bacterial strain | NCBI accession numbers | Motif II | | Motif III | | Motif IV | | Motif I | |
|---|---|---|---|---|---|---|---|---|---|
| | | | 1029 | | 1065 | | 1137 1140 | | 1 2 |
| | | | 3 4 | | 5 | | 6 7 | | 1 |
| a | | | | | | | | | |
| Lactobacillus reuteri CNCM I-2452 | KY595751 (SEQ ID NO:1) | 638 | GFRIDAADHID | 675 | HLSYNEGYRSS | 746 | YVTNHDSR-ANLING | 1097 | VDIVMNQ |
| Lactobacillus reuteri CNCM I-2451 | KY595750 (≡ SEQ ID NO:1) | 638 | GFRIDAADHID | 675 | HLSYNEGYRSS | 746 | YVTNHDSR-ANLING | 1097 | VDIVMNQ |
| Lactobacillus delbrueckii CNCM I-5166 | KY595720 (SEQ ID NO:5) | 670 | GFRIDAADHID | 707 | HLSYNEGYRSG | 778 | YVTNHDQR-ANLING | 1129 | VDIVMNQ |
| Streptococcus thermophilus CNCM I-5168 | KY595775 (SEQ ID NO:4) | 1031 | GFRIDATDHID | 1068 | HLSYNEQYSRG | 1140 | FVTNHDQR-NNLING | 1494 | ADIVLNH |
| Streptococcus thermophilus CNCM I-5167 | KY595777 (≡ SEQ ID NO:4) | 1031 | GFRIDATDHID | 1068 | HLSYNEQYSRG | 1140 | FVTNHDQR-NNLING | 1494 | ADIVLNH |
| b | | | | | | | | | |
| Lactobacillus reuteri 121 (GtfB) | AAU08014.2 (SEQ ID NO:6) | 1011 | GFRVDAADNID | 1048 | HLSYNEGYHSG | 1120 | FVTNHDQR-KNLINR | 1478 | EDIVMNQ |
| Lactobacillus reuteri ML1 (ML4) | AAU08003.2 (SEQ ID NO:7) | 1012 | GFRVDAADNID | 1049 | HLSYNEGYHSG | 1121 | FVTNHDQR-KNLINR | 1479 | EDIVMNQ |
| Lactobacillus reuteri DSM 20016 (GtfW) | ABQ83597.1 (SEQ ID NO:8) | 748 | GFRVDAADNID | 785 | HLVYNEGYHSG | 858 | FVTNHDQR-KNVINQ | 1215 | EDLVMNQ |
| Lactobacillus fermentum NCC 2970 | AOR73699 (SEQ ID NO:9) | 983 | GFRIDAADDMD | 1020 | HLSYNEGYCPG | 1092 | YVTNHDIR-NNLING | 1446 | EDIVMNQ |
| c | | | | | | | | | |
| Exiguobacterium sibiricum 255-15 | ACB62096.1 (SEQ ID NO:10) | 403 | GFRIDAASHYD | 433 | HLSYIESYKSE | 504 | FVNNHDQE-KNRVNQ | 138 | MDLVPNQ |
| Azotobacter chroococcum NCIMB 8003 | AJE22990.1 (SEQ ID NO:11) | 467 | GFRIDAASHIN | 500 | HLSYIESYVTQ | 567 | FVNNHDQE-HNILVT | 202 | VDVVPNQ |
| Paenibacillus beijingensis DSM 24997 | WP045672861.1 (SEQ ID NO:12) | 405 | GFRIDAASHYN | 437 | HLSYIESYTDN | 507 | FVMNHDQE-HNGIKG | 145 | VDLVPNQ |
| d | | | | | | | | | |
| Lactobacillus reuteri 180 (Gtf180) | AAU08001.1 (SEQ ID NO:13) | 1021 | GIRVDAVDNVD | 1058 | HINILEDWGWD | 1131 | FVRAHDSNAQDQIRQ | 1503 | ADWVPDQ |
| Lactobacillus reuteri 121 (GtfA) | AAU08015.1 (SEQ ID NO:14) | 1020 | SVRVDAPDNID | 1056 | HINILEDWNHA | 1128 | FVRAHDNNSQDQIQN | 1508 | ADWVPDQ |
| Streptococcus mutans SI (GtfSI) | BAA26114.1 (SEQ ID NO:15) | 473 | SIRVDAVDNVD | 510 | HLSILEAWSYN | 583 | FIRAHDSEVQDLIRD | 954 | ADWVPDQ |
| Leuconostoc mesenteroides NRRL-1355 | CAB65910.2 (SEQ ID NO:16) | 631 | GIRVDAVDNVD | 668 | HLSILEDWNGK | 762 | FVRAHDYDAQDPIRK | 1168 | ADWVPDQ |
| Leuconostoc citreum NRRL B-1299 | CDX66820.1 (SEQ ID NO:17) | 2206 | SIRIDAVDFIH | 2243 | HISLVEAGLDA | 2317 | IIHAHDKGVQEKVGA | 2688 | ADVVDNQ |
| Leuconostoc citreum NRRL B-742 | CDX65123.1 (SEQ ID NO:18) | 667 | SMRIDAISFVD | 704 | HISIVEAPKGE | 783 | IVHAHDKDIQDTVIH | 1182 | ADFVANQ |

US 11,149,258 B2

BRANCHED ALPHA GLUCANS

CROSS REFERENCE TO RELATED APPLICATIONS

The present application is a National Stage of International Application No. PCT/EP2018/056188, filed on Mar. 13, 2018, which claims priority to European Patent Application No. 17161087.6, filed on Mar. 15, 2017, the entire contents of which are being incorporated herein by reference.

FIELD OF THE INVENTION

The present invention relates to the field of poly- and oligosaccharides and their dietary effects. In particular it relates to a method of producing a branched α-glucan. Further aspects of the invention are a branched α-glucan comprising linear segments of (α1→4) linked D-glucose units interspersed with (α1→6) glucosidic linkages and having (α1→4,6) branching points; a food composition; and the use of an α-glucanotransferase enzyme for reducing the digestible carbohydrates of a starch containing food material.

BACKGROUND OF THE INVENTION

The prevalence of obesity and being overweight is rapidly increasing worldwide. The development of foods with high satiating capacities and low energy densities may help to prevent weight gain and to stimulate weight loss. Consumption of food and drinks containing non-digestible or slowly digestible carbohydrates instead of sugars induces a lower blood glucose rise after meals compared to sugar-containing food and drinks.

The most common carbohydrate in human diets is starch. This polysaccharide is produced by most green plants as an energy store. It is contained in large amounts in such staple foods as potatoes, wheat, maize, rice, and cassava. Various methods have been proposed for the chemical modification of starch and malto-oligosaccharides into non-digestible carbohydrates.

Lactic acid bacteria (LAB) are known to produce diverse extracellular polysaccharides (EPS) with applications in the food and health related industries. Examples are the α-glucans that are synthesized by the action of a single glucansucrase (GS) enzyme from sucrose. WO2001/90372 describes the formation of a branched α-glucan known as "reuteran", regarded as a health promoting food ingredient, synthesized by *Lactobacillus reuteri* 121 GtfA glucansucrase from sucrose. This enzyme is a member of the glycoside hydrolase family 70 (GH70).

It has been observed that highly branched α-glucans can combine a reduced digestibility with a thickening effect triggered by the low pH conditions of the stomach. This thickening leads to feelings of satiety, EP1545562.

EP2427565 describes the use of a GH70 glucanotransferase enzyme of *L. reuteri* 121 GtfB to convert starch into linear gluco-oligosaccharides containing relatively long iso-malto-oligosaccharide side chains. The *L. reuteri* 121 GtfB displays 4,6-α-glucanotransferase (4,6-α-GTase) activity as it cleaves (α1→4) linkages and forms new consecutive (α1→6) glucosidic linkages. Such materials are partially resistant to digestion and hence give less glucose production on consumption, contributing to the prevention of obesity and type II diabetes.

Co-pending application PCT/EP2016/071474 describes how the GH70 family GtfD enzymes *Azotobacter chroococcum* NCIMB 8003 and *Paenibacillus beijingensis* DSM 24997 convert amylose, and starch into α-glucans with alternating (α1→4)/(α1→6) glucosidic linkages and (α1→4,6) branching points, resembling the reuteran polymer synthesized by the *L. reuteri* 121 GtfA GS from sucrose. Unusually for the starch-converting GH70 family enzymes, both these GtfD enzymes are unable to synthesize consecutive (α1→6) glucosidic linkages.

It would be desirable to provide further means for the enzymatic modification of starch, starch derivatives and malto-oligosaccharides in order to change their functional properties and improve their nutritional value. In particular it would be beneficial to provide enzymes to perform such modifications which are suitable for use in food manufacture and exhibit good enzyme activity and thermostability.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide an improved solution for the enzymatic modification of starch and other polysaccharide or oligosaccharide into materials having reduced digestibility, or at least to provide a useful alternative. The object of the present invention is achieved by the subject matter of the independent claims. The dependent claims further develop the idea of the present invention.

Accordingly, the present invention provides in a first aspect a method of producing an α-glucan with a ratio of branching of at least 8% comprising contacting a polysaccharide or oligosaccharide substrate comprising at its non-reducing end at least two (α1→4) linked D-glucose units with an α-glucanotransferase enzyme capable of cleaving (α1→4) glucosidic linkages and making new (α1→6) glucosidic linkages without forming consecutive (α1→6) glucosidic linkages, to form a glucose polymer having linear segments of (α1→4) linked D-glucose units interspersed with (α1→6) glucosidic linkages and having (α1→4,6) branching points, wherein said α-glucanotransferase (for example a GtfB type of enzyme) comprises an amino acid sequence having at least 70% identity to SEQ ID NO:1.

In a second aspect, the invention relates to an α-glucan comprising linear segments of (α1→4) linked D-glucose units interspersed with (α1→6) glucosidic linkages and having (α1→4,6) branching points wherein the α-glucan has a ratio of branching of at least 8%; comprises less than 1 wt. % consecutive (α1→6) linkages; has an average molecular mass between $1 \times 10^3$ Da and $5 \times 10^4$ Da; and at least 85 wt. % of the α-glucan comprises (α1→4) linked D-glucose units having a degree of polymerisation from 2 to 7. A third aspect of the invention relates to a food composition comprising an α-glucan comprising linear segments of (α1→4) linked D-glucose units interspersed with (α1→6) glucosidic linkages and having (α1→4,6) branching points wherein the α-glucan has a ratio of branching of at least 8%; comprises less than 1 wt. % consecutive (α1→6) linkages; has an average molecular mass between $1 \times 10^3$ Da and $5 \times 10^4$ Da;

and at least 85 wt. % of the α-glucan comprises (α1→4) linked D-glucose units having a degree of polymerisation from 2 to 7.

A further aspect of the invention is the use of an α-glucanotransferase enzyme (for example a GtfB enzyme) that comprises an amino acid sequence having at least 70% identity to SEQ ID NO:1, or has an amino acid sequence of SEQ ID NO:1, for reducing the digestible carbohydrates of a starch containing food material. Still further aspects of the invention are a bacteria comprising a nucleic acid sequence having at least 95% identity to SEQ ID NO:1, a bacteria selected from the group consisting of *Lactobacillus reuteri* strains CNCM I-2451 (NCC 2603) and CNCM I-2452 (NCC 2613), an α-glucanotransferase enzyme comprising an amino acid sequence having at least 90% identity to SEQ ID NO:1, and an expression vector comprising a nucleic acid sequence encoding a polypeptide possessing at least 90% sequence identity to SEQ ID NO:1.

The inventors have identified novel GH70 family proteins in the genome of *L. reuteri* CNCM I-2451 (NCC 2603) and *L. reuteri* CNCM I-2452 (NCC 2613). These enzymes are very similar to each other and are designated GtfB. The GtfB GH70 subfamily mostly comprises 4,6-α-glucanotransferases synthesizing consecutive (α1→6) linkages, but surprisingly the activity of these novel enzymes resembles that of the GtfD 4,6-α-glucanotransferases identified in non-lactic acid bacterial strains. Studies of the *L. reuteri* CNCM I-2452 GtfB enzyme acting on amylose show that it is unable to synthesize consecutive (α1→6) glucosidic bonds, and instead synthesizes a low-molecular-mass reuteran-like polymer consisting of linear (α1→4) sequences connected by alternating linear (α1→4)/(α1→6) linkages and (α1→4, 6) branching points.

The more open architecture of the *L. reuteri* CNCM I-2452 GtfB active site may explain its ability to synthesize branched products, whereas the *L. reuteri* 121 GtfB 4,6-α-GTase, due to a tunnel extending beyond its active site, only forms linear products. Based on in vitro digestibility studies, branched types of polymers, especially highly branched with relative small size of branches, are less and/or more slowly digested by human gastrointestinal tract enzymes, opening new perspectives for the application of these enzymes for the reduction of glycemic index of starchy products [PCT/EP2016/071474]. *L. reuteri* bacteria have a long history of safe use in food, providing an advantage for their use by the food industry. The *L. reuteri* CNCM I-2452 GtfB, and its homolog encoded by *L. reuteri* strain NCC 2603 represent new evolutionary intermediates between GH13 and GH70 families. The *L. reuteri* CNCM I-2452 GtfB enzyme provides a valuable biocatalyst for the conversion of starch present in food into carbohydrates with attenuated blood glucose release.

1D $^1$H NMR analysis of the branched α-glucan formed by the *L. reuteri* CNCM I-2452 GtfB enzyme revealed the formation of (α1→4) and (α1→6) linkages. Methylation analysis of the α-glucan revealed the presence of terminal, 4-substituted, 6-substituted, and 4,6-disubstituted glucopyranose residues. The presence of 6-substituted, and 4,6-disubstituted glucopyranose residues means that the GtfB enzyme forms (α1→6) linkages in linear and branched orientations, respectively. No evidence was observed for two consecutive (α1→6)-linked glucopyranose residues by 2D NMR spectroscopy analysis. Also, the branched α-glucan synthesized by the *L. reuteri* CNCM I-2452 GtfB enzyme was resistant to the endo-(α1→6)-hydrolase activity of dextranase, further confirming the absence of consecutive (α1→6) linkages in this polysaccharide. Thus, all the branched residues are (α1→4,6)-α-D-Glcp-(α1→4)-residues. Also, all 6-substituted glucopyranose residues detected by methylation analysis must be (α1→4)-linked and are connecting (α1→4) glucan chains forming alternating (α1→6)/(α1→4) linkages in the linear part of the α-glucan structure. This is in contrast to the action of branching enzymes with E.C. 2.4.1.18 activity disclosed in EP1943908. Such branching enzymes only create (α1→4,6) branching points but do not create (α1→6) linkages in the linear part of the α-glucan structure, and so do not form linear segments of (α1→4) linked D-glucose units interspersed with (α1→6) glucosidic linkages (sometimes referred to as "alternating" (α1→4) and (α1→6) glucosidic linkages).

DESCRIPTION OF THE DRAWINGS

FIG. 1 is a table showing the sequence alignment of conserved motifs I-IV in the catalytic domain of novel GtfB-like proteins identified in the NCC genome database and other GH70 starch and sucrose acting enzymes: (A) GtfB-like enzymes showing differences in some of the residues in motifs II and IV forming the substrate-binding site, (B) Characterized GtfB-like enzymes, (C) GtfC-like and GtfD-like 4,6-α-GTase enzymes, (D) sucrose-active GSs enzymes. The seven conserved amino acid residues in GH70 enzymes (indicated by the numbers 1 to 7 above the sequences) are also conserved in the *L. reuteri* CNCM I-2452, *L. reuteri* CNCM I-2451 and *L. delbrueckii* CNCM I-5166 GtfB proteins identified in the NCC genome database, while six of these seven amino acid residues are conserved for *S. thermophilus* CNCM I-5168 and *S. thermophilus* CNCM I-5167. Amino acids that constitute the catalytic triad are in bold and slightly shaded. The "hotspots" 1029, 1065, 1137 and 1140 (*L. reuteri* Gtf180 GS numbering) are outlined with boxes. Symbols: NU, nucleophile; A/B, general acid/base; TS, transition state stabilizer.

DETAILED DESCRIPTION OF THE INVENTION

Figure 2A:
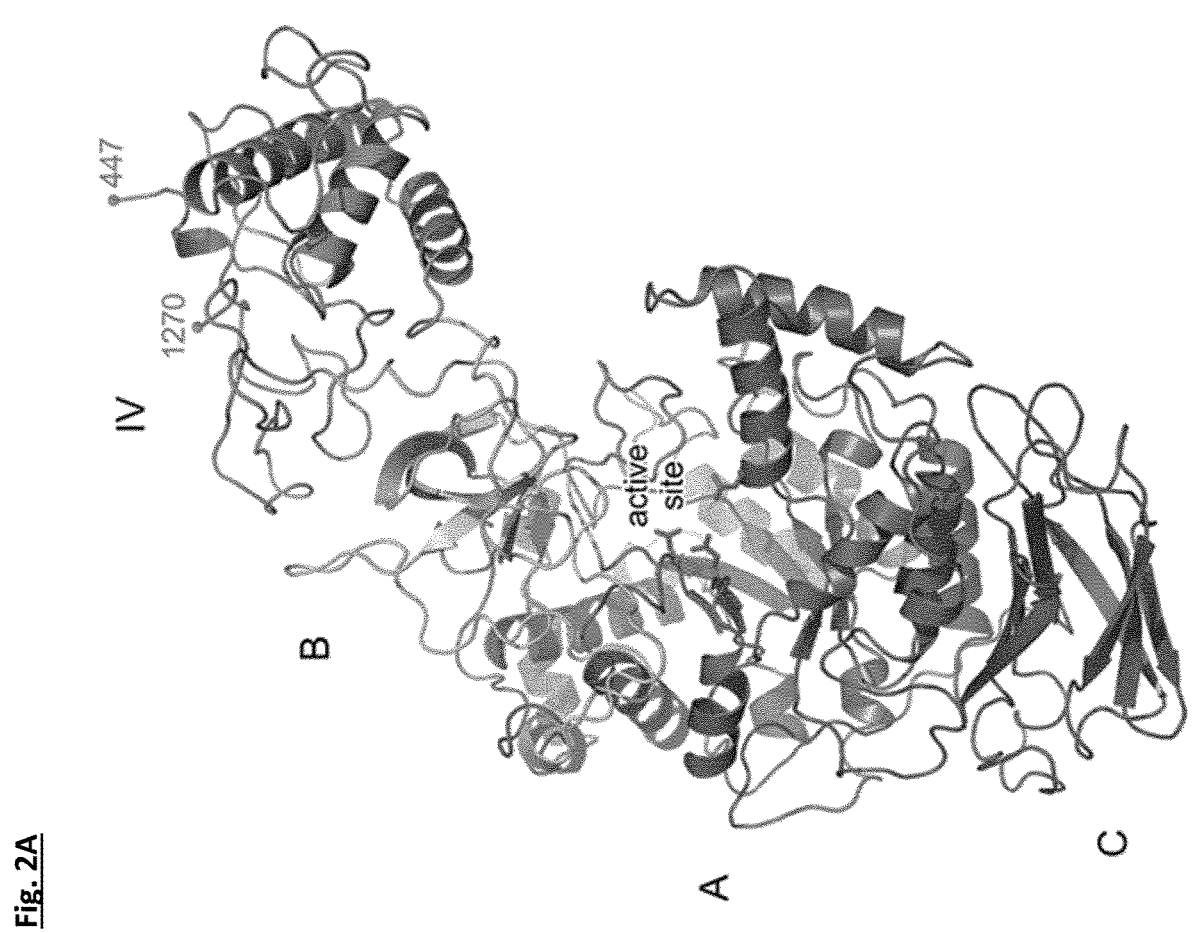
FIG. 2 shows a homology model for *L. reuteri* CNCM I-2452 (also named *L. reuteri* NCC 2613) GH70 enzyme. Tertiary structure prediction was accomplished by using the Phyre2 server and the *L. reuteri* 121 GtfB-ΔNΔV as template. (A) Overall 3D model structure of *L. reuteri* CNCM I-2452 GH70 enzyme. Domains A, B, C and IV are indicated; the proposed catalytic residues in the active site are shown in stick representation (B) Close-up of the active sites regions of the *L. reuteri* CNCM I-2452 GtfB enzyme and the *L. reuteri* 121 GtfB. with loops A1, A2 and B highlighted; the sequence alignment of these loops in the two enzymes is also shown. In *L. reuteri* CNCM I-2452 GtfB, the much shorter loops A1 and B predict a much more open substrate binding groove than observed in the *L. reuteri* 121 enzyme. (C) Superposition of the maltopentaose bound in subsites −1 to −5 of the *L. reuteri* 121 GtfB (PDB: 5JBF) with the *L. reuteri* CNCM I-2452 GtfB model. Residues near the binding groove are indicated.

Consequently the present invention relates in part to a method of producing an α-glucan with a ratio of branching of at least 8% comprising contacting a polysaccharide or oligosaccharide substrate comprising at its non-reducing end at least two (α1→4) linked D-glucose units with an α-glucanotransferase enzyme capable of cleaving (α1→4) glucosidic linkages and making new (α1→6) glucosidic linkages without forming consecutive (α1→6) glucosidic linkages, to form a glucose polymer having linear segments of (α1→4) linked D-glucose units interspersed with (α1→6) glucosidic linkages and having (α1→4,6) branching points, wherein said α-glucanotransferase comprises (for example consists of) an amino acid sequence having at least 70% identity to SEQ ID NO:1 (for example at least 75, 80, 85, 90, 95, 96, 97, 98, or 99% identity to SEQ ID NO:1). The α-glucanotransferase enzyme in the method of the invention may be capable of cleaving (α1→4) glucosidic linkages and transferring malto-oligosaccharides up to DP7 (for example up to DP5). The α-glucanotransferase enzyme in the method of the invention may be a GtfB type of enzyme. The α-glucanotransferase enzyme in the method of the invention may be a GtfB enzyme from a bacterium selected from the group consisting of *L. reuteri* CNCM I-2451, *L. reuteri* CNCM I-2452, *Streptococcus thermophilus* CNCM I-5167, *S. thermophilus* CNCM I-5168, *Lactobacillus delbrueckii* sbsp. *delbrueckii* CNCM I-5166.

SEQ ID NO:1 is the sequence of the *L. reuteri* CNCM I-2452 GtfB enzyme. SEQ ID NO:4 is the sequence of the *Streptococcus thermophilus* CNCM I-5168 GtfB enzyme (which is identical to the sequence of the *Streptococcus thermophilus* CNCM I-5167 GtfB enzyme). SEQ ID NO:5 is the sequence of the *Lactobacillus delbrueckii* sbsp. *delbrueckii* CNCM I-5166 enzyme. SEQ ID NO:19 is the sequence of the *L. reuteri* CNCM I-2451 GtfB enzyme.

*L. reuteri* CNCM I-2452, also named NCC 2613, was deposited with the Collection Nationale de Cultures de Microorganismes (CNCM), Institut Pasteur, 25 rue du Docteur Roux, F-75724 PARIS Cedex 15, France, on 19 Apr. 2000 and given the deposit number I-2452.

*L. reuteri* CNCM I-2451, also named NCC 2603, was deposited with the Collection Nationale de Cultures de Microorganismes (CNCM), Institut Pasteur, 25 rue du Docteur Roux, F-75724 PARIS Cedex 15, France, on 19 Apr. 2000 and given the deposit number I-2451.

*L. delbrueckii* sbsp. *delbrueckii* CNCM I-5166, also named NCC 828, was deposited with the Collection Nationale de Cultures de Microorganismes (CNCM), Institut Pasteur, 25 rue du Docteur Roux, F-75724 PARIS Cedex 15, France, on 14 Feb. 2017 and given the deposit number I-5166.

S. thermophilus CNCM I-5167, also named NCC 903, was deposited with the Collection Nationale de Cultures de Microorganismes (CNCM), Institut Pasteur, 25 rue du Docteur Roux, F-75724 PARIS Cedex 15, France, on 14 Feb. 2017 and given the deposit number I-5167.

S. thermophilus CNCM I-5168, also named NCC 2408, was deposited with the Collection Nationale de Cultures de Microorganismes (CNCM), Institut Pasteur, 25 rue du Docteur Roux, F-75724 PARIS Cedex 15, France, on 14 Feb. 2017 and given the deposit number I-5168.

Lactobacillus fermentum CNCM I-5068, also named NCC 2970 was deposited with the Collection Nationale de Cultures de Microorganismes (CNCM), Institut Pasteur, 25 rue du Docteur Roux, F-75724 PARIS Cedex 15, France, on 8 Mar. 2016 and given the deposit number I-5068.

Polysaccharides are polymeric carbohydrate molecules composed of long chains of monosaccharide units bound together by glycosidic linkages. Oligosaccharides are saccharide polymers containing a small number (typically three to nine) of monosaccharides. An example of a substrate comprising at its non-reducing end at least two ($\alpha 1 \rightarrow 4$) linked D-glucose units is amylose. In the present specification, the abbreviation Gtf refers to glucanotransferase. Single ($\alpha 1 \rightarrow 6$) glucosidic linkages between one or more ($\alpha 1 \rightarrow 4$) glucosidic linkages as may be formed in the method of the invention are sometimes referred to as "bridging" ($\alpha 1 \rightarrow 6$) linkages. The notation ($\alpha 1 \rightarrow 4$) may be used instead of $\alpha(1 \rightarrow 4)$ to refer to a $1 \rightarrow 4$ $\alpha$ linkage, but these are equivalent, as are ($\alpha 1 \rightarrow 6$) and $\alpha(1 \rightarrow 6)$.

In the context of the present invention, the ratio of branching is defined as the total number of branching anhydroglucose units (AGU), i.e. AGU being bound to three other units, with respect to the total number of AGU of a molecule. The ratio of branching can be determined by methods known in the art, such as methylation with gas chromatography. The $\alpha$-glucan produced by the method of the invention may have a ratio of branching of at least 8%, for example at least 10%, for example at least 15%.

An embodiment of the present invention provides a method of producing an $\alpha$-glucan with a ratio of branching of at least 8% comprising contacting a polysaccharide or oligosaccharide substrate comprising at its non-reducing end at least two ($\alpha 1 \rightarrow 4$) linked D-glucose units with a L. reuteri GtfB enzyme comprising (for example consisting of) an amino acid sequence having at least 90% identity to SEQ ID NO:1 (for example at least 95, 96, 97, 98, or 99% identity to SEQ ID NO:1).

GH70 enzymes active on starch possess a Tyr residue, replacing the 1065 (L. reuteri 180 Gtf180 numbering) residue of motif III which is well-conserved in GSs.

The GtfB protein sequences of L. reuteri CNCM I-2451, L. reuteri CNCM I-2452, S. thermophilus CNCM I-5167, S. thermophilus CNCM I-5168 and L. delbrueckii sbsp. delbrueckii CNCM I-5166 show differences in some of the residues in motifs II and IV forming the substrate-binding site. Similarly to GtfC and GtfD enzymes, the subsite +1 Asn residue (N1029 in L. reuteri Gtf180 GS) is replaced by His in these five GtfB proteins. The correspondence between the L. reuteri Gtf180 GS numbering and numbering in other enzyme sequences for the residues in motifs 1 to IV is shown in FIG. 1. For example, residue 1029 according to L. reuteri Gtf180 GS numbering is residue 683 in the GtfB of L. reuteri CNCM I-2451, residue 646 in the GtfB of L. reuteri CNCM I-2452, residue 1039 in the GtfB of S. thermophilus CNCM I-5167, residue 1039 in the GtfB of S. thermophilus CNCM I-5168 and residue 678 in the GtfB of L. delbrueckii sbsp. delbrueckii CNCM I-5166. For the GtfB proteins of L. reuteri CNCM I-2451 and L. reuteri CNCM I-2452 the amino acids at positions 1137 and 1140 following the putative transition state stabilizer (Gtf180 L. reuteri 180 numbering), are Ser and Ala, instead of the Gln and Lys residues typically found in most GtfB- and GtfC-like 4,6-$\alpha$-GTases. For the GtfB proteins of L. delbrueckii sbsp. delbrueckii CNCM I-5166 the amino acid at position 1140 following the putative transition state stabilizer (Gtf180 L. reuteri 180 numbering) is also Ala.

An embodiment of the present invention provides a method of producing an $\alpha$-glucan with a ratio of branching of at least 8% comprising contacting a polysaccharide or oligosaccharide substrate comprising at its non-reducing end at least two ($\alpha 1 \rightarrow 4$) linked D-glucose units with a GtfB enzyme comprising an amino acid sequence with histidine at residue 1029 and/or serine at residue 1137 and/or alanine at reside 1140, following Gtf180 Lactobacillus reuteri 180 numbering. The GtfB enzyme according to the method of the invention may comprise an amino acid sequence with a tyrosine residue at position 1065 and a histidine residue at position 1029 (Gtf180 L. reuteri 180 numbering). The GtfB enzyme according to the method of the invention may comprise an amino acid sequence with a tyrosine residue at position 1065, a histidine residue at position 1029 and an alanine residue at position 1140 (Gtf180 L. reuteri 180 numbering). The GtfB enzyme according to the method of the invention may comprise an amino acid sequence with a tyrosine residue at position 1065, a histidine residue at position 1029 and/or a serine residue at position 1137 and/or an alanine residue at position 1140, following Gtf180 Lactobacillus reuteri 180 numbering. The invention may provide a method of producing an $\alpha$-glucan with a ratio of branching of at least 8% comprising contacting a polysaccharide or oligosaccharide substrate comprising at its non-reducing end at least two ($\alpha 1 \rightarrow 4$) linked D-glucose units with an $\alpha$-glucan otransferase enzyme capable of cleaving ($\alpha 1 \rightarrow 4$) glucosidic linkages and making new ($\alpha 1 \rightarrow 6$) glucosidic linkages without forming consecutive ($\alpha 1 \rightarrow 6$) glucosidic linkages, to form a glucose polymer having linear segments of ($\alpha 1 \rightarrow 4$) linked D-glucose units interspersed with ($\alpha 1 \rightarrow 6$) glucosidic linkages and having ($\alpha 1 \rightarrow 4,6$) branching points, wherein said $\alpha$-glucanotransferase is a GtfB type of enzyme comprising an amino acid sequence with a histidine residue at position 1029 and/or a serine residue at position 1137 and/or an alanine reside at position 1140, following Gtf180 Lactobacillus reuteri 180 numbering.

The substrate in the method of the invention may have a degree of polymerization of at least four, for example it may comprise at least four D-glucose units. The degree of polymerization is the number of monomeric units in a polymer or oligomer molecule. For example, the substrate in the method of the invention may have a degree of polymerization of at least five, for example it may comprise at least five D-glucose units. The substrate in the method of the invention may be selected from the group consisting of starch (for example waxy starch or high amylose starch), starch derivatives, malto-oligosaccharides, amylose, amylopectin, maltodextrins, ($\alpha 1 \rightarrow 4$) glucans and combinations thereof. Starch derivatives are prepared by physically, enzymatically, or chemically treating native starch to change its properties.

The substrate in the method of the invention may be comprised within another material, for example the substrate may be starch provided in the form of flour. It is advantageous to be able to convert polysaccharides or oligosaccharides comprised within food ingredients into α-glucans with lower digestibility, for example branched α-glucans. Such a conversion may increase the fibre content of the ingredients and/or may aid in reducing the calorie content of the ingredients. The method of the invention may be performed as part of a food processing operation, for example the α-glucanotransferase enzyme may be applied to food ingredients during a process to produce a food product. The substrate may be comprised within a material which already has a positive nutritional profile, for example the substrate may be comprised within wholegrain flour.

The extent to which the polysaccharide or oligosaccharide substrate may be converted by the α-glucanotransferase enzyme in the method of the invention can be adjusted by limiting the time of reaction. Partially converted substrates will provide different physical properties. The production of α-glucan in the method of the invention may be stopped before the reaction between the substrate and the α-glucanotransferase enzyme has reached completion, for example it may be stopped by denaturing (e.g. by heat) or removing the enzyme.

The α-glucanotransferase enzyme in the method of the invention may be immobilized, for example immobilized before contacting the polysaccharide or oligosaccharide substrate. Such immobilization techniques are well known in the art. Removal of the enzyme (discussed above) may be facilitated by immobilization of the enzyme. Immobilization techniques may be selected from the group consisting of covalent binding, entrapment, physical adsorption, cross-linking and combinations of these. In immobilization by covalent binding, enzymes are covalently linked to a support through the functional groups in the enzymes that are not essential for the catalytic activity. Oxide materials such as alumina, silica, and silicated alumina can be used for covalent binding of the enzyme. In immobilization by entrapment the enzyme is localized within the lattice of a polymer matrix or membrane. Entrapment methods are classified into five major types: lattice, microcapsule, liposome, membrane, and reverse micelle. The enzyme is entrapped in the matrix of various synthetic or natural polymers. Alginate, a naturally occurring polysaccharide that forms gels by ionotropic gelation is one such immobilization matrix. Immobilization by physical adsorption is the simplest and the oldest method of immobilizing enzymes onto carriers. Immobilization by adsorption is based on the physical interactions between the enzymes and the carrier, such as hydrogen bonding, hydrophobic interactions, van der Waals force, and their combinations. Adsorption is generally less disruptive to the enzymes than chemical means of attachment. Immobilization by cross-linking utilizes bi- or multifunctional compounds, which serve as the reagent for intermolecular cross-linking of the enzymes. Cross-linking may be used in combination with other immobilization methods such as adsorption or entrapment.

The polysaccharide or oligosaccharide substrate may be contacted with an α-glucanotransferase enzyme in the method of the invention at a temperature of between 10° C. and 75° C. (for example between 20° C. and 70° C., for example between 30° C. and 65° C., for example between 35° C. and 45° C.) and a pH of between 4.0 and 9.0 (for example between 4.8 and 8.0, for example between 5.0 and 6.0). The *L. reuteri* CNCM I-2452 GtfB enzyme is active at high pH values which is useful for applications in alkali environments.

In a further embodiment the present invention pertains to an α-glucan comprising linear segments of (α1→4) linked D-glucose units interspersed with (α1→6) glucosidic linkages and having (α1→4,6) branching points wherein the α-glucan has a ratio of branching of at least 8% (for example at least 12%, for further example at least 15%); comprises less than 1 wt. % consecutive (α1→6) linkages; has an average molecular mass between $1 \times 10^3$ Da and $5 \times 10^4$ Da (for example, an average molecular mass between $2 \times 10^3$ Da and $2 \times 10^4$ Da, for example, an average molecular mass between $5 \times 10^3$ Da and $1 \times 10^4$ Da); and at least 85 wt. % (for example at least 90 wt. %, for further example at least 95 wt. %) of the α-glucan comprises (α1→4) linked D-glucose units having a degree of polymerisation from 2 to 7. The percentage of the α-glucan comprising (α1→4) linked D-glucose units having a degree of polymerisation from 2 to 7 may for example be measured by digestion of the α-glucan with pullulanase and evaluating the resulting mixture with TLC and/or HPAEC.

The α-glucan according to the invention may comprise between 55 and 65 percent consecutive (α1→4) glucosidic linkages, between 8 and 15 percent single (α1→6) glucosidic linkages interspersed between linear (α1→4) linked D-glucose units and between 10 and 20 percent (α1→4,6) branching points, for example between 14 and 18 percent (α1→4,6) branching points. The α-glucan according to the invention may have less than 1% consecutive (α1→6) glucosidic linkages, for example it may have less than 0.5% consecutive (α1→6) glucosidic linkages, for further example it may have no consecutive (α1→6) glucosidic linkages. The α-glucan of the invention is similar to the low molecular mass α-glucan synthesized by the *P. beijingensis* GtfD from starch (co-pending application PCT/EP2016/071474), but has almost no (α1→4) linked D-glucose units having a degree of polymerisation greater than 7. This is beneficial as an increase in shorter chain fractions has been linked to a reduced digestion rate in starches [Xingfeng Li et al., Food Chemistry, 164, 502-509 (2014)].

In a further aspect, the invention provides an α-glucan obtainable (for example obtained) by contacting a polysaccharide or oligosaccharide substrate comprising at its non-reducing end at least two (α1→4) linked D-glucose units with an α-glucanotransferase enzyme comprising an amino acid sequence having at least 90% identity to SEQ ID NO:1, for example the *L. reuteri* CNCM I-2451 GtfB enzyme or the *L. reuteri* CNCM I-2452 GtfB enzyme.

The α-glucan of the invention can be regarded as a dietary fiber. Due to its highly branched structure, the α-glucan will resist enzymatic degradation in the upper gastrointestinal tract and end up in the large intestine where it can be fully fermented by the colonic microflora. In addition, such dietary fibres enhance satiety in humans or animals. Blood sugar levels rise after a meal. As the α-glucans of the invention display reduced digestibility compared to materials such as starch, meals prepared containing them will cause a reduced blood glucose response compared to the equivalent meal with starch, and will provoke a lower insulin response. A composition comprising the α-glucan of the invention may be for use in the control of postprandial blood glucose and insulin levels in a subject. The subject may be a human or a pet. A composition comprising the α-glucan of the invention may be for use in the treatment or prevention of a disorder linked to an increase in postprandial blood glucose and insulin levels in a subject. The disorder may be selected from the group consisting of diabetes, for example gestational diabetes; impairment of glucose metabolism; hyperinsulinemia or insulin resistance. The subject may be a diabetic or pre-diabetic human or pet.

Typically, postprandial hyper-insulinemia may promote the development of insulin resistance, metabolic syndrome, glucose intolerance and type-2 diabetes [Kopp W., Metabolism. 2003, July; 52(7):840-844]. Lowering the insulin demand after a meal however, can reduce on one hand the deterioration of the glycemic control in type-2 diabetes and on the other hand reduce the risk of developing type-2 diabetes in predisposed subjects.

A "pre-diabetic patient" is a subject showing insulin resistance or impaired glucose metabolism and is predisposed, for example by family history, lifestyle or genetics, for developing diabetes later in life. Reducing insulin secretion reduces the risk of the pancreas becoming exhausted in the long term, and so is beneficial for management of the pancreas in pre-diabetes or patients with metabolic disorders.

The use of a composition comprising the α-glucan of the invention would consequently reduce the risk and/or the development of diabetes, impaired glucose metabolism, hyperinsulinemia or insulin resistance in those subjects.

Prevalence of diabetes, insulin resistance or glucose intolerance is mostly observed in adult humans. However, more and more children are affected, or predisposed or at risk of developing such a disorder later in life. Hence, advantageously, prevention and/or treatment of those disorders is started already in young age. Alternatively, and similarly as observed with humans; diabetes, hyperinsulinemia or insulin resistance are more and more widespread among animals, particularly with animals kept as pet animals. Hence, the invention also pertains to cats and dogs.

A composition comprising the α-glucan of the invention may be for non-therapeutic use to decrease plasma postprandial glucose and insulin levels. It is advantageous that a composition comprising the α-glucan of the invention can also be administered to subjects, for example healthy subjects, which may be at risk of developing diabetes type-2, insulin resistance or glucose intolerance at some later time. A composition comprising the α-glucan of the invention, as disclosed herein, provides a reduced insulin level after consumption. Many healthy people desire to lose weight. Consuming meals which contain dietary fibre can increase satiety and therefore help people consume fewer digestible calories. A composition comprising the α-glucan of the invention may be for non-therapeutic use to lose weight.

Another aspect of the invention relates to a food composition comprising the α-glucan of the invention. The food composition may for example comprise between 1 and 20 wt. % of the α-glucan of the invention. The food composition may be a beverage, for example a powdered beverage mix or a beverage creamer; a potato product, for example instant mashed potato; a breakfast cereal, for example extruded cereal or porridge; a pet food product; a baked dough product, for example a bread, a pizza or a filled savoury turnover; or a confectionery product. The confectionery product may be a frozen confectionery product such as an ice-cream; a baked confectionery product such as a biscuit, for example a filled biscuit or wafer; a chocolate confectionery product; or a sugar-style confectionery product such as a gum, a jelly, a hard-boiled sweet or a chewy sweet. The term "sugar-style confectionery product" or "sugar-style candy" refers to confectionery products which would traditionally have been based on sugar, but may be manufactured with alternative sweeteners and/or sugar substitutes.

In a further embodiment, the invention provides for the use of an α-glucanotransferase enzyme for reducing the digestible carbohydrates of a food material, for example a starch-based food material, wherein the α-glucanotransferase enzyme comprises (for example consists of) an amino acid sequence having at least 85% identity to SEQ ID NO:1 (for example at least 90, 95, 96, 97, 98, or 99% identity to SEQ ID NO:1), or has an amino acid sequence of SEQ ID NO:1. In the scope of the current invention, digestible carbohydrates correspond to the fraction of the total carbohydrates that is digestible and available to provide energy to body cells.

The invention further provides for the use of a GtfB α-glucanotransferase enzyme for reducing the digestible carbohydrates of a food material, for example a starch-based food material, wherein the α-glucanotransferase GtfB enzyme comprises an amino acid sequence with histidine at residue 1029 and/or serine at residue 1137 and/or alanine at reside 1140 following Gtf180 *Lactobacillus reuteri* 180 numbering. The invention further provides for the use of a GtfB α-glucanotransferase enzyme for reducing the digestible carbohydrates of a food material, for example a starch-based food material, wherein the α-glucanotransferase GtfB enzyme is from a bacterium selected from the group consisting of *L. reuteri* CNCM I-2451, *L. reuteri* CNCM I-2452, *S. thermophilus* CNCM I-5167, *S. thermophilus* CNCM I-5168 and *L. delbrueckii* sbsp. *delbrueckii* CNCM I-5166, for example *L. reuteri* CNCM I-2452.

In an embodiment, the invention provides for the use of an α-glucanotransferase enzyme for reducing the glycemic index of a food material, for example a starch-based food material, wherein the α-glucanotransferase enzyme comprises (for example consists of) an amino acid sequence having at least 85% identity to SEQ ID NO:1 (for example at least 90, 95, 96, 97, 98, or 99% identity to SEQ ID NO:1), or has an amino acid sequence of SEQ ID NO:1. The glycemic index is a number associated with a particular type of food that indicates the food's effect on a person's blood glucose (also called blood sugar) level. A value of 100 represents the standard, an equivalent amount of pure glucose.

The invention further provides for the use of a GtfB α-glucanotransferase enzyme for reducing the glycemic index of a food material, for example a starch-based food material, wherein the α-glucanotransferase GtfB enzyme comprises an amino acid sequence with histidine at residue 1029 and/or serine at residue 1137 and/or alanine at reside 1140 following Gtf180 *Lactobacillus reuteri* 180 numbering.

One aspect of the invention provides a bacteria comprising a nucleic acid sequence having at least 95% identity to SEQ ID NO:1 (for example at least 96, 97, 98, or 99% identity to SEQ ID NO:1), for example a *Lactobacillus reuteri* bacteria. In another aspect, the invention provides a bacteria comprising a nucleic acid sequence having at least 95% identity to SEQ ID NO:4 (for example at least 96, 97, 98, or 99% identity to SEQ ID NO:4) for example *S. thermophilus* CNCM I-5167 or *S. thermophilus* CNCM I-5168 bacteria. In another aspect, the invention provides a bacteria comprising a nucleic acid sequence having at least 95% identity to SEQ ID NO:5 (for example at least 96, 97, 98, or 99% identity to SEQ ID NO:5), for example a *Lactobacillus delbrueckii* subsp. *delbrueckii* bacteria CNCM I-5166. An aspect of the invention is a bacteria selected from the group consisting of *L. reuteri* CNCM I-2451, *L. reuteri* CNCM I-2452, *S. thermophilus* CNCM I-5167, *S. thermophilus* CNCM I-5168 and *L. delbrueckii* sbsp. *delbrueckii* CNCM I-5166. For example a bacteria selected from the group consisting of *S. thermophilus* CNCM I-5167, *S. thermophilus* CNCM I-5168 and *L. delbrueckii* sbsp. *delbrueckii* CNCM I-5166.

A further aspect of the invention is an α-glucanotransferase enzyme comprising (for example comprising) an amino acid sequence having at least 95% identity to SEQ ID NO:1 (for example at least 96, 97, 98, or 99% identity to SEQ ID NO:1). A further aspect of the invention is an α-glucanotransferase enzyme comprising (for example comprising) an amino acid sequence having at least 95% identity to SEQ ID NO:4 (for example at least 96, 97, 98, or 99% identity to SEQ ID NO:4). A further aspect of the invention is an α-glucanotransferase enzyme comprising (for example comprising) an amino acid sequence having at least 95% identity to SEQ ID NO:5 (for example at least 96, 97, 98, or 99% identity to SEQ ID NO:5). The α-glucanotransferase enzyme may be for example a GtfB enzyme. A still further aspect of the invention is an expression vector comprising a nucleic acid sequence encoding a polypeptide possessing at least 95% sequence identity to SEQ ID NO:1 (for example at least 96, 97, 98, or 99% identity to SEQ ID NO:1). Another aspect of the invention is an expression vector comprising a nucleic acid sequence encoding a polypeptide possessing at least 95% sequence identity to SEQ ID NO:4 (for example at least 96, 97, 98, or 99% identity to SEQ ID NO:4). Another aspect of the invention is an expression vector comprising a nucleic acid sequence encoding a polypeptide possessing at least 95% sequence identity to SEQ ID NO:5 (for example at least 96, 97, 98, or 99% identity to SEQ ID NO:5).

EXPERIMENTAL

Materials and Methods

Annotation of the GH70 family enzymes present in the NCC genome database was performed using the dbCAN database for automated Carbohydrate-active enzyme Annotation [Y. Yin et al., dbCAN: a web resource for automated carbohydrate-active enzyme annotation Nucleic Acids Res. 40 (2012) W445-51.] Hits having an E-Value below 1E-5 and a bit score above 350 were considered. As a result 788 protein sequences were retrieved and used together with the *L. reuteri* 121 GtfB (Accession number: AAU08014.2), *Leuconostoc citreum* NRRL B-1299 branching sucrase (Accession number: CDX66820.1) and *L. reuteri* 180 Gtf180 GS (accession number: AAU08001.1) protein sequences for the construction of multiple sequence alignments with Jalview 2 desktop application using the MUSCLE algorithm [A. M. Waterhouse et al., Jalview Version 2—a multiple sequence alignment editor and analysis workbench, Bioinformatics 25 (2009) 1189-1191.] Sequences were only considered to be putative starch-acting GH70 enzymes if they possessed an aromatic Tyr (Y1055 *L. reuteri* 121 GtfB numbering) replacing the conserved Trp typically present in GSs, resulting in a set of 106 GtfB-like gene products. Branching sucrases were distinguished by the presence of a Gly residue at this position in the alignments. For further analysis, the set of GtfB proteins identified within the NCC genome database was expanded with characterized GH70 proteins indexed in CAZy (http://www.cazy.org/) and aligned by MUSCLE, using default parameters. Phylogenetic relationships were determined by the Maximum Likelihood method based on the JTT matrix model using MEGA6 [K. Tamura, G. Stecher, D. Peterson, A. Filipski, S. Kumar, MEGA6: Molecular Evolutionary Genetics Analysis version 6.0, Mol. Biol. Evol. 30 (2013) 2725-2729.] The analysis involved 167 amino acid sequences. Partial deletion of the positions containing alignment gaps and missing data was conducted. Statistical confidence of the inferred phylogenetic relationships was assessed by performing 1,000 bootstrap replicates.

Analysis of the *L. reuteri* CNCM I-2452 GtfB Protein Sequence

Multiple amino acid sequence alignments were generated with Clustal Omega (http://www.ebi.ac.uk/Tools/msa/clustalo/) and visualized by using the Jalview 2 desktop application. Subcellular localization of the *L. reuteri* GtfB protein was predicted using CELLO v.2.5: subCELlular LOcalization predictor (http://cello.life.nctu.edu.tw/) and its theoretical $M_w$ (molecular weight) was predicted by ExPASy Compute pI/$M_w$ (http://web.expasy.org/compute_pi/).

Structural Modelling of the *L. reuteri* CNCM I-2452 GtfB Protein

A three-dimensional model of the *L. reuteri* CNCM I-2452 GtfB was constructed with Phyre [Kelley et al., Nat. Protoc. 10 (2015) 845-858] using the recently determined three-dimensional structure of *L. reuteri* 121 GtfB 4,6-α-GTase (PDB entry: 5JBD); [Bai et al., Structure 25 (2016) 231-242] as a template for one-to-one threading of the full-length sequence, with default settings. For comparison of binding sites, also the crystal structures of *L. reuteri* 121 GtfB 4,6-α-GTase complexed with maltopentaose or isomalto-maltopentasaccharide (PDB entries: 5JBE, 5JBF) were used.

Cloning of the *L. reuteri* gtfB Gene

The gtfB gene fragment encoding for an N-terminally truncated variant of the GtfB protein (GtfB-ΔN) was amplified from *L. reuteri* CNCM I-2452 genomic DNA with Phusion DNA polymerase (Finnzyme, Helsinki, Finland) and cloned into a modified pET15b vector by ligation-independent cloning (LIC) [D. Bonsor et al., Org. Biomol. Chem. 4 (2006) 1252-1260]. The primers used contained LIC-compatible extensions (underlined), and were: Forward CAGGGACCCGGTGGGCATTTACTTGGAAATC and Reverse CGAGGAGAAGCCCGGTTAATCGTCTTCAATATTAGC. The KpnI-digested vector and the generated PCR product were purified from gel, and subsequently treated with T4 DNA polymerase in the presence of dATP and dTTP, respectively. The two reaction products were mixed together in a 1:4 molar ratio, and the mixture was used to transform chemical-competent *Escherichia coli* DH5a cells (Phabagen), yielding pET15b/gtfB-ΔN. This vector encodes the GtfB-ΔN (amino acids 417 to 1281) fused with an N-terminal His6-tag cleavable by a 3C protease. The constructed expression vector pET15b/gtfB-ΔN was verified by nucleotide sequencing (GATC, Cologne, Germany), and transformed into *E. coli* BL21 Star (DE3).

Expression and Purification of the *L. reuteri* CNCM I-2452 GtfB Protein

Fresh Luria Broth medium supplemented with ampicillin (100 μg ml$^{-1}$) was inoculated with 1% (v/v$^{-1}$) of an overnight culture of *E. coli* BL21 Star (DE3) harboring the pET15b/gtfB-4N plasmid, and cultivated at 37° C. and 160 rpm. Protein expression was induced at an OD600 of 0.7 by adding isopropyl-β-d-1-thiogalactopyranoside to 0.1 mM, and cultivation was continued for 20 h at 16° C. Cells were harvested by centrifugation (10,000×g, 20 min). The GtfB-ΔN enzyme was purified by Ni$^{2+}$-nitrilotriacetic acid (NTA) affinity chromatography (Sigma Aldrich, St. Louis, USA) as described previously [Gangoiti et al., Biochim Biophys Acta 1860 (2016) 1224-1236]. Purity was assessed by SDS-PAGE analysis, and protein concentrations were determined by measuring the absorbance at 280 nm, using a NanoDrop 2000 spectrophotometer (Isogen Life Science, De Meern, The Netherlands).

Enzyme Activity Assays

The initial total activity of the *L. reuteri* CNCM I-2452 GtfB-ΔN enzyme was determined by the amylose-iodine staining method using 0.125% (w v$^{-1}$) amylose V (AVEBE, Foxhol, The Netherlands) as described before [19, 29]. Routinely, enzymatic assays were performed with 2 µg ml$^{-1}$ of enzyme in 25 mM sodium acetate (pH 5.5) and 1 mM CaCl$_2$. The decrease in absorbance of the α-glucan-iodine complex resulting from transglycosylation and/or hydrolytic activity was monitored at 660 nm for 8 min at 40° C. One unit of activity was defined as the amount of enzyme converting 1 mg of substrate per min. The pH profile and optimum pH were determined at 40° C. by varying the pH between 3.0 and 10.0. Sodium citrate buffer (25 mM) was used at pH 3.0-7.0, sodium phosphate buffer (25 mM) at pH 7.0-8.0, Tris-HCl (25 mM) at pH 8.0-9.0, and sodium bicarbonate (25 mM) at pH 9.0-10.0.

Substrate Specificity of the *L. reuteri* CNCM I-2452 GtfB Enzyme

The substrate specificity of the *L. reuteri* CNCM I-2452 GtfB enzyme was investigated by incubating 40 µg ml$^-$ of purified enzyme with either 25 mM sucrose (Acros), nigerose (Sigma-Aldrich), panose (Sigma-Aldrich), isomaltose (Sigma-Aldrich), isomaltotriose (Sigma-Aldrich), isomaltopentaose (Carbosynth), malto-oligosaccharides (MOS) with degrees of polymerization (DP) 2-7 (Sigma-Aldrich), or with 0.6% (w v$^{-1}$) amylose V (AVEBE, Foxhol, The Netherlands), potato starch (Sigma-Aldrich) or amylopectin (Sigma-Aldrich). Potato starch was pregelatinized by autoclaving (15 min, 120° C.). Amylose V (1%, w/v) was prepared as a stock solution in sodium hydroxide (1 M). Prior to use, the stock solution was neutralized with 7 M HCl and diluted to a concentration of 0.85% (w v'). Incubations were carried out in 25 mM sodium acetate buffer, pH 5.5 with 1 mM CaCl$_2$ at 37° C. for 24 h. Reactions were stopped by heating the samples to 100° C. for 8 min. The progress of the reactions was analysed by thin-layer chromatography (TLC) and/or high-performance-anion-exchange chromatography (HPAEC).

Thin Layer Chromatography and High Performance Anion Exchange Chromatography with Pulsed Amperometric Detection Analysis Carbohydrate samples were spotted in 1-cm lines on a TLC silica gel 60F254 sheet (Merck, Darmstadt, Germany). The TLC plate was run for 6 h in butanol:acetic acid:water (2:1:1, v v$^{-1}$), and products were visualized with orcinol/sulfuric acid staining. A mixture of glucose and malto-oligosaccharides (DP2 to DP7) was used as standard.

HPAEC-PAD analysis was performed using an ICS3000 workstation (Thermo Scientific, Amsterdam, The Netherlands), equipped with a CarboPac PA-1 column (Thermo Scientific; 250×2 mm) and an ICS3000 electrochemical detection module. Prior to analysis the carbohydrate samples were diluted 1:300 in DMSO and the oligosaccharides were separated at a 0.25 ml min$^{-1}$ flow rate by using a sodium acetate gradient (10 to 240 mM) in 100 mM NaOH over 57 min. The injection volume of each sample was 5 µl. The identity of the peaks was determined using commercial oligosaccharide standards and a mixture of MOS of DPs from 2 to 30.

HPSEC Analysis

Molecular mass distribution of the product mixtures was determined using a size exclusion chromatography system (Agilent Technologies 1260 Infinity) equipped with a multi angle laser light scattering detector (SLD 7000 PSS, Mainz), a viscometer (ETA-2010 PSS, Mainz) and a differential refractive index detector (G1362A 1260 RID Agilent Technologies), as described before [20, 29]. Briefly, samples were dissolved at a concentration of 4 mg ml$^{-1}$ in DMSO-LiBr (0.05 M) and separation was carried out by using three PFG-SEC columns with porosities of 100, 300 and 4000 Å, coupled with a PFG guard column. The eluent was DMSO-LiBr (0.05 M) at a flow rate of 0.5 ml min$^{-1}$. The system was calibrated and validated using a standard pullulan kit (PSS, Mainz, Germany) with $M_w$ ranging from 342 to 805 000 Da. The specific RI increment value (dn/dc) was also measured by PSS and was 0.072 ml g$^{-1}$ (private communication with PSS). The multiangle laser light scattering signal was used to determine the molecular masses of amylose V and the high molecular mass (HMM) polysaccharides generated by the *A. chroococcum* and *P. beijingensis* GtfD enzymes. The dn/dc values for these polysaccharides were taken to be the same as for pullulan. The molecular masses of the *L. reuteri* CNCM I-2452 GtfB, *L. reuteri* 121 GtfB and *P. beijingensis* GtfD low molecular mass (LMM) polymers were determined by universal calibration method. Measurements were performed in duplicate.

Production, Isolation and Structural Analysis of the Products from Amylose V Incubation with *L. reuteri* CNCM I-2452 GtfB Incubations of amylose V (0.6% w v$^{-1}$) and GtfB-ΔN (0.2 mg) were performed under the conditions described in "Substrate specificity of the *L. reuteri* CNCM I-2452 GtfB". After incubation for 24 h at 37° C., the reaction was stopped by transfer to 100° C. for 10 min. The polysaccharide was separated from trace amounts of small oligosaccharides (DP<5) also present in the product mixture by size-exclusion chromatography on a Biogel P2 column (2.5×50 cm; Bio-Rad, Veenendaal, The Netherlands) using 10 mM NH$_4$HCO$_3$ as eluent at a flow rate of 48 ml h$^{-1}$.

NMR Spectroscopy

Resolution-enhanced 1D/2D $^1$H and $^{13}$C NMR spectra were recorded in D$_2$O on a Varian (nova-500 spectrometer (NMR center, University of Groningen, The Netherlands) at a probe temperature of 298 K. Samples were exchanged twice in D$_2$O (99.9 at % D, Cambridge Isotope Laboratories, Inc., Andover, Mass.) with intermediate lyophilization, and then dissolved in 0.6 ml of $D_2O$. One-dimensional 500-MHz $^1H$ NMR spectra were recorded at a 4000 Hz spectral width and 16 k complex points, using a WET1D pulse to suppress the HOD signal. Two-dimensional $^1H$-$^1H$ spectra (COSY, TOCSY MLEV17 30, 50, and 150 ms, and ROESY 300 ms) were recorded with 4000 Hz spectral width, collecting 200 increments. In case of TOCSY spectra 2000 complex data points were collected, for COSY and ROESY spectra 4000 complex data points were used. 2D $^{13}C$-$^1H$ NMR spectra were recorded in 128 increments of 2000 complex points with 4000 Hz spectral width in t2 and 10 000 Hz in t1. The data were processed using MestReNova 5.3 (Mestrelabs Research SL, Santiago de Compostella, Spain). Manual phase correction and Whittacker smoother baseline correction were applied to all spectra. Chemical shifts (δ) are expressed in ppm with reference to internal acetone (δ 2.225 for $^1H$ and δ 31.08 for $^{13}C$).

Methylation Analysis

Polysaccharide samples (~5 mg) were per-methylated using $CH_3I$ and solid NaOH in DMSO, as described before [S. S. van Leeuwen et al., Carbohydr. Res. 343 (2008) 1237-1250]. After hydrolysis with 2 M trifluoroacetic acid (2 h, 120° C.), the partially methylated monosaccharides generated were reduced with $NaBD_4$ (2 h, room temperature, aqueous solution), and the solution was neutralized with acetic acid. Subsequently, boric acid was removed by co-evaporation with methanol. The resulting partially methylated alditols were per-acetylated using pyridine:acetic anhydride (1:1 v/v) at 120° C. yielding mixtures of partially-methylated alditol acetates, which were analyzed by GLC-EI-MS as described.

Enzymatic Treatments with α-Amylase, Dextranase and Pullulanase

The α-glucan samples (5 mg) were dissolved in 500 µl of sodium acetate buffer (50 mM pH 5.0), and incubated separately with excess amounts of α-amylase (*Aspergillus oryzae*; Megazyme), dextranase (*Chaetomium erraticum*; Sigma-Aldrich), and pullulanase M1 (*Klebsiella planticola*; Megazyme) at 37° C. After 48 h, the degree of hydrolysis was evaluated by TLC and/or HPAEC. Starch, dextran and pullulan, were used as positive controls for the α-amylase, dextranase and pullulanase treatments, respectively, obtaining fully hydrolyzed products under these conditions.

Characterization of GtfB-Treated Wheat Flour: In Vitro Digestion

Samples of refined wheat flour were treated with different amounts of *L. reuteri* CNCM I-2452 GtfB enzyme and an in vitro method was used to evaluate digestibility.

| Enzyme | V(enzyme) [µl] | V(H2O) [ml] | V(CaCl$_2$ 50 mM) [µl] | Enzyme [µg per 100 mg Starch] |
|---|---|---|---|---|
| Reference | — | 16.283 | 333 | 667 |
| LrGtfB | 95 | 16.188 | 333 | 667 |
| LrGtfB (−) | 48 | 16.235 | 333 | 333.5 |
| LrGtfB (+) | 190 | 16.093 | 333 | 1334 |

Samples were prepared by adding 143 mg of pregelatinized refined wheat flour into a 50 ml falcon tubes and adding the required quantity of milli-Q $H_2O$ (see Table). Vortex mixing and stirring with a magnet was applied until homogenization (almost 30 min). 333 µl of 50 mM $CaCl_2$ solution was added. Tubes were equilibrated at 37° C. in an oven at 45 rpm on a roller mixer at 60 rpm. The required quantity of enzyme was added and allowed to incubate for 24 h. Enzymes were inactivated by putting the tubes in boiling water for 6 min. The solutions were freeze-dried Phosphate buffer solution (PBS) (10 mM) was prepared in a 1000 mL volumetric flask by dissolving 0.26 g of $KH_2PO_4$, 1.44 g $Na_2HPO_4*2H_2O$ and 8.71 g NaCl with 800 mL mQ $H_2O$. The pH was adjusted to 6.9 with HCl (1M) and brought to the mark with mQ $H_2O$.

For the preparation of 100 mg/mL enzyme, 1.5 g of pancreatin (P) (Sigma Aldrich) or rat intestinal powder (RIP) (Sigma Aldrich) was mixed with 15 mL PBS (10 mM) in a centrifugation tube. The solution was Vortexed and sonicated on ice for 7 min. The tubes were centrifuged at 10'000×g for 30 min at 4° C. The supernatant was transferred to a plastic bottle.

The sample and reference contained 1% (w/V) of total glucose in PBS-buffer and were stirred magnetically for 2 h before the start of the digestion. For each time (0, 15, 30, 60, 120 and 180 min), a set of 5 mL Eppendorf was prepared, one for the blank, one for the reference, and one for each sample. The blank contained PBS buffer only and the reference pregelatinized refined wheat flour, treated in the same way as the samples. For each time set, 300 µL ($V_{sample}$) of the required solution were added to the 5 mL Eppendorf tubes (PBS, reference or sample). Pancreatin and RIP solution were equilibrated at 37° C. for 5 min in a water bath and the 5 mL Eppendorf of the time set were equilibrated at 37° C. in a thermomixer. 200 U/mg of pancreatin ($V_p$) ($U_{required}$=600 U) and 100 U/mg ($U_{required}$=300 U) of RIP were added to each tube. One U corresponds to the amount of protein that releases 1 µmol of glucose per min. The tubes were mixed (1000 rpm) and incubated at 37° C., 450 rpm for the corresponding time (15, 30, 60, 120 and 180 min). After incubation, a 500 µL aliquot of the sample was added into 1.5 mL ethanol (EtOH) into 2 mL Eppendorf tubes were prepared before and stored at 4° C. The tubes were centrifuged for 10 min at 10'000×g. For time 0, the enzymes were replaced with 10 mM PBS and a 500 µL aliquot taken into 1.5 mL of EtOH and centrifuged under the same conditions as for the other points.

Free glucose was measured with the Wako glucose kit using glucose standards of 0, 0.125, 0.25, 0.5, 0.75, 1.0, 1.5 and 2.0 mg/ml. Total glucose release (total [G1]) is determined as in Equation 1 where a and b are the slope and intercept of the standard curve, $[G1]_{Blank}$ is the blank sample with PBS buffer only, and $F_{dil}$ is the dilution factor. Percentage of glucose release corresponds to the total glucose release divided by the mass of glucose in the sample ($M_{G1\,total}$) multiplied by 100, Equation.

$$\text{total}[G1]\left[\frac{mg}{ml}\right] = \left(\frac{\overline{Abs}_{sample} - b}{a} - [G1]_{Blank}\right) \cdot (V_{sample} + V(P) + V(R)) \cdot F_{dil} \quad \text{Equation 1}$$

$$G1\ release[\%] = \frac{\text{total}[G1]}{m_{G1\,total}} \cdot 100 \quad \text{Equation 2}$$

RESULTS AND DISCUSSION

Identification of Novel Starch Active GH70 Enzymes Within the NCC Genome Database The NCC genome database was screened for novel GtfB-like enzymes. Among the GtfB enzymes identified were *L. reuteri* CNCM I-2451, *L. reuteri* CNCM I-2452, *S. thermophilus* CNCM I-5167, *S. thermophilus* CNCM I-5168, *L. delbrueckii* sbsp. *delbrueckii* CNCM I-5166 and *L. fermentum* CNCM I-5068 (a 4,3-α-GTase described in co-pending application EP16172606.2). The conserved motifs I to IV of these GtfB proteins were analyzed in detail (FIG. 1). Motifs I to IV of the GtfB enzymes identified in the NCC displayed clear similarity with those corresponding to previously characterized 4,6-α-GTases, and were easily identified. The order of these conserved regions I to IV in the GtfB sequences is IV-I, reflecting their circularly permutated domain organization. Six residues, conserved among these GH70 motifs, including the catalytic residues (D1015, E1053, D1125; *L. reuteri* 121 GtfB numbering) and residues involved in the formation of subsite −1 (R1013, H1124, D1479 were found in all the identified GtfB protein sequences.

Regarding other functionally important positions in motifs III and IV, a unique sequence feature is the replacement of the W1065 (*L. reuteri* 180 Gtf180 numbering) residue of motif III forming a stacking interaction with the acceptor substrate in glucansucrases, by a tyrosine in the GtfB type of enzymes. Interestingly, a Tyr residue is also present in the *L. fermentum* CNCM I-5068 GtfB 4,3-α-GTase, and it is strictly conserved throughout the GtfC and GtfD subfamilies as well. Thus, in this study this "sequence fingerprint" was used as a criterion to select only those GH70 enzymes active on starch. Second, in motif IV, previously characterized GtfB 4,6-α-GTases have an invariant motif QRK downstream the transition state stabilizer (note that the alignment depicted in FIG. 1 predicts a one amino acid gap), whereas GSs and previously described GTFB 3,4 α-GTase show variations in this region. Previous mutational studies combined with structural data revealed that this region, and more specifically, residues 1137 and 1140 (first and fourth residue downstream the transition state stabilizer in *L. reuteri* 180 Gtf180 GS) contribute to glycosidic linkage specificity in GSs. In case of the reuteran-like polymer synthesizing GtfD 4,6-α-GTase enzymes, the Gln residue at position 1137 is also conserved, whereas the Lys residue at position 1140 is substituted by a His and has been proposed to define this novel product specificity. In contrast to these differences, GtfB 4,6-α-GTases and GSs share high conservation in the subsite +1 Asn residue in motif II (N1019 in *L. reuteri* GfB), differing from GtfC and GtfD enzymes that contain a His residue at this position. This subsite +1 Asn residue is critical for the activity and linkage specificity of the Gtf180 GSs.

Interestingly, the GtfB protein sequences of *L. reuteri* CNCM I-2451, *L. reuteri* CNCM I-2452, *S. thermophilus* CNCM I-5167, *S. thermophilus* CNCM I-5168 and *L. delbrueckii* sbsp. *delbrueckii* CNCM I-5166 show differences in some of the residues in motifs 11 and IV forming the substrate-binding site. Similarly to GtfC and GtfD enzymes, the subsite +1 Asn residue (N1029 in *L. reuteri* Gtf180 GS) is replaced by His in these five GtfB proteins. For the GtfB proteins of *L. reuteri* CNCM I-2451 and *L. reuteri* CNCM I-2452 the amino acids at positions 1137 and 1140 following the putative transition state stabilizer (Gtf180 *L. reuteri* 180 numbering), are Ser and Ala, instead of the Gln and Lys residues typically found in most GtfB- and GtfC-like 4,6-α-GTases. For the GtfB proteins of *L. delbrueckii* sbsp. *delbrueckii* CNCM I-5166 the amino acid at position 1140 following the putative transition state stabilizer (Gtf180 *L. reuteri* 180 numbering) is also Ala. It is noteworthy that the *L. fermentum* CNCM I-5068 GtfB, which shares high identity with *L. reuteri* 121 GtfB but displays 4,3-α-GTase activity, also contains unique variations in residues 1029, 1137 and 1140, providing support for these being "hot-spot" positions for product specificity in GtfB enzymes.

Amino Acid Sequence Analysis and Structure Modelling of the GtfB Enzyme of *L. reuteri* CNCM I-2452

*L. reuteri* CNCM I-2452 genome contains a single gene coding for a GH70 enzyme with a theoretical molecular mass of 145 kDa. As reported for other GH70 family proteins, the *L. reuteri* CNCM I-2452 GH70 enzyme is predicted to function as an extracellular protein. Alignment of its amino acid sequence with biochemically characterized GH70 enzymes shows highest sequence identity with the *L. fermentum* GtfB 4,3-α-GTase (83% identity). The characterized GtfB 4,6-α-GTase enzymes of *L. reuteri* 121, *Lactobacillus reuteri* ML1 and *Lactobacillus reuteri* DSM 20016 also share significant amino acid identity (76%, 75% and 66% identity) with the *L. reuteri* CNCM I-2452 GH70 enzyme, further indicating that this protein belongs to the GtfB subfamily of GH70 enzymes.

Figure 2B:
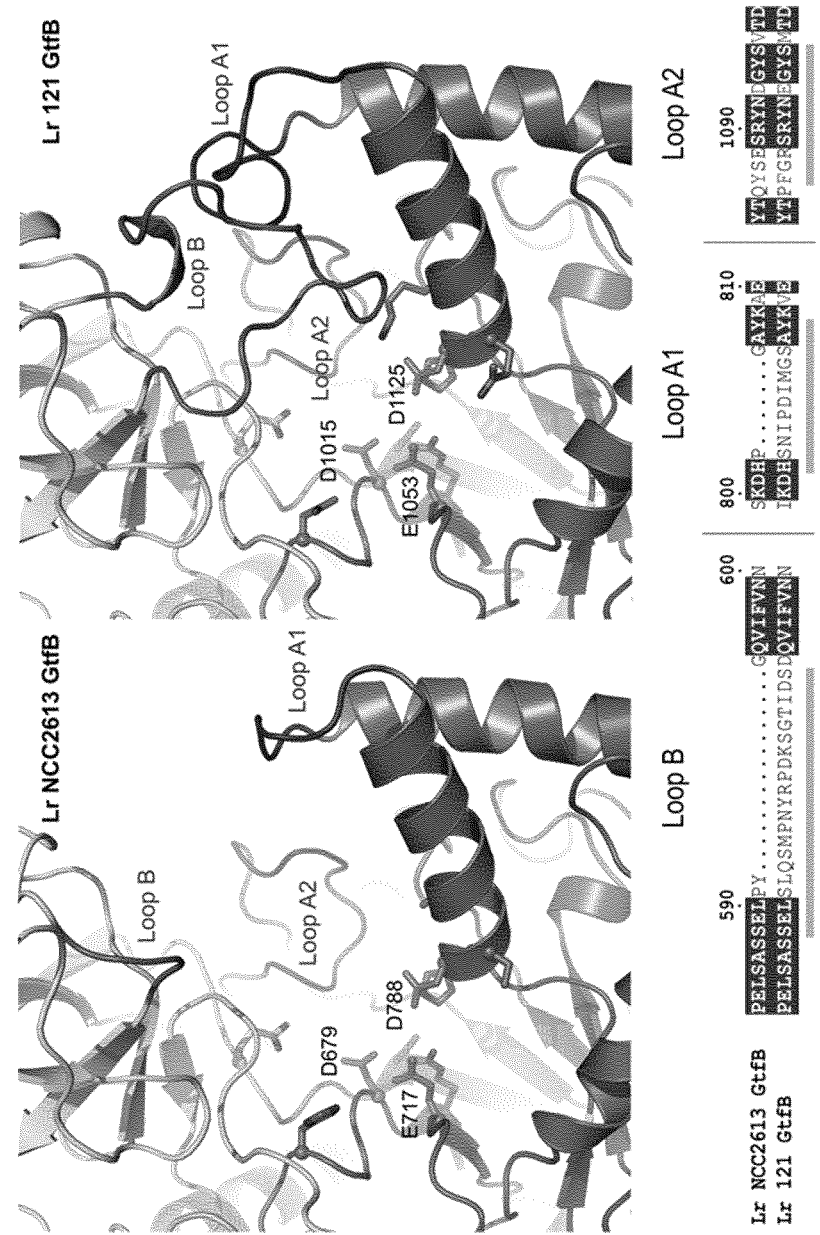
Figure 2C:
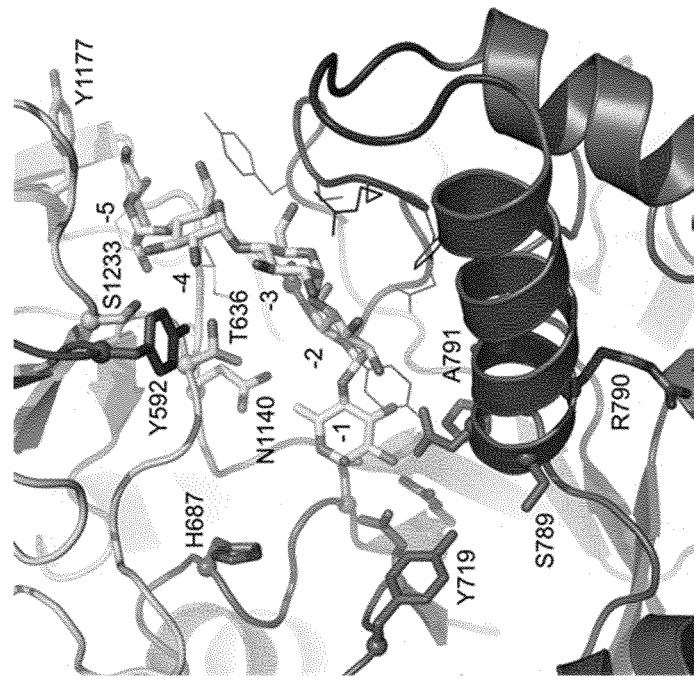

The obtained 3D model of *L. reuteri* CNCM I-2452 GH70 enzyme (FIG. 2), based on the *L. reuteri* 121 GtfB-ΔNΔV 4,6-α-GTase crystal structure [Bai et al., (2016)], comprises domains A, B, C and IV; it reflects the high sequence similarity between the two enzymes (79% identity for these domains). The same "U-fold" domain organization is observed, with a circularly permuted catalytic $(\beta/\alpha)_8$ barrel in domain A, characteristic of GSs and GtfB type of enzymes. Sequence comparison revealed that the *L. reuteri* CNCM I-2452 GH70 enzyme, like the *L. reuteri* 121 GtfB enzyme, also has an N-terminal variable domain (residues 1-446) and lacks a C-terminal variable domain. In its catalytic domain (A), the spatial arrangement of the catalytic residues in the active center is similar to that of *L. reuteri* 121 GtfB-ΔNΔV. On the other hand, notable structural differences were observed between the substrate binding sites of the two enzymes. Most importantly, whereas the *L. reuteri* 121 enzyme features a tunnel extending beyond the active site formed by the 13-residue loop A1 and the 20-residue loop B, the corresponding loops in the *L. reuteri* CNCM I-2452 GH70 enzyme are only 6 and 4 residues long (802-807 and 590-593, respectively; FIG. 2). As a consequence, these loops do not form a tunnel covering donor substrate binding subsites, rendering the binding groove fully accessible, like in α-amylases. Superposition with the maltopentaose-bound *L. reuteri* 121 GtfB-ΔNΔV structure shows that residues in the highly similar loop A2 of the *L. reuteri* CNCM I-2452 GH70 enzyme likely interact with bound substrates, and so may residue Y592 from loop B (FIG. 2). Also its tyrosine residue (Y1177, corresponding to Y1521 of the *L. reuteri* 121 GtfB enzyme) at subsite −6 is conserved (not shown) to provide an aromatic stacking interaction. Other notable differences are the presence of a histidine residue (H683) in motif 11 replacing the asparragine present in 4,6-α-GTases (N1019 in *L. reuteri* 121 GtfB), and the three residues following the transition state stabilizer in motif IV (SRA replacing QRK). On the other hand, its tyrosine residue near subsite +1 (Y719, motif 111)

is conserved with 4,6-α-GTases. Residues from these motifs are known to contribute to the product specificity of GH70 enzymes. These structural differences observed in the architecture of the active site of the 3D model of the *L. reuteri* CNCM I-2452 GH70 enzyme prompted us to study the reaction and product specificity of this enzyme.

Purification and Biochemical Properties of the *L. reuteri* CNCM I-2452 GH70 Enzyme Previous work showed that truncation of the N-terminal variable region of the *L. reuteri* 121 GtfB did not affect the enzyme catalytic properties, but facilitated protein expression [Y. Bai et al., Environ. Microbiol. 81 (2015) 7223-7232]. Thus, the *L. reuteri* CNCM I-2452 gene encoding a GtfB enzyme was cloned and expressed in *E. coli* (DE3) BL21 star without its N-terminal variable region (amino acids 417 to 1281). Under the conditions used, high protein expression levels were observed in the soluble fraction, and following His tag affinity purification a total of ~50 mg of pure protein per liter of culture was obtained. SDS-PAGE analysis revealed a single protein band with an apparent molecular weight of ~100 kDa, which fits the predicted molecular mass deduced from its amino acid sequence (98 kDa).

The purified *L. reuteri* CNCM I-2452 GH70 enzyme was inactive with sucrose but active with maltodextrins/starch, confirming its identity as a GtfB-ΔN enzyme. In order to determine the best conditions for subsequent reactions, the effects of pH on its enzyme activity were determined by using amylose V as substrate. This GtfB-ΔN enzyme showed its maximal activity at pH 5.5, but exhibited a broad pH tolerance, retaining more than 80% of this activity over a pH from 4 to 9. This pH profile significantly differs from those reported for other GtfB enzymes, which showed significantly lower activities at basic pH values. The specific total activity value of the purified *L. reuteri* CNCM I-2452 GtfB-ΔN on 0.125% (w $v^{-1}$) amylose in 25 mM citrate phosphate buffer, pH 5.5, containing 1 mM $CaCl_2$ at 40° C. was 24±0.6 U/mg. This value is similar to the one reported for the *L. fermentum* GtfB-ΔN 4,3-α-GTase (22 U/mg), but remarkably higher than that determined for the *L. reuteri* 121 GtfB 4,6-α-GTase, namely 2.8 U $mg^{-1}$ (at 40° C. and pH 5.5 and 5.0, respectively).

Substrate and Product Specificity of the *L. reuteri* CNCM I-2452 GtfB Enzyme

Figure 3:
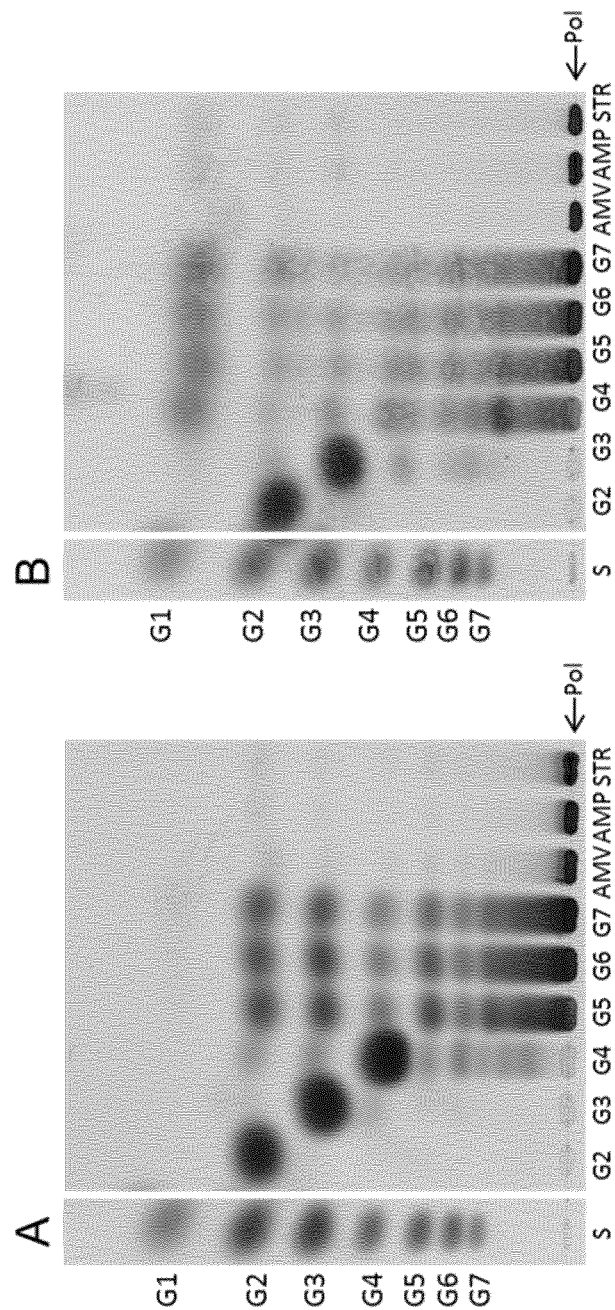
FIG. 3 shows a TLC analysis of the products produced by 40 μg ml$^{-1}$ of the *L. reuteri* CNCM I-2452 GtfB-ΔN (A) and *L. reuteri* 121 GtfB (B) 4,6-α-glucanotransferase enzymes from incubations with 25 mM malto-oligosaccharides (DP2-DP7), 0.6% (w v$^{-1}$) amylose V, 0.6% (w v$^{-1}$) amylopectin, and 0.6% (w v$^{-1}$) potato soluble starch. The reaction mixtures were incubated at 37° C. and pH 5.5 (*L. reuteri* CNCM I-2452 GtfB) or pH 5.0 (*L. reuteri* 121 GtfB) during 24 h. S, standard; G1, glucose; G2, maltose; G3, maltotriose; G4, maltotetraose; G5, maltopentaose; G6, maltohexaose; G7, maltoheptaose; AMV, amylose V; AMP, amylopectin; STR, potato soluble starch; Pol, polymer.

The *L. reuteri* CNCM I-2452 GtfB-ΔN was incubated with different carbohydrate substrates at 37° C. for 24 h, and its activity was compared with that of the *L. reuteri* 121 4,6-α-GTase Gtf B. As shown by TLC (FIG. 3), both GtfB enzymes displayed hydrolysis and transglycosylase (disproportionation) activity on MOS with DP4 to DP7, as revealed by the formation of a range of shorter and longer oligosaccharide products. Both enzymes also accumulated polymeric material from MOS. In the case of the *L. reuteri* CNCM I-2452 GtfB-ΔN, polymer accumulation was detected when using maltopentaose (DP5) and longer MOS substrates, whereas the *L. reuteri* 121 GtfB already formed polymer from maltotetraose (DP4). Note that for the *L. reuteri* 121 GtfB, glucose clearly accumulated from the different MOS substrates. Instead, the *L. reuteri* CNCM I-2452 GtfB-ΔN accumulates maltose and some low molecular mass oligosaccharides, but not glucose as a side product of its hydrolase/transglycosidase activity. This observation suggests that these two GtfB enzymes differ in their mode of action.

Incubation of amylose V, potato starch and amylopectin with the *L. reuteri* CNCM I-2452 GtfB-ΔN enzyme resulted in the appearance of some low molecular mass products that were not clearly detectable by TLC, but that were indicating that, similar to the *L. reuteri* 121 GtfB, this enzyme is also active on these polymeric substrates. The *L. reuteri* CNCM I-2452 GtfB enzyme was inactive on sucrose, panose, nigerose, pullulan, dextran and isomalto-oligosaccharides with DP2, DP3, and DP5 (data not shown).

Figure 4A:
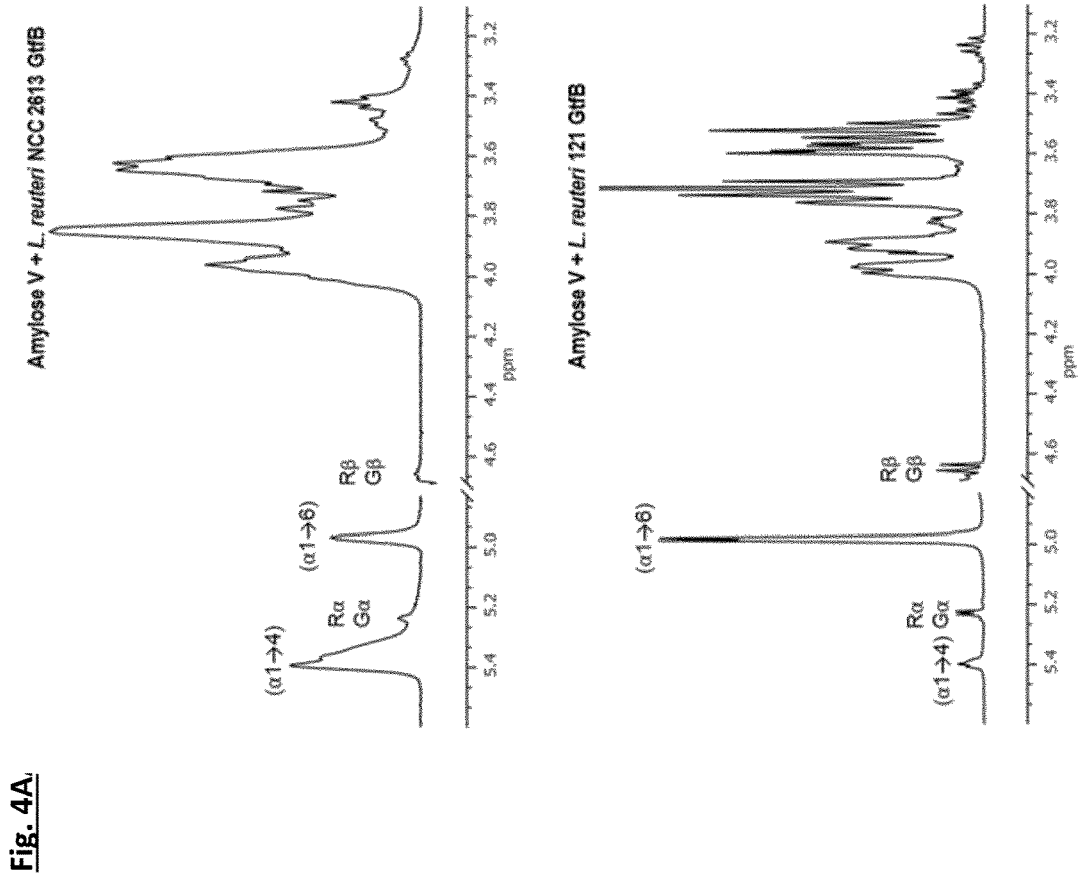
FIG. 4 shows the characterization of product mixtures formed by the incubation of 0.6% (w v$^{-1}$) amylose V with 40 µg ml$^{-1}$ of *L. reuteri* CNCM I-2452 GtfB-ΔN, *L. reuteri* 121 GtfB, and *P. beijingensis* GtfD for 24 h at 37° C. and pH 5.5 (*L. reuteri* CNCM I-2452 GtfB), pH 5.0 (*L. reuteri* 121 GtfB) and pH 7.0 (*P. beijingensis* GtfD). (A) $^1$H NMR spectrum (D$_2$O, 298K) of the generated products. The anomeric signals indicated as Gα/β and Rα/β correspond to free glucose and reducing -(1→4)-D-Glcp units, respectively. Chemical shifts are shown in parts per million (ppm) relative to the signal of internal acetone (δ 2.225). (B) HPSEC molecular mass distribution of the reaction products formed.

To study the product specificity of the *L. reuteri* CNCM I-2452 GtfB-ΔN in more detail, the products synthesized from amylose V were analysed by one-dimensional $^1H$ NMR spectroscopy. As shown in FIG. 4A, this $^1H$ NMR analysis revealed the presence of two broad anomeric signals indicative of (α1→4) linkages (δ ~5.40-5.35) and (α1→6) linkages (δ ~4.97); thus *L. reuteri* CNCM I-2452 GtfB-ΔN also acts as a 4,6-α-GTase. Small signals corresponding to free glucose units (Gα H-1, δ 5.225; Gβ H-1, δ 4.637) and 4-substituted reducing-end glucose residues (Rα H-1, δ 5.225; RβH-1, δ 4.652) were detected as well, indicating that trace amounts of glucose, maltose and other small oligosaccharides were also present in this product mixture. This $^1H$ NMR spectrum was highly similar to those of the reuteran-like polymers synthesized by the *A. chroococcum* GtfD and *P. beijingensis* GtfD, as indicated by the presence of extra signals strongly overlapping in the (α1→4) anomeric region (FIG. 4A). Note that these signals are not present in the NMR spectrum of the IMMP generated by *L. reuteri* 121 GtfB (FIG. 4A).

Figure 4B:
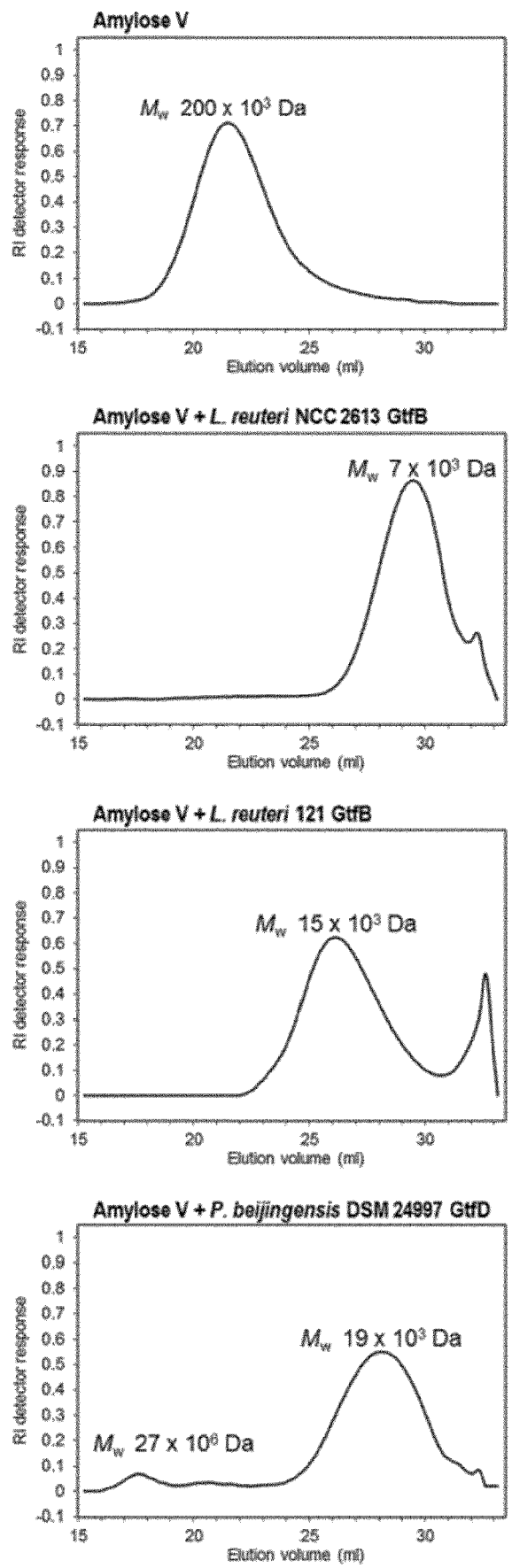

The amylose-derived products from *L. reuteri* CNCM I-2452 GtfB-ΔN were also analyzed by HPSEC with multidetection. The HPSEC profile of the original amylose V substrate consisted of a single peak eluting at ~21 ml with an average $M_w$ of 200×$10^3$ Da. As shown in FIG. 4B, the action of the *L. reuteri* CNCM I-2452 GtfB-ΔN on amylose V resulted in the formation of a peak at a higher elution volume (~29 ml) corresponding to a low molecular mass α-glucan with an average $M_w$ of 7×$10^3$ Da, together with a small shoulder peak corresponding to maltose. This HPSEC profile significantly differs from those reported for other 4,6-α-GTases [EP2427565, PCT/EP2016/071474] producing higher molecular mass polymers from amylose V. For example, the $M_w$ value of the α-glucan generated by *L. reuteri* CNCM I-2452 GtfB-ΔN is half that of the IMMP products of *L. reuteri* 121 GtfB (15×$10^3$ Da). On the other hand, it is much smaller than the HMM polysaccharide synthesized by the *A. chroococcum* GtfD, which had an average $M_w$ of 13×$10^6$ Da. The *L. reuteri* NCC2613 GtfB-ΔN product profile is also different from that of *P. beijingensis* GtfD which showed a bimodal polymer distribution containing both HMM (27×$10^6$ Da) and LMM (19×$10^3$ Da) polymers (FIG. 4B).

Figure 5:
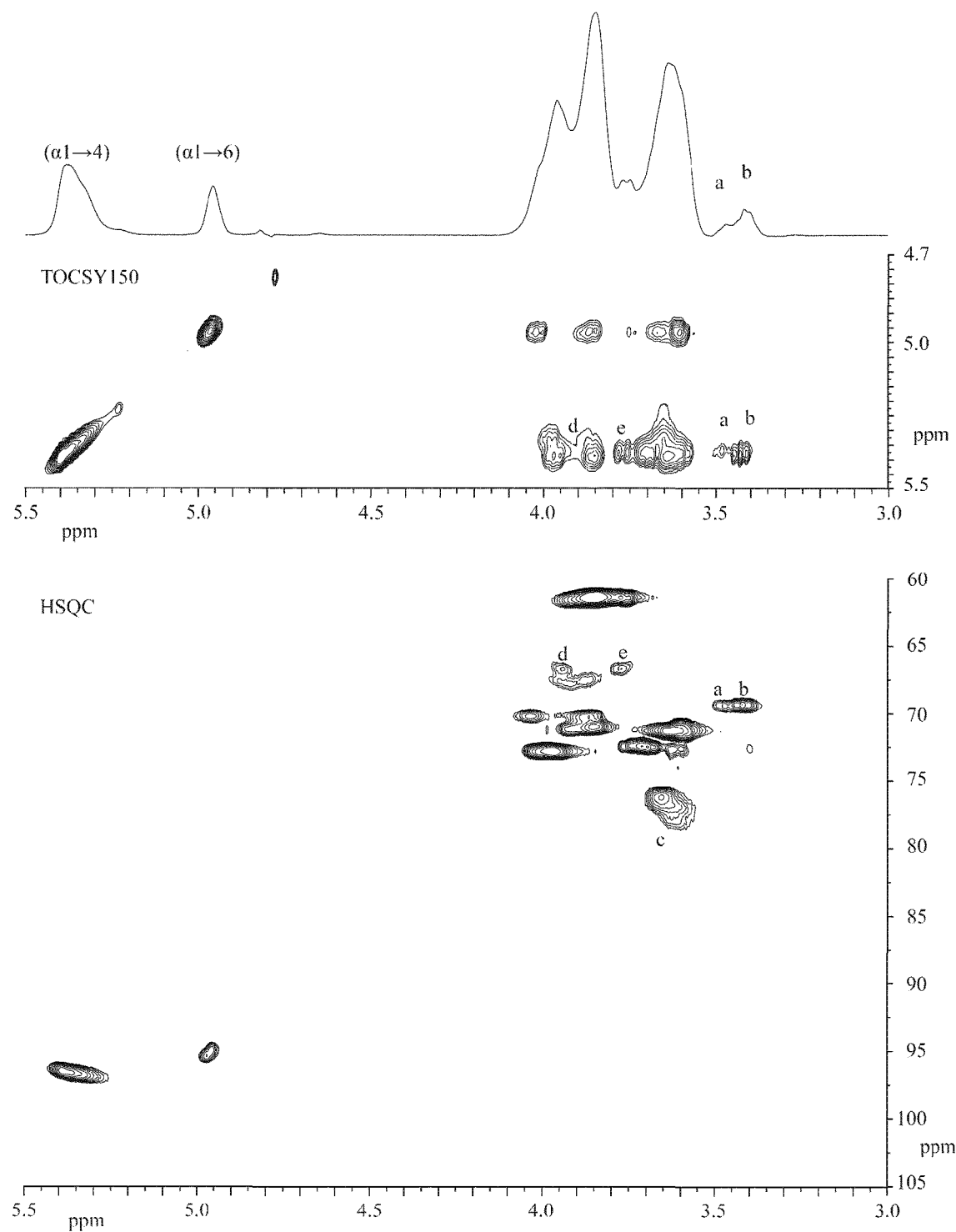
FIG. 5 shows 500-MHz 1D $^1$H NMR spectrum, 2D $^1$H-$^1$H TOCSY spectra (mixing time 150 ms), and 2D $^{13}$C-$^1$H HSQC spectrum (D$_2$O, 298K) of the α-glucan generated by the *L. reuteri* CNCM I-2452 GtfB-ΔN enzyme, isolated by size-exclusion chromatography on a Biogel P2 column. The reaction products were obtained from 0.6% (w v$^{-1}$) amylose V, incubated with 40 µg ml$^{-1}$ of the *L. reuteri* CNCM I-2452 GtfB-ΔN enzyme for 24 h at 37° C. and pH 5.5. Peaks for (α1→4) and (α1→6) anomeric signals have been indicated. Structural reporter peaks a: H-4 for 6-substituted Glcp, b: H-4 for terminal Glcp, c: for H-4 for 4-substituted Glcp, d: H-6a for 6-substituted Glcp and e: H-6b for 6-substituted Glcp.

Structural Characterization of the *L. reuteri* CNCM I-2452 GtfB-ΔN LMM Polysaccharide To further explore the structural characteristics of the *L. reuteri* CNCM I-2452 GtfB-ΔN LMM polysaccharide, the amylose-derived reaction mixture was subjected to Bio-Gel P-2 size-exclusion chromatography. 1D NMR analysis of this polysaccharide showed a linkage ratio (α1→4):(α1→6) =75:25. The typical chemical shift values corresponding to consecutive (α1→6) linkages were not identified in the 2D NMR spectra of this *L. reuteri* CNCM I-2452 GtfB-ΔN polymer (FIG. 5). Methylation analysis revealed the presence of terminal, 4-substituted, 6-substituted, and 4,6-disubstituted glucopyranose residues in a molar percentage of 15, 59, 10, and 16%, which is in agreement with the linkage ratios determined by $^1$H NMR. Taken together, these data confirm that similar to GtfD type of enzymes, the *L. reuteri* CNCM I-2452 GtfB-ΔN synthesizes a reuteran-like α-glucan, providing the first evidence of this product specificity within the GtfB-like GH70 subfamily. The structural characteristics of the different amylose-derived reuteran type of polymers are summarized in Table 1. Regarding its size and (α1→4):(α1→6) linkage ratio, the α-glucan synthesized by the *L. reuteri* CNCM I-2452 GtfB-ΔN resembles mostly the LMM *P. beijingesis* GtfD polymer, however, it contains higher amounts of alternating (α1→4)/(α1→6) glycosidic linkages as indicated by the increased amount of 6-substituted glucopyranosyl units (i.e. 10% rather than 5%).

alternating (α1→3)/(α1→4) linkages and (α1→3,4) branching points by transferring MOS of different DPs [co-pending application EP16172606.2]. Whereas in GSs the active site is blocked beyond subsite −1, the GH70 starch-active enzymes appear to have more than one donor substrate binding subsite, allowing the elongation process to occur by successive transfer of MOS units coming from starch.

*L. reuteri* CNCM I-2452 GtfB-ΔN Acceptor Substrate Reaction Studies

The acceptor substrate specificity of the *L. reuteri* CNCM I-2452 GtfB-ΔN enzyme and *L. reuteri* 121 GtfB were compared by incubating the enzymes in the presence or

TABLE 1

Structural characterization of the polysaccharide formed upon incubation of amylose V with the *L. reuteri* CNCM I-2452 GtfB-ΔN enzyme. For comparison the characteristics of the polymer produced by the *A. chroococcum* and *P. beijingensis* GtfD 4,6-α-GTases are included as well.

| Parameter | Type of glucosyl units | *A. chroococcum* GtfD polymer | *P. beijingensis* GtfD HMM polymer | *P. beijingensis* GtfD LMM polymer | *L. reuteri* CNCM I-2452 GtfB-ΔN polymer |
|---|---|---|---|---|---|
| Methylation analysis (%) | Glcp(1→ | 19 | 17 | 15 | 15 |
| | →4)-Glcp-(1→ | 45 | 54 | 62 | 59 |
| | →6)-Glcp-(1→ | 18 | 11 | 5 | 10 |
| | →4,6)-Glcp-(1→ | 18 | 18 | 18 | 16 |
| NMR chemical shift (%)$^a$ | (α1→4) | 68 | 71 | 77 | 75 |
| | (α1→6) | 32 | 29 | 23 | 25 |
| Molecular mass (10$^3$ Da)$^b$ | | 13 10$^3$ | 27 10$^3$ | 19 | 7 |

$^a$The data represent the ratios of integration of the surface areas of the (α1→6) linkage signal at 4.97 ppm and the (α1→4) linkage signal at 5.36 ppm in the $^1$H NMR spectra of the polysaccharides.
$^b$The average molecular mass of polysaccharide was determined in duplicate.

Figure 6:
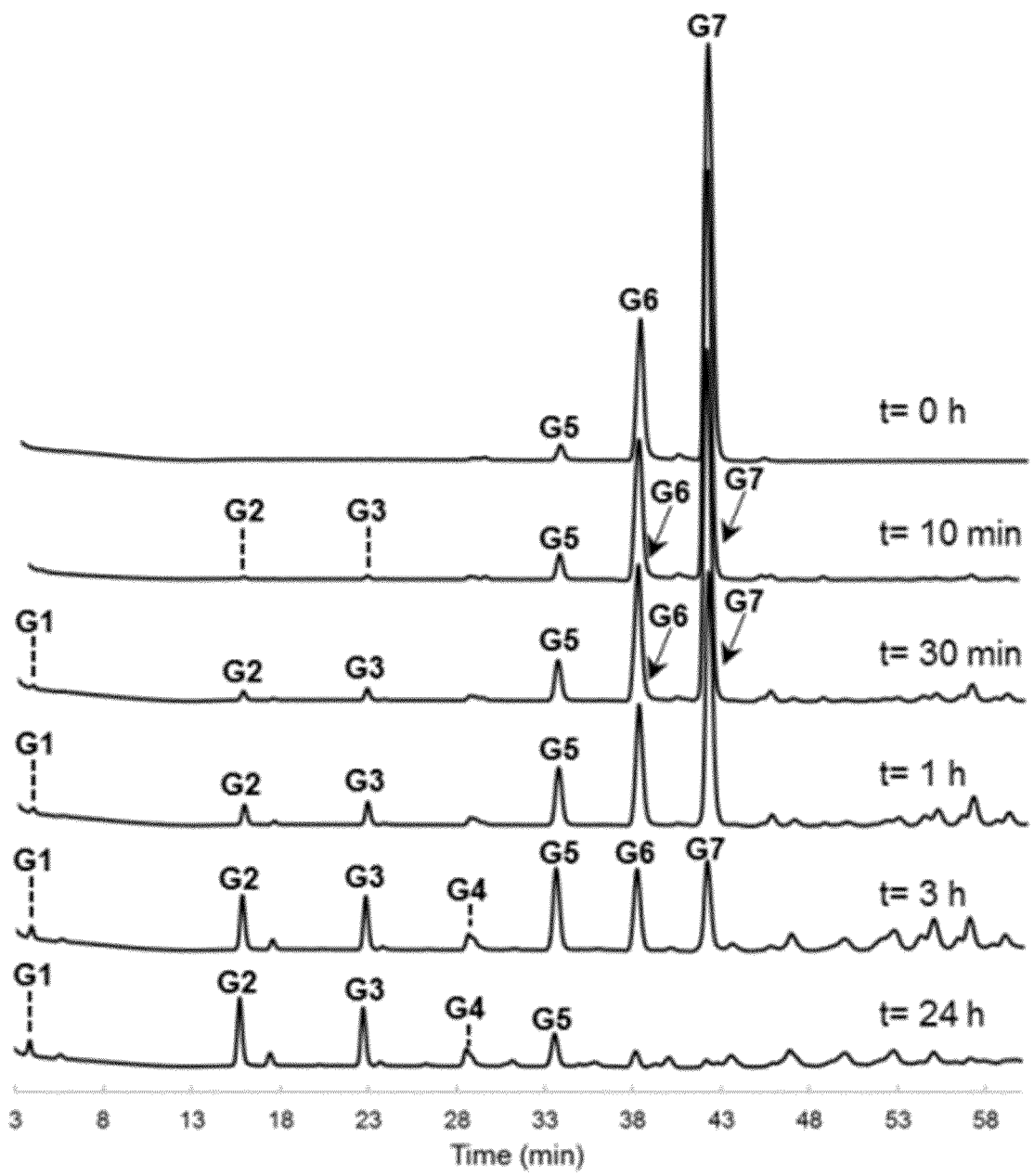
FIG. 6 shows an HPAEC-PAD profile of the oligosaccharide mixture formed upon the incubation of *L. reuteri* CNCM I-2452 GtfB-ΔN (20 µg ml$^{-1}$) with maltoheptaose for t=1 h, 3 h and 24 h (pH 5.5, 37° C.). The identity of peaks was assigned using commercial oligosaccharide standards. G1, glucose; G2-G7, maltose to maltoheptaose; iso-G2, isomaltose; iso-G3, isomaltotriose; Pa, panose.
Figure 7:
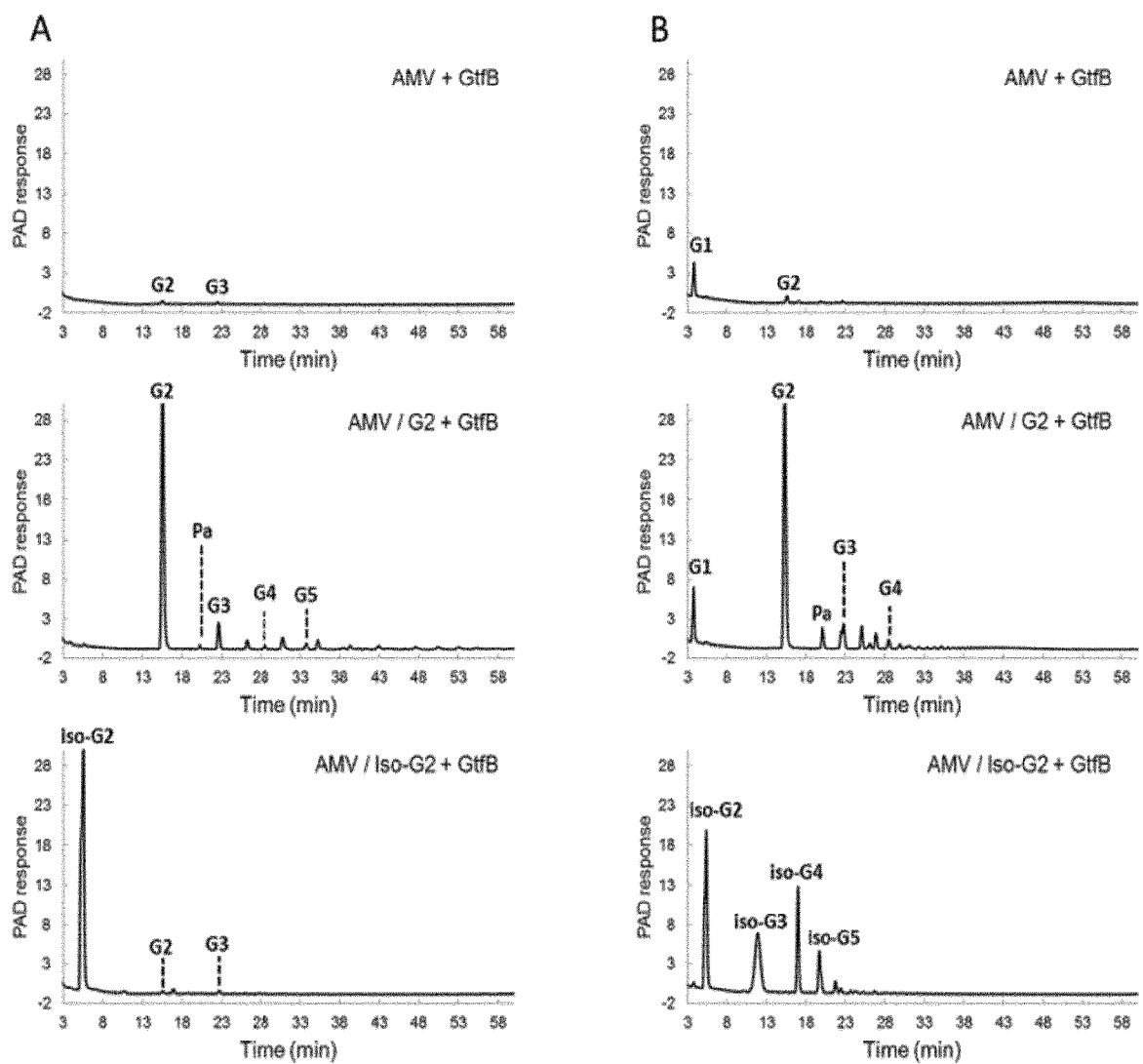
FIG. 7 shows HPAEC-PAD profiles of the oligosaccharide mixtures generated by incubating the *L. reuteri* CNCM I-2452 GtfB-ΔN enzyme (40 µg ml$^{-1}$) (A) and *L. reuteri* 121 GtfB enzyme (40 µg ml$^{-1}$) (B) with 0.35% amylose V (AMV) (donor substrate) or amylose V with 25 mM maltose or 25 mM isomaltose (acceptor substrates) for 24 h at 37° C. The identity of peaks was assigned using commercial oligosaccharide standards. G1, glucose; G2-G4, maltose to maltotetraose; iso-G2-iso-G5, isomaltose to isomaltopentaose; Pa, panose.

Oligosaccharides Formed From Maltoheptaose in Time by the *L. reuteri* CNCM I-2452 GtfB-ΔN To gain a better understanding of the *L. reuteri* NCC 2623 GtfB-ΔN reuteran-like product formation, the oligosaccharides formed from maltoheptaose in time were analyzed by HPAEC (FIG. 6). From maltoheptaose (slightly contaminated with maltohexaose and maltopentaose), the *L. reuteri* CNCM I-2452 GtfB-ΔN released maltose, maltotriose and maltopentaose as the main hydrolysis products, at the early stage of the reaction. Together with these first clear hydrolysis products, a significant number of peaks eluted at higher elution times than the maltooctaose standard (elution time=45.7 min) with products resulting from its transglycosylating activity. After 24 h of reaction, the maltoheptaose substrate was completely depleted, whereas some MOS of low DP and oligosaccharides of unknown structure remained in the reaction mixture. Notably, only trace amounts of glucose were detected during the 24 h of reaction. The formation of maltose and maltotriose as main hydrolysis products, combined with the appearance of peaks corresponding to oligosaccharides with DP higher than 8, suggests that the *L. reuteri* CNCM I-2452 GtfB enzyme preferentially transfers MOS of different DP (instead of glucose) to another glucan chain to form a reuteran-like polymer. This mechanism of polymerization differs from the one observed for GSs, which only transfer a single glucosyl unit per reaction cycle. Instead, the mode of action of the *L. reuteri* CNCM I-2452 GtfB-ΔN resembles that of GtfD 4,6-α-GTase which also produces reuteran-type polymers [PCT/EP2016/071474]. Similarly, the *L. fermentum* GtfB 4,3-α-GTase converts amylose into a polymer containing absence of maltose and isomaltose as acceptor substrates for 24 h. As depicted in FIG. 7A, maltose can serve as acceptor substrate for *L. reuteri* CNCM I-2452 GtfB-ΔN in the presence of amylose V as donor substrate, resulting in formation of panose, maltotriose, maltotetraose and maltopentaose, and significant amounts of other unidentified oligosaccharides. The *L. reuteri* 121 GtfB displayed a different product distribution, but this enzyme was also able to use maltose as an acceptor substrate, yielding panose, maltotriose and maltotetraose, together with a series of elongated products with successive (α1→6) linkages and increasing degrees of polymerization (FIG. 7B). These results suggest that both GtfB enzymes can elongate maltose forming either a new (α1→4) or (α1→6) linkage. Acceptor reactions with isomaltose more clearly reflected the different modes of action of these GtfB enzymes. The *L. reuteri* 121 GtfB enzyme clearly preferred isomaltose as acceptor substrate over maltose, as indicated by the detection of significant amounts of isomaltotriose, isomaltotetraose and isomaltopentaose (resulting from the elongation of the isomaltose by successive (α1→6) linkages). In contrast, no significant change in oligosaccharide formation was observed when amylose V was incubated with *L. reuteri* CNCM I-2452 GtfB-ΔN in the presence or absence of isomaltose. Thus, whereas the *L. reuteri* 121 GtfB preferentially elongates oligosaccharides with α1→6 linked non-reducing ends, the *L. reuteri* CNCM I-2452 GtfB-ΔN is unable to recognize isomaltose as an acceptor substrate, similar to *A. chroococcum* GtfD [PCT/EP2016/071474]. In agreement with these observations, the *L. reuteri* CNCM I-2452 GtfB-ΔN and *L. reuteri* 121 GtfB products differ by the absence or presence of consecutive (α1→6) linkages in their structures, respectively.

Figure 8:
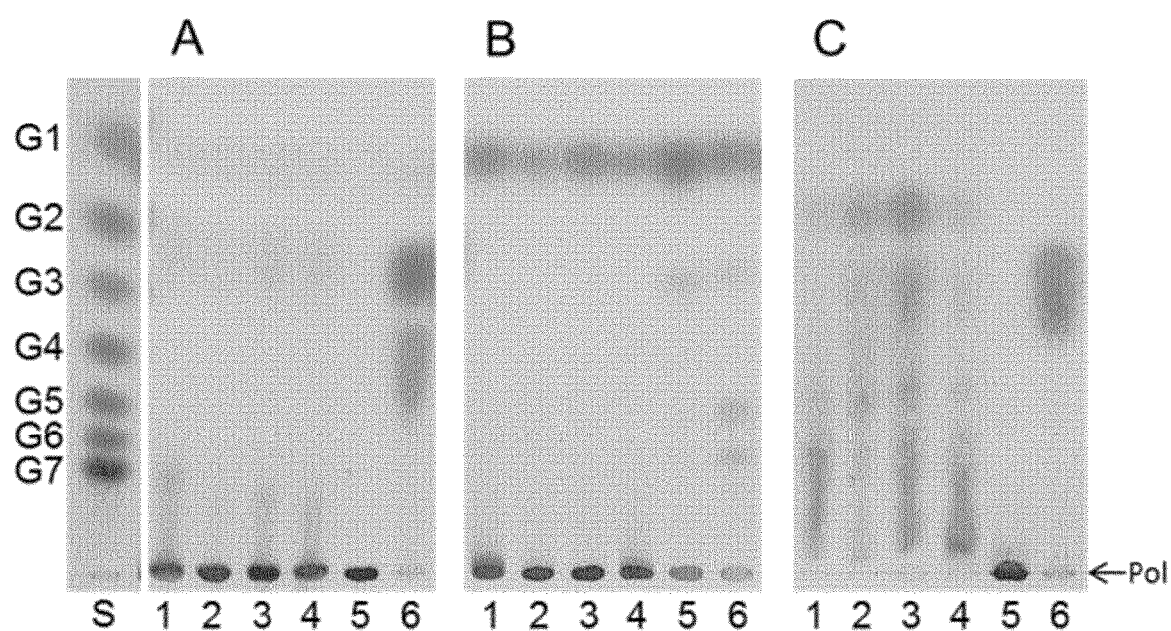
FIG. 8 shows thin-layer chromatography analysis of the *L. reuteri* CNCM I-2452 GtfB-ΔN polysaccharide (5 mg ml$^{-1}$) after digestion with excess amounts of (A) *Aspergillus oryzae* α-amylase, (B) *Chaetomium erraticum* Δdextranase and (C) *Klebsiella planticola* pullulanase M1 for 48 h at 37° C. For comparison, the reuteran-like polymers produced by *A. chroococcum* NCIMB 8003 GtfD and *P. bejingensis* GtfD, and the IMMP product (~90% (α1→6) linkages) synthesized by *L. reuteri* 121 GtfB were subjected to the same enzymatic treatments. Lanes 1-5: reaction products generated by the enzymatic treatment of the *L. reuteri* CNCM I-2452 GtfB-ΔN polymer, *A. chroococcum* GtfD polymer, *P. beijingensis* GtfD HMM polymer, *P. beijingensis* GtfD LMM polymer, and *L. reuteri* 121 GtfB polymer, respectively. Lane 6, positive controls for the α-amylase, dextranase and pullulanase digestions: amylose (A), dextran (B) and pullulan (C). Lane S, standard: glucose (G1) to maltoheptaose (G7); Pol, polymer.

Enzymatic Hydrolysis of the *L. reuteri* CNCM I-2452 GtfB-ΔN Reuteran-Like Polysaccharide The reuteran-like structure of the α-glucan produced by *L. reuteri* CNCM I-2452 GtfB-ΔN was further confirmed by treating this α-glucan with excess amounts of different hydrolytic enzymes: α-amylase, dextranase and pullulanase. For comparison, the IMMP synthesized by the *L. reuteri* 121 GtfB 4,6-α-GTase and the reuteran-like polymers produced by the *A. chroococcum* and *P. beijingensis* GtfD 4,6-α-GTases were subjected in parallel to the same enzymatic treatments. As shown in FIG. 8, the *L. reuteri* CNCM I-2452 GtfB-ΔN polymer was quite resistant to the endo-(1→4) hydrolase activity of the α-amylase. Compared to the amylose control that was completely degraded, only trace amounts of HMM oligosaccharides and maltose were formed when this polymer was incubated with the α-amylase. Similar hydrolytic patterns were obtained for the reuteran-like polymers synthesized by the *A. chroococcum* and *P. beijingensis* GtfD 4,6-α-GTases, whereas these small amounts of maltose or other oligosaccharides were not detected in the case of the IMMP digestion. The *L. reuteri* CNCM I-2452 GtfB-ΔN polymer was also subjected to dextranase and pullulanase M1 enzymatic hydrolysis, which catalyses the hydrolysis of (1→6) glycosidic linkages. Whereas dextranase specifically attacks linear sequences of (α1→6)-linked D-glucopyranosyl repeating units, pullulanase is specific for α1→6 linkages in the backbone chains of pullulan and at branching points of starch molecules. For the dextranase and pullulanase enzymatic treatments, dextran and pullulan were used as positive controls, respectively. As expected, the *L. reuteri* CNCM I-2452 GtfB-ΔN polymer and the *A. chroococcum* and *P. beijingensis* GtfD polymers were not degraded by the action of dextranase, and instead these polymers were hydrolyzed by pullulanase. In contrast, the IMMP product was resistant to the pullulanase treatment, but it was digested by the endo-(α1→6)-hydrolase activity of dextranase. These results are in agreement with the presence of only successive (α1→6) linkages in the *L. reuteri* 121 GtfB polymer and their absence in the *L. reuteri* CNCM I-2452 GtfB-ΔN polymer. Similar to the reuteran type of polymers synthesized by GtfA GS and GtfD 4,6-α-GTases, and differing from the IMMP, this *L. reuteri* CNCM I-2452 GtfB-ΔN polymer appears to contain alternating (α1→6)/(α1→4) linkages and (α1→4,6) branching points.

Figure 9:
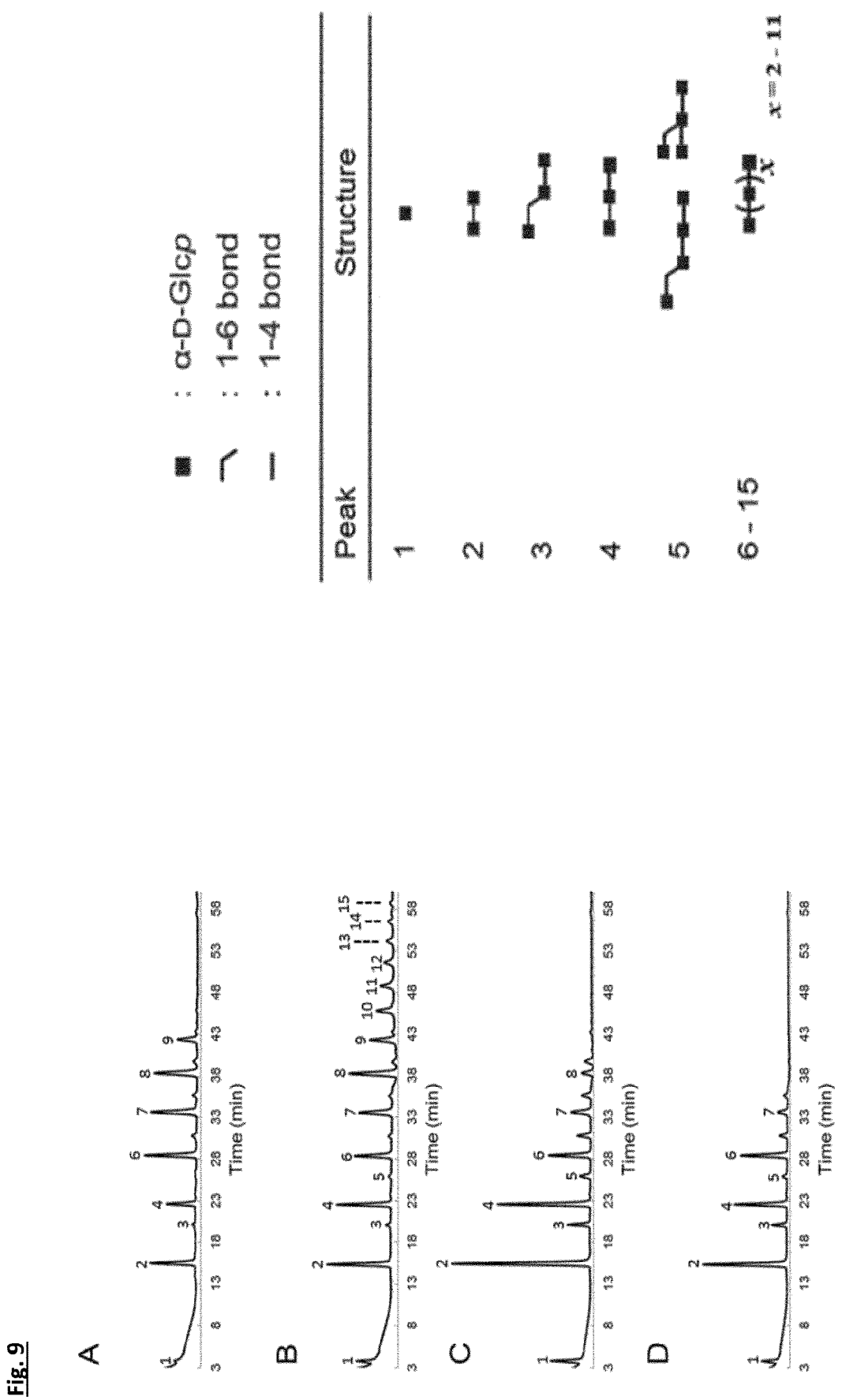
FIG. 9 shows HPAEC-PAD profiles of the oligosaccharides formed by digesting the *L. reuteri* CNCM I-2452 GtfB polymer (A), *P. beijingensis* GtfD LMM polymer (B), *P. beijingensis* GtfD HMM polymer (C), and *A. chroococcum* GtfD polymer (D) using pullulanase M1. Established oligosaccharide structures are included. The identity of peaks 1-16 was assigned using commercial oligosaccharide standards and by comparison with the profile of the pullulanase hydrolysate of reuteran [S. S. van Leeuwen et al., Carbohydr. Res. 343 (2008) 1251-1265.]
Figure 10:
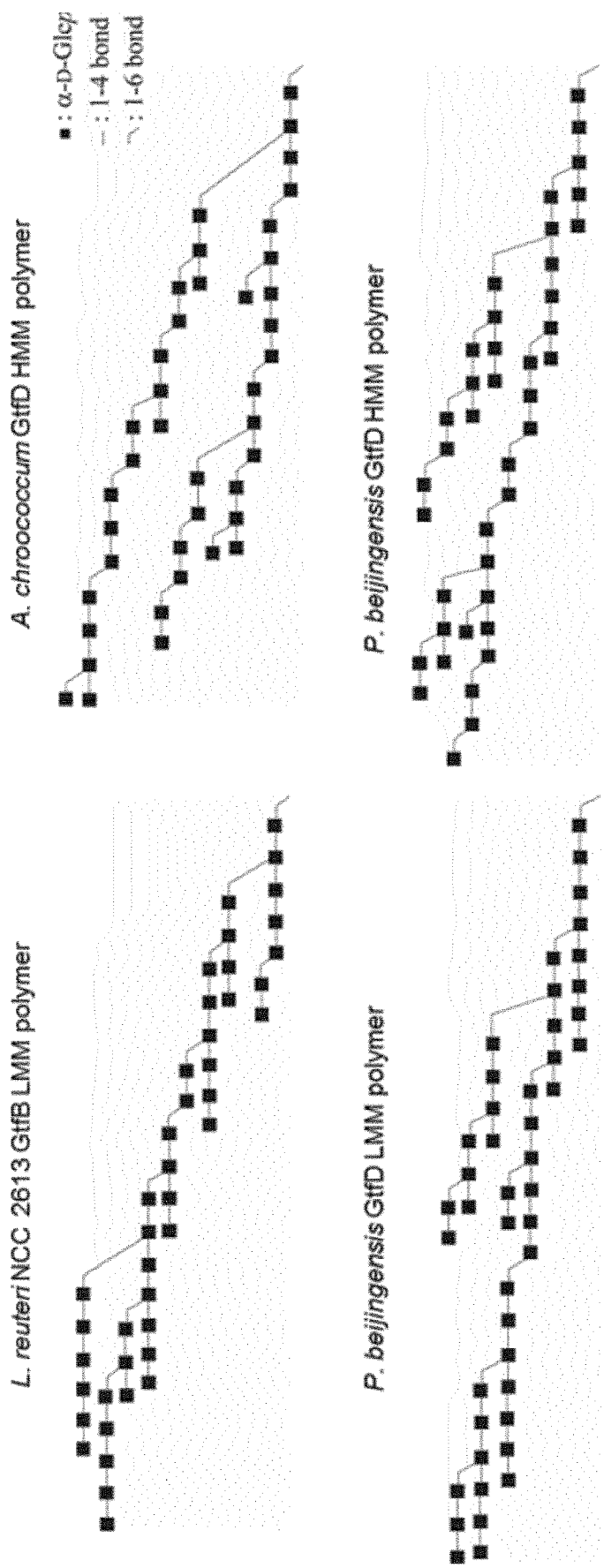
FIG. 10 is a visual representation of composite structures for the *L. reuteri* CNCM I-2452 (also named *L. reuteri* NCC 2613) GtfB-ΔN LMM polymer, the *A. chroococcum* NCIMB 8003 GtfD HMM polymer, and the HMM and LMM *P. beijingensis* GtfD polymers [PCT/EP2016/071474] formed from amylose V. The composite structures contain all structural features established for the respective products. Quantities of each structural element fit with the combined data of 1D $^1$H NMR integration and methylation analysis, as well as enzymatic degradation studies with pullulanase.

Further information about the structure of the *L. reuteri* CNCM I-2452 GtfB-ΔN polymer was obtained by the identification of the reaction products that resulted from the pullulanase treatment by HPAEC. As shown in FIG. 9A, the pullulanase digested the *L. reuteri* CNCM I-2452 GtfB-ΔN polymer, yielding mainly glucose, and a mixture of MOS from DP2 to 7. This finding indicates that this polymer is formed by maltose, maltotriose, maltotetraose, maltopentaose, maltohexaose and maltoheptaose elements linked by single (α1→6) linkages. These structural elements are also present in the LMM *P. beijingensis* GtfD polymer, however with longer linear (α1→4) sequences (from DP8 to DP13) also being detected (FIG. 9B). Pullulanase degraded the HMM reuteran polymers synthesized by *P. beijingensis* GtfD and *A. chroococcum* GtfD enzymes into MOS units up to DP6 and DP5, respectively (FIGS. 9C and 9D). Overall, these HPAEC profiles suggest that the 4,6-α-GTases characterized so far have a preference for transferring different lengths of (α1→4) glucan chains, yielding as a result, reuteran polymers with unique structures. FIG. 10 shows composite models for the reuteran-like polymers produced by the *L. reuteri* NCC2613 GtfB-ΔN and the previously characterized GtfD type of enzymes. The *L. reuteri* NCC2613 GtfB-ΔN enlarges the variety of reuteran-like α-glucans that can be easily synthesized using GH70 enzymes from amylose.

Characterization of GtfB-Treated Wheat Flour: In Vitro Digestion

Wheat flour samples were treated with different concentrations of *L. reuteri* CNCM I-2452 GtfB enzyme as described above. First, the percentage of glucose released by the samples was analyzed by in-vitro digestion. This measurement was set-up to mimic human digestion and gives the percentage of glucose released by the sample compared to a reference.

Figure 11:
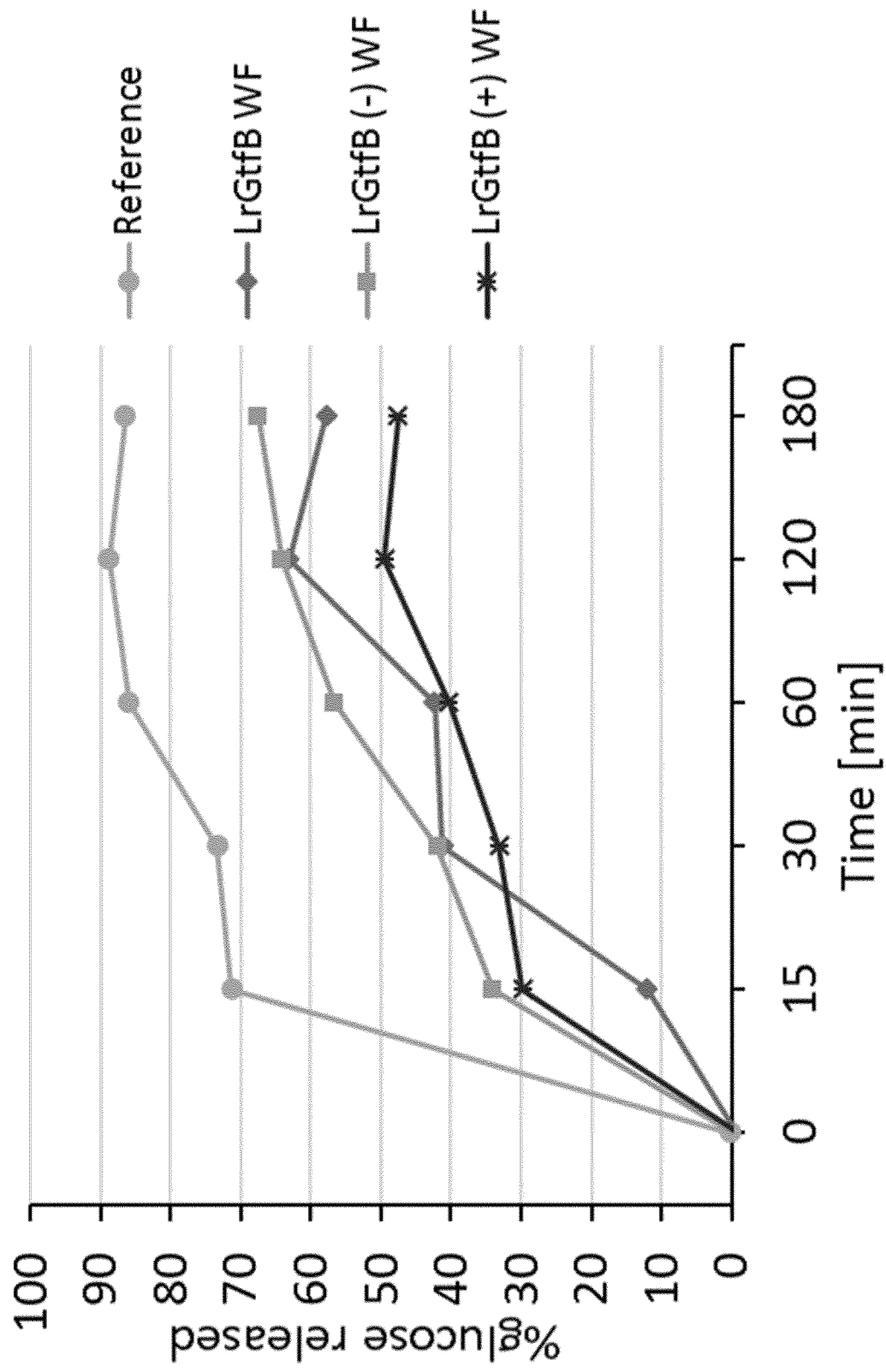
FIG. 11 shows a plot of in-vitro digestion results for wheat flour modified with different quantities of *L. reuteri* CNCM I-2452 GtfB enzyme. Percentage glucose release is plotted against time (minutes).

Glucose released from refined pregelatinized wheat flour modified with different concentration (333.5 (LrGtfB (−)), 667 (LrGtfB) and 1334 (LrGtfB (+)) μg/100 mg starch) of *L. reuteri* CNCM I-2452 GtfB were compared with the reference (FIG. 11). The reference pregelatinized refined wheat flour was rapidly digested by more than 70% after 15 min and reached a plateau (ca. 85%) after 180 min. For wheat flours treated with different concentrations of *L. reuteri* CNCM I-2452 GtfB, the higher the enzyme concentration, the lower the digestibility.

The invention claimed is:

1. A method of producing an α-glucan with a ratio of branching of at least 8%, the method comprising:
contacting a polysaccharide or oligosaccharide substrate with an α-glucanotransferase enzyme to form a glucose polymer,
wherein the polysaccharide or oligosaccharide substrate comprises, at its non-reducing end, at least two (α1→4) linked D-glucose units,
wherein the α-glucanotransferase enzyme is capable of cleaving (α1→4) glucosidic linkages and making new (α1→6) glucosidic linkages without forming consecutive (α1→6) glucosidic linkages,
wherein the glucose polymer comprises linear segments of (α1→4) linked D-glucose units interspersed with (α1→6) glucosidic linkages and having (α1→4,6) branching points,
wherein the α-glucanotransferase comprises an amino acid sequence selected from the group consisting of SEQ ID NOS. 1 and 19.

2. The method of claim 1, wherein the α-glucanotransferase is a GtfB enzyme from a bacterium selected from the group consisting of *L. reuteri* CNCM1-2451, and *L. reuteri* CNCM 1-2452.

3. The method of claim 1, wherein the substrate has a degree of polymerization of at least four.

4. The method of claim 1, wherein the substrate is selected from the group consisting of starch, starch derivatives, malto-oligosaccharides, amylose, amylopectin, maltodextrins, (α1→4) glucans and combinations thereof.

5. The method of claim 1, wherein the polysaccharide or oligosaccharide substrate is contacted with the α-glucanotransferase enzyme at a temperature between 30° C. and 75° C. and a pH of between 4.0 and 9.0.

* * * * *

SEQUENCE LISTING

```
<160> NUMBER OF SEQ ID NOS: 19

<210> SEQ ID NO 1
<211> LENGTH: 1281
<212> TYPE: PRT
<213> ORGANISM: Lactobacillus reuteri
<220> FEATURE:
<223> OTHER INFORMATION: CNCM I-2452

<400> SEQUENCE: 1

Asn Lys Gly Gln Gln Thr Thr Asp Trp Gln Lys Asn Ala Asp Asn Gln
1               5                   10                  15

Trp Val Tyr Asn Gly Lys Thr Asp Gln Asp Leu Lys Gly Thr Gln Tyr
            20                  25                  30
```

```
Val Gln Leu Pro Thr Ile Pro Asp Thr Asn Val Gln Asn Thr Asn
         35                  40                  45

Trp Tyr Phe Val Lys Asp Gly Ile Ala Gln Ser Gly Val Gln Gln Trp
 50                  55                  60

Ala Gly Ser Tyr Tyr Phe Asp Pro Val Thr Tyr Leu Arg Val Asp
 65                  70                  75                  80

Asn Arg Tyr Val Gln Ser Gln Trp Gly Leu Lys Tyr Met Phe Gly Lys
                 85                  90                  95

Asp Gly Arg Ile Ala Thr Gly Leu Tyr Lys Trp Asp Lys Asn Asn Gln
            100                 105                 110

Trp Tyr Tyr Phe Asn Pro Ile Thr Tyr Leu Ala Val Thr Asn Asp Tyr
            115                 120                 125

Ile Gln Ala Asn Asp Gly Asn Trp Tyr Leu Phe Thr Ala Asp Gly Thr
        130                 135                 140

Ala Ala Ser Arg Val Ala Gln Trp Ala Gly Thr Tyr Tyr Tyr Phe Asp
145                 150                 155                 160

Pro Val Thr His Leu Arg Val Asp Asn Tyr Val Gln Ser Gln Trp
                165                 170                 175

Gly Asp Trp Tyr Leu Phe Gly Asn Asp Gly Arg Ile Leu Ser Gly Val
            180                 185                 190

Gln Gln Trp Ala Gly Thr Tyr Tyr Phe Asp Pro Thr Thr Tyr Leu
        195                 200                 205

Arg Val Asp Asp Asp Tyr Val Thr Ser Gln Trp Gly Leu Lys Tyr Met
    210                 215                 220

Phe Gly Lys Asp Gly Arg Ile Ala Thr Gly Leu Tyr Lys Trp Asp Lys
225                 230                 235                 240

Asn Asn Gln Trp Tyr Tyr Phe Asp Pro Thr Thr Tyr Leu Ala Val Thr
                245                 250                 255

Asn Asn Tyr Ile Gln Ala Asn Asp Gly His Trp Tyr Leu Phe Thr Ala
            260                 265                 270

Asp Gly Thr Ala Ala Ser Arg Val Ala Lys Trp Ala Gly Thr Tyr Tyr
        275                 280                 285

Tyr Phe Asp Pro Val Thr His Leu Arg Val Asp Asn Asn Tyr Val Gln
    290                 295                 300

Ser Gln Trp Gly Asp Trp Tyr Met Phe Gly Asn Asp Gly Arg Ile Ile
305                 310                 315                 320

Thr Gly Arg Thr Leu Trp Tyr Gly Asn Tyr Tyr Phe Asp Pro Val
                325                 330                 335

Thr Tyr Leu Lys Val Thr Asn Lys Trp Val Asp Gly Asn Tyr Tyr Asp
            340                 345                 350

Glu Asp Gly Ala Gln Ala Ile Ser Lys Leu Val Thr Ile Asn Asn Arg
        355                 360                 365

Leu Tyr Tyr Phe Asp Asp Gln Gly Lys Glu Ile Ser Asn Gln Phe Arg
    370                 375                 380

Thr Ile Tyr Gly Asn Thr Tyr Tyr Phe Gly Asn Asp Ser Ala Ala Val
385                 390                 395                 400

Thr Gly Gln Gln Thr Ile Asp Gly Lys Val Tyr Asn Phe Ser Lys Tyr
                405                 410                 415

Gly His Leu Leu Gly Asn Arg Tyr Gly Lys Ile Glu Asn Gly Lys Leu
            420                 425                 430

Asn Ile Tyr Ser Leu Ala Asp Asn Ser Leu Ile Lys Thr Val Glu Ala
        435                 440                 445

Gly Pro Trp Glu Asn Met Ala Tyr Ser Met Asp Ser Asn Ser Ile Asn
```

```
             450             455             460
Asn Ile Asp Gly Tyr Ile Ser Tyr Thr Gly Trp Tyr Arg Pro Tyr Gly
465                 470                 475                 480

Thr Ser Gln Asp Gly Lys Thr Trp Tyr Pro Thr Thr Val Ala Asp Trp
                485                 490                 495

Arg Pro Ile Leu Met Tyr Val Trp Pro Ser Lys Asp Val Gln Ala Lys
                500                 505                 510

Phe Ile Gln Tyr Phe Val Asn His Gly Tyr Glu Asn Ser Asn Tyr Gly
            515                 520                 525

Leu Thr Thr Gly Ser Val Lys Asp Leu Ser Glu Asn Thr Ala Ser Ile
        530                 535                 540

Lys Leu Asn Glu Val Ala Gln Asn Leu Arg Tyr Val Ile Glu Gln His
545                 550                 555                 560

Ile Val Ala Ala Lys Ser Thr Ser Gln Leu Ala Asn Asp Ile Asn Asn
                565                 570                 575

Phe Ile Thr Thr Ile Pro Glu Leu Ser Ala Ser Ser Glu Leu Pro Tyr
                580                 585                 590

Gly Gln Val Ile Phe Val Asn Asn Asp Asn Thr Ser Tyr Ala Asp Ser
            595                 600                 605

Lys Tyr Arg Leu Met Ser Arg Thr Ile Asn Asn Gln Thr Gly Asn Asp
        610                 615                 620

Asn Asp Asn Ser Asp Asn Gly Tyr Glu Phe Leu Thr Gly Ile Asp Ile
625                 630                 635                 640

Asp Asn Ser Asn Pro Val Val Gln Ala Glu Asn Leu Asn Trp Glu Tyr
                645                 650                 655

Phe Leu Leu Asn Tyr Gly Lys Leu Met Gly Tyr Asn Pro Asp Gly Asn
                660                 665                 670

Phe Asp Gly Phe Arg Ile Asp Ala Ala Asp His Ile Asp Ala Asp Val
            675                 680                 685

Leu Asp Gln Thr Gly Gln Leu Met Asp Asp Met Tyr His Met Lys Gly
        690                 695                 700

Asn Pro Gln Asn Ala Asn Asn His Leu Ser Tyr Asn Glu Gly Tyr Arg
705                 710                 715                 720

Ser Ser Ala Ala Arg Met Leu Asn Lys Lys Gly Asn Pro Gln Leu Tyr
                725                 730                 735

Met Asp Tyr Val Gly Ser Thr Leu Gly Asn Val Leu Gly Arg Ala Asn
            740                 745                 750

Asn Arg Asp Thr Ile Ser Asn Leu Val Thr Gly Ser Ile Val Asn Arg
        755                 760                 765

Gln Asn Asp Val Thr Glu Asn Glu Ala Thr Pro Asn Trp Ser Tyr Val
770                 775                 780

Thr Asn His Asp Ser Arg Ala Asn Leu Ile Asn Gly Leu Ile Ser Lys
785                 790                 795                 800

Asp His Pro Gly Ala Tyr Lys Ala Glu Tyr Ala Asn Gln Ala Trp Gln
                805                 810                 815

Glu Phe Tyr Ala Asp Gln Lys Lys Thr Asp Lys Gln Tyr Ala Gln Tyr
            820                 825                 830

Asn Val Pro Ala Gln Tyr Ala Ile Leu Leu Ser Asn Lys Asp Thr Val
        835                 840                 845

Pro Gln Ile Tyr Tyr Gly Asp Leu Tyr Asn Glu Thr Ala Gln Tyr Met
        850                 855                 860

Gln Glu Lys Ser Ile Tyr Tyr Asp Ala Ile Thr Thr Leu Met Lys Ala
865                 870                 875                 880
```

Arg Lys Gln Phe Val Ser Gly Gly Gln Thr Met Thr Lys Leu Ser Asp
            885                 890                 895

Asn Leu Ile Ala Ser Val Arg Tyr Gly Lys Gly Val Thr Asn Ala Asn
            900                 905                 910

Ser Glu Gly Thr Asp Ser Leu Ser Arg Thr Ser Gly Met Ala Val Ile
            915                 920                 925

Val Gly Asn Asn Pro Gln Met Ala Glu Gln Thr Ile Ser Ile Asn Met
        930                 935                 940

Gly Arg Ala His Ala Asn Glu Gln Tyr Arg Asn Leu Leu Asp Thr Thr
945                 950                 955                 960

Asp Asn Gly Leu Thr Tyr Asn Ala Asp Gly Ala Glu Asn Pro Glu Thr
            965                 970                 975

Leu Thr Thr Asp Asp Asn Gly Ile Leu Lys Val Thr Val Lys Gly Tyr
            980                 985                 990

Ser Asn Pro Tyr Val Ser Gly Tyr Leu Gly Val Trp Val Pro Val Val
            995                 1000                1005

Ser Gly Asn Gln Asp Val Thr Thr Asn Ala Ala Thr Val Ser Ala Asp
        1010                1015                1020

Ser Asn Lys Ile Phe Glu Ser Asn Ala Ala Leu Asp Ser His Met Ile
1025                1030                1035                1040

Tyr Gln Asp Phe Ser Leu Tyr Gln Pro Glu Pro Thr Ser Thr Glu Asn
            1045                1050                1055

His Ala Tyr Asn Thr Ile Ala Gln Asn Ala Glu Leu Phe Asn Asn Leu
            1060                1065                1070

Gly Ile Thr Asp Phe Trp Met Ala Pro Pro Tyr Thr Gln Tyr Ser Glu
            1075                1080                1085

Ser Arg Tyr Asn Asp Gly Tyr Ser Val Thr Asp Arg Tyr Asn Leu Gly
            1090                1095                1100

Thr Asn Ala Asn Pro Thr Lys Tyr Gly Ser Gly Glu Glu Leu Ala Asn
1105                1110                1115                1120

Ala Ile Ala Ala Leu His Ser Ala Gly Leu Lys Val Gln Val Asp Ile
            1125                1130                1135

Val Met Asn Gln Met Ile Gly Leu Pro Gly Gln Glu Ala Val Thr Val
            1140                1145                1150

Thr Arg Ala Asp Asn Arg Gly Ile Gln Thr Tyr Val Asn Gly Lys Thr
            1155                1160                1165

Tyr Ala Asn Gln Met Tyr Phe Ala Tyr Thr Thr Gly Gly Gly Asn Gly
            1170                1175                1180

Gln Glu Thr Tyr Gly Gly Lys Tyr Leu Ser Glu Leu Gln Ser Lys Tyr
1185                1190                1195                1200

Pro Asp Leu Phe Thr Thr Arg Ala Ile Ser Thr Gly Val Ala Pro Asp
            1205                1210                1215

Pro Thr Thr Arg Ile Thr Lys Trp Ser Ala Lys Tyr Glu Asn Gly Thr
            1220                1225                1230

Ser Leu Gln Asn Ile Gly Ile Gly Leu Ala Val Lys Leu Pro Asn Gly
            1235                1240                1245

Glu Tyr Ala Tyr Leu Arg Ser Ser Asp Asn Lys Ala Phe Asn Thr Thr
            1250                1255                1260

Leu Pro Glu Thr Met Ser Ser Ala Asp Tyr Tyr Ala Asn Ile Glu Asp
1265                1270                1275                1280

Asp

```
<210> SEQ ID NO 2
<211> LENGTH: 31
<212> TYPE: PRT
<213> ORGANISM: Unknown
<220> FEATURE:
<223> OTHER INFORMATION: Primer

<400> SEQUENCE: 2
```

Cys Ala Gly Gly Ala Cys Cys Gly Thr Gly Gly Cys
1               5                   10              15

Ala Thr Thr Thr Ala Cys Thr Thr Gly Gly Ala Ala Thr Cys
            20                  25                  30

```
<210> SEQ ID NO 3
<211> LENGTH: 36
<212> TYPE: PRT
<213> ORGANISM: Unknown
<220> FEATURE:
<223> OTHER INFORMATION: Primer

<400> SEQUENCE: 3
```

Cys Gly Ala Gly Gly Ala Gly Ala Ala Gly Cys Cys Gly Gly Thr
1               5                   10              15

Thr Ala Ala Thr Cys Gly Thr Cys Thr Thr Cys Ala Ala Thr Ala Thr
            20                  25                  30

Thr Ala Gly Cys
        35

```
<210> SEQ ID NO 4
<211> LENGTH: 1631
<212> TYPE: PRT
<213> ORGANISM: Streptococcus thermophilus
<220> FEATURE:
<223> OTHER INFORMATION: NCC 2408

<400> SEQUENCE: 4
```

Ile Cys Ser Ser Tyr Phe Leu Asn Leu Pro Tyr Ile Lys Lys Arg Trp
1               5                   10                  15

Tyr Asn Lys Lys Phe Ile Tyr Arg Gly Glu Tyr His Met Glu Ile Lys
            20                  25                  30

Lys Arg Phe Lys Leu Tyr Lys Ser Gly Lys Gln Trp Ile Arg Ala Ser
        35                  40                  45

Ile Ser Thr Val Ala Ile Ser Thr Gly Leu Ile Leu Gly Gly Gly Val
    50                  55                  60

Val His Ala Ala Glu Asn Gln Pro Gly Gly Thr Gln His Ser Val Ile
65                  70                  75                  80

Asn Thr Thr Asn Asn Gln Asp Gln Glu Asn Gly Lys Gln Asp Asn Ser
                85                  90                  95

Leu Ala Asn Thr Asn Glu Asn Gly Ser Thr Lys Glu Asn Asn Gly Gln
            100                 105                 110

Ala Asn Ala Leu Ser Gln Leu Asn Lys Val Asn Asn Asn Ala Thr Pro
        115                 120                 125

Gln Ala Asp Asn Thr Ala Ala Val Asn Asn Asn Ala Thr Pro Gln Ala
    130                 135                 140

Asp Asn Ala Ala Ala Asn Asp Tyr Asn His Ser Asp Asn Gly Asn Tyr
145                 150                 155                 160

Gly Tyr Ile Asp Ser Ala Thr Ile Asn Asn Gln Leu His Val Val
                165                 170                 175

Gly Trp Ser Ala Thr Asn Gln Ala Val Asn Lys Asp Thr Ser Arg Tyr
            180                 185                 190

```
Val Ile Val Tyr Asp Asp Thr Thr Lys Ser Glu Leu Gly Arg Val Gln
        195                 200                 205

Val Thr Asn Pro Val Ala Arg Pro Asp Val Lys Lys Ala Tyr Asn Val
    210                 215                 220

Tyr Asn Ala Gln Asn Ser Gly Phe Asp Val Asn Val Ser Leu Asn Phe
225                 230                 235                 240

Asp Lys Met Asn Ser Tyr Arg Asp Ala Ile Arg Ile Ser Arg Tyr
                245                 250                 255

Ser Gly Val Pro Asp Gly Asn Ser Asp Tyr Val Asp Tyr Val Ser Gln
                260                 265                 270

Pro Val Val Leu Asp Glu Asn Asp Tyr Ala Tyr Leu Asp Asn Phe Asn
            275                 280                 285

Val Asn Asn Gly Ile Leu His Val Ser Gly Trp His Ala Thr Asn Lys
        290                 295                 300

Ala Ile Lys Arg Pro Asn His Phe Val Ile Leu Tyr Asp Arg Thr Thr
305                 310                 315                 320

Asn Cys Glu Val Ala Arg Gln Arg Val Ile Thr Gly Ile Glu Arg Pro
                325                 330                 335

Asp Val Glu Arg Ala Tyr Pro Gln Val Val Asn Ala Asn Ile Ser Gly
            340                 345                 350

Phe Ala Ala Asp Phe Asp Val Thr Asn Leu Asn Pro Asn Asp Glu Tyr
            355                 360                 365

Gln Ile Leu Ser Arg Tyr Ser Asn Arg Asp Asn Gly Glu Gly Ser Tyr
        370                 375                 380

Val Thr His Trp Phe Asn Pro Gln Arg Leu Val Pro Thr Thr Gln Phe
385                 390                 395                 400

Asn Gly Gly Tyr Leu Asp Asn Phe Asn Ile Ser Lys Ala Gly Gln Val
                405                 410                 415

Ala Val Ser Gly Trp His Ala Thr Asn Leu Ser Asn Ile Gln Ser Asn
            420                 425                 430

Arg Phe Val Ile Leu Phe Asp Asn Thr Ala Asn Arg Gln Val Ala Ser
        435                 440                 445

Val Lys Ile Ser Gly Thr Asp Arg Pro Asp Val Glu Lys Ala Tyr Ser
    450                 455                 460

Gln Val Leu Asn Ala Gly Lys Ser Gly Tyr Asn Val Thr Phe Asp Leu
465                 470                 475                 480

Asn Gln Ser Gln Ile Ala Gln Leu Leu Ala Asn His Ser Tyr Ser Ile
                485                 490                 495

Val Ser Arg Tyr Ser Ala Asp Ala Asn Gly Asp Gly Asn Asn Lys Gln
            500                 505                 510

His Thr Asp Ile Trp Ser Ala Pro Ile Val Leu Asp Lys Thr Ala Ser
        515                 520                 525

Tyr Ile Asp Gly Ile Ser Leu Asn Ser Asn Lys Leu Asn Ile Thr Gly
    530                 535                 540

Trp Met Ala Ser Asp Ala Ser Ala Thr Gln Thr Asn Pro Tyr Val Ile
545                 550                 555                 560

Val Leu Asn Asp Gly Lys Glu Val Thr Arg Gln Lys Leu Thr Leu Thr
                565                 570                 575

Ala Arg Pro Asp Val Ala Arg Val Tyr Pro Asp Ile Tyr Asn Ser Ser
            580                 585                 590

Val Ser Gly Phe Asn Thr Thr Ile Asn Leu Thr Val Pro Glu Leu Asn
        595                 600                 605
```

-continued

Gln Leu Thr Gly Asn Met Gln Val Leu Leu Arg Tyr Ser Ala Asn Ser
610                615                620

Asp Gly Asn Pro Thr Arg Asn Gly Asp Thr Thr Asp Gln Tyr Ser Lys
625                630                635                640

Ser Tyr Ala Thr Asn Gly Gly Asn Phe Asp Phe Val Lys Val Asp Asn
            645                650                655

Asn Gln Val Glu Phe Ser Gly Trp His Ala Ser Asp Gln Ala Thr Asp
        660                665                670

Lys Pro Tyr Gln Trp Ile Ile Val Leu Ala Asn Gly Lys Glu Val Gly
        675                680                685

Arg Gln Leu Ile Ser Ser Thr Thr Tyr Gly Leu Val Ser Tyr Asn Arg
    690                695                700

Pro Asp Val Tyr Asn Val Asn Pro Ala Ile Ser Asp Ser Ser Thr Ser
705                710                715                720

Gly Phe His Gly Ile Ile Thr Leu Asn Ser Ser Ile Lys Asn Val Pro
            725                730                735

Val Gln Leu Val His Arg Phe Ser Asp Asp Gly Gln Asn Gly Glu Arg
        740                745                750

Asn Arg Val Asp Phe Trp Ser Glu Val Met Pro Val Ala Ser Thr Phe
    755                760                765

Gln Lys Gly Ser Asp Gln Val Met Lys Asn Leu Val Ala Lys Pro Gln
770                775                780

Gly Asn Gln Leu Asn Ile Tyr Asn Gly Asn Thr Val Leu Lys Thr Leu
785                790                795                800

Gly Pro Gly Thr Trp Glu Asn Met Ala Phe Ala His Asp Ser Ser Ala
            805                810                815

Ile Asn Asn Ile Asp Gly Tyr Leu Ser Tyr Thr Gly Trp Tyr Arg Pro
        820                825                830

Tyr Gly Thr Ser Gln Asp Gly Lys Thr Trp Tyr Gln Thr Thr Ala Met
    835                840                845

Asp Trp Arg Pro Leu Leu Met Tyr Ile Trp Pro Ser Lys Asp Val Gln
850                855                860

Ala Gln Phe Ile Lys Tyr Phe Val Lys Asn Gly Tyr Glu Asn Ala Asp
865                870                875                880

Tyr Gly Leu Thr Glu Ala Ser Val Ala Asn Leu Asn Lys Asp Thr Asp
            885                890                895

Ala Thr Val Leu Asn Thr Ala Ala Gln Asn Leu Arg Tyr Val Ile Glu
        900                905                910

Gln Ser Ile Ala Thr Asn Lys Gly Thr Arg Lys Leu Ala Asn Asp Ile
    915                920                925

Asn Gly Phe Val Ala Thr Val Pro Glu Leu Ser Thr Ser Ser Glu Leu
930                935                940

Pro Asp Glu Ser Gly Tyr Gly Gln Val Ile Phe Val Asn Asn Asp Asn
945                950                955                960

Thr Ser Tyr Ala Asp Ser Lys Tyr Arg Leu Met Asn Arg Thr Val Asn
            965                970                975

Asn Gln Thr Gly Asn Asp Asp Ser Asp Tyr Arg Pro Glu Phe Leu Val
        980                985                990

Gly Thr Asp Val Asp Asn Ser Asn Pro Val Val Gln Ala Glu Asn Leu
    995                1000               1005

Asn Trp Glu Tyr Phe Leu Leu Asn Tyr Gly Lys Leu Met Gly Tyr Asn
1010               1015               1020

Pro Asp Gly Asn Phe Asp Gly Phe Arg Ile Asp Ala Thr Asp His Ile

-continued

```
             1025                1030                1035                1040
Asp Ala Asp Val Leu Asp Gln Met Gly Gln Leu Met Asn Ala Met Tyr
                 1045                1050                1055
His Met Lys Gly Asn Pro Gln Asn Ala Asn Asn His Leu Ser Tyr Asn
                 1060                1065                1070
Glu Gln Tyr Ser Arg Gly Ala Ala Arg Met Leu Asn Lys Lys Gly Asn
                 1075                1080                1085
Pro Gln Leu Tyr Met Asp Ser Glu Val Phe Gly Thr Leu Glu Asn Val
                 1090                1095                1100
Leu Gly Arg Ala Asn Asn Arg Tyr Asp Ile Ser His Leu Ile Thr Asp
             1105                1110                1115                1120
Ser Ile Val Asn Arg Gln Asn Asp Val Thr Glu Asn Glu Ala Thr Pro
                 1125                1130                1135
Asn Trp Ser Phe Val Thr Asn His Asp Gln Arg Asn Asn Leu Ile Asn
                 1140                1145                1150
Gly Leu Ile Ser Lys Asp His Pro Asp Met Gly Ser Ala Tyr Lys Ala
                 1155                1160                1165
Glu Tyr Ala Asn Gln Ala Trp Gln Glu Phe Tyr Ala Asp Gln Lys Lys
                 1170                1175                1180
Thr Asp Lys Gln Tyr Ala Lys Tyr Asn Val Pro Ala Gln Tyr Ala Ile
             1185                1190                1195                1200
Leu Leu Ser Asn Lys Asp Thr Val Pro Gln Ile Tyr Tyr Gly Asp Leu
                 1205                1210                1215
Tyr Asn Glu Thr Ala Gln Tyr Met Gln Glu Lys Ser Ile Tyr Tyr Asp
                 1220                1225                1230
Ala Ile Thr Thr Leu Met Lys Ala Arg Lys Gln Phe Ile Ser Gly Gly
             1235                1240                1245
Gln Thr Met Thr Lys Leu Ser Asp Asn Leu Ile Ala Ser Val Arg Tyr
                 1250                1255                1260
Gly Lys Gly Val Ala Asn Ala Asn Ser Glu Gly Thr Asp Ser Leu Ser
             1265                1270                1275                1280
Arg Thr Ser Gly Met Ala Val Ile Val Gly Asn Asn Pro Gln Met Ala
                 1285                1290                1295
Glu Gln Thr Ile Ser Ile Asn Met Gly Arg Ala His Ala Asn Glu Gln
                 1300                1305                1310
Tyr Arg Asn Leu Leu Asp Thr Thr Asp Asn Gly Leu Thr Tyr Asn Ala
                 1315                1320                1325
Asp Gly Ala Lys Asn Pro Glu Thr Leu Thr Thr Asp Asn Gly Ile
                 1330                1335                1340
Leu Lys Val Thr Val Lys Gly Tyr Ser Asn Pro Tyr Val Ser Gly Tyr
             1345                1350                1355                1360
Leu Gly Val Trp Val Pro Val Val Ser Gly Asn Gln Asp Val Thr Thr
                 1365                1370                1375
Asn Ala Ala Thr Val Ser Ala Asp Ser Asn Lys Ile Phe Glu Ser Asn
                 1380                1385                1390
Ala Ala Leu Asp Ser His Met Ile Tyr Gln Ser Phe Ser Leu His Gln
                 1395                1400                1405
Pro Lys Pro Thr Ser Thr Glu Asn His Ala Tyr Asn Ile Ile Ala Gln
                 1410                1415                1420
Asn Ala Glu Leu Phe Asn Asn Leu Gly Ile Thr Asp Phe Trp Met Pro
             1425                1430                1435                1440
Pro Ala Tyr Thr Ser Asp Glu Asn Ser Arg Tyr Asn Glu Gly Tyr Ala
                 1445                1450                1455
```

-continued

```
Val Thr Asp Arg Tyr Asn Leu Gly Thr Asn Ala Asn Pro Thr Lys Tyr
            1460                1465                1470
Gly Ser Gly Glu Glu Leu Ala Asn Ala Ile Ala Ala Leu His Ser Ala
        1475                1480                1485
Gly Leu Lys Val Gln Ala Asp Ile Val Leu Asn His Met Met Gly Leu
    1490                1495                1500
Pro Gly Gln Glu Ala Val Thr Val Thr Arg Ala Ser Asp Arg Gly Met
1505                1510                1515                1520
Gln Val Tyr Val Asn Gly Lys Thr Tyr Ala Asn Gln Ile Tyr Phe Ala
                1525                1530                1535
Tyr Thr Arg Gly Gly Gly Glu Gly Gln Lys Asn Tyr Gly Gly Lys Tyr
            1540                1545                1550
Leu Asp Glu Leu Gln Lys Lys Tyr Pro Glu Leu Phe Thr Thr Lys Ala
        1555                1560                1565
Val Ser Thr Gly Val Ala Pro Asp Pro Ser Val His Ile Thr Glu Trp
    1570                1575                1580
Ser Ala Lys Tyr Gln Asn Gly Thr Ile Leu Gln Asn Ile Gly Ile Gly
1585                1590                1595                1600
Leu Ala Val Lys Leu Ala Asn Gly Asp Tyr Ala Tyr Leu Arg Ser Ser
                1605                1610                1615
Asp Asn Lys Ser Phe Asn Thr Leu Leu Pro Ser Glu Ile Ala Leu
            1620                1625                1630

<210> SEQ ID NO 5
<211> LENGTH: 1282
<212> TYPE: PRT
<213> ORGANISM: Lactobacillus delbrueckii subsp. delbrueckii
<220> FEATURE:
<223> OTHER INFORMATION: NCC 828

<400> SEQUENCE: 5

Met Asn Ser Arg Lys Lys Met Met Asn Glu Pro Ser Ser Glu Lys Gln
1               5                   10                  15
Arg Trp Ser Leu Arg Lys Ile Ser Val Gly Met Thr Ser Val Leu Leu
                20                  25                  30
Gly Ala Thr Met Phe Trp Ala Ser Gly Ala Gly Ser Gln Val Lys Ala
            35                  40                  45
Asp Thr Thr Thr Ala Ser Glu Gln Ala Ala Gln Thr Gln Thr Asn Thr
        50                  55                  60
Ala Lys Lys Ala Ala Gly Thr Glu Ser Thr Glu Gln Thr Glu Asp Asn
65                  70                  75                  80
Asn Ala Asn Ala Asp Ala Gly Lys Thr Ala Glu Thr Pro Ala Ala Thr
                85                  90                  95
Asp Asn Gly Ser Gln Glu Thr Thr Thr Glu Ser Thr Ala Ala Ser Ser
            100                 105                 110
Ser Ala Gln Asn Gln Gly Gln Ala Ala Thr Ala Thr Ser Ser Thr Thr
        115                 120                 125
Thr Glu Ala Ala Ser Ser Ile Leu Ser Gln Ala Asp Ser Glu Thr Ala
    130                 135                 140
Asn Ser Asn Thr Ser Gln Val Val Thr Ala Thr Ser Ser Ala Thr Thr
145                 150                 155                 160
Glu Ala Val Ser Ser Ala Ala Asn Gln Thr Gly Gln Lys Val Ser Ser
                165                 170                 175
Ser Asn Asn Lys Ser His Asp Ala Lys Ala His Thr Thr Ser Ala Ala
            180                 185                 190
```

```
Ser Gly Ser Ile Ser Gln Val Asn Asp Gly Gln Pro Ile Thr Gly Leu
        195                 200                 205

Arg His Tyr Ser Asn Asn Lys Leu Glu Tyr Tyr Gly Lys Asp His Val
210                 215                 220

Gln Tyr Arg Asn Arg Tyr Ala Ser Gln Gly Asn Lys Trp Tyr Tyr Phe
225                 230                 235                 240

Gly Ser Asn Gly Asp Ala Val Thr Gly Leu Arg His Tyr Gly Asn Asn
                245                 250                 255

Lys Leu Glu Tyr Tyr Gly Lys Asp His Val Gln Tyr Arg Asn Arg Tyr
            260                 265                 270

Ala Ser Gln Gly Asn Lys Trp Tyr Tyr Phe Gly Ser Asn Gly Asp Ala
        275                 280                 285

Val Thr Gly Leu Arg His Tyr Gly Asn Asn Lys Leu Glu Tyr Tyr Gly
        290                 295                 300

Lys Asp His Val Gln Tyr Arg Asn Arg Tyr Ala Ser Gln Gly Asn Lys
305                 310                 315                 320

Trp Tyr Tyr Phe Gly Ser Asn Gly Asp Ala Val Thr Gly Leu Arg His
                325                 330                 335

Tyr Gly Asn Asn Lys Leu Glu Tyr Tyr Gly Lys Asp His Val Gln Tyr
            340                 345                 350

Arg Asn Arg Tyr Ala Ser Gln Gly Asn Lys Trp Tyr Tyr Phe Gly Ser
        355                 360                 365

Asn Gly Asp Ala Val Thr Gly Leu Arg His Tyr Gly Asn Asn Lys Leu
        370                 375                 380

Glu Tyr Tyr Gly Ala Asp His Val Gln Tyr Arg Asn Arg Tyr Tyr His
385                 390                 395                 400

Glu Gly Asn Lys Phe Tyr Tyr Phe Gly Gly Asn Gly Asp Ala Lys Val
                405                 410                 415

Thr Ile Arg Gly Ala Ile Glu Lys Gly Lys Phe Asn Ile Tyr Asp Met
            420                 425                 430

Arg Thr Asn Lys Leu Ile Lys Ser Leu Asn Ala Gly Thr Trp Glu Asn
        435                 440                 445

Leu Pro Tyr Ser Met Asp Ala Lys Ser Ile Asn Asn Ile Asp Gly Tyr
        450                 455                 460

Leu Ser Tyr Leu Gly Trp Tyr Arg Pro Ile Gly Thr Ser Gln Asn Gly
465                 470                 475                 480

Lys Thr Trp His Lys Thr Arg Ala Val Asp Trp Arg Pro Ile Leu Met
                485                 490                 495

Tyr Ala Trp Thr Asn Lys Asp Val Gln Ala Gln Phe Ile Lys Tyr Phe
            500                 505                 510

Val Asn His Gly Tyr Lys Asn Ala Asn Tyr Gly Leu Thr Lys Ala Ser
        515                 520                 525

Val Ala Asn Leu Asn Lys Gly Thr Asn Val Thr Val Leu Asn Lys Ala
        530                 535                 540

Ala Gln Asn Leu Arg Tyr Val Ile Glu Gln Ser Ile Ala Val Asn Lys
545                 550                 555                 560

Gly Thr Gly Lys Leu Ala Asn Asp Ile Asn Gly Phe Ala Ala Thr Val
                565                 570                 575

Pro Glu Leu Ser Ala Ser Ser Glu Leu Pro Tyr Gly Gln Val Ile Phe
            580                 585                 590

Val Asn Asn Asp Asn Thr Ser Tyr Ala Asp Ser Lys Tyr Arg Leu Met
        595                 600                 605
```

-continued

```
Ser Arg Thr Ile Asn Asn Gln Thr Gly Asn Asp Asn Ser Gly Ser Asp
    610                 615                 620
Asn Gly Tyr Glu Phe Leu Thr Gly Ile Asp Ile Asp Asn Ser Asn Pro
625                 630                 635                 640
Val Val Gln Ala Glu Asn Leu Asn Trp Glu Tyr Phe Leu Leu Asn Tyr
                    645                 650                 655
Gly Lys Leu Met Gly Tyr Asn Pro Asp Gly Asn Phe Asp Gly Phe Arg
                660                 665                 670
Ile Asp Ala Ala Asp His Ile Asp Ala Asp Val Leu Asp Gln Met Gly
                675                 680                 685
Gln Leu Met Asp Asp Met Tyr His Met Lys Gly Asn Pro Gln Asn Ala
690                 695                 700
Asn Asn His Leu Ser Tyr Asn Glu Gly Tyr Arg Ser Gly Ala Ala Arg
705                 710                 715                 720
Met Leu Asn Lys Lys Gly Asn Pro Gln Leu Tyr Met Asp Tyr Val Gly
                725                 730                 735
Ser Thr Leu Gly Asn Val Leu Gly Arg Ala Asn Asn Arg Asp Thr Ile
                740                 745                 750
Ser Asn Leu Ile Thr Gly Ser Ile Val Asn Arg Gln Asn Asp Val Thr
    755                 760                 765
Glu Asn Glu Ala Thr Pro Asn Trp Ser Tyr Val Thr Asn His Asp Gln
770                 775                 780
Arg Ala Asn Leu Ile Asn Gly Leu Ile Ser Lys Asp His Pro Gly Ala
785                 790                 795                 800
Tyr Lys Ala Glu Tyr Ala Asn Gln Ala Trp Gln Glu Phe Tyr Ala Asp
                805                 810                 815
Gln Lys Lys Thr Asp Lys Gln Tyr Ala Gln Tyr Asn Val Pro Ala Gln
                820                 825                 830
Tyr Ala Ile Leu Leu Ser Asn Lys Asp Thr Val Pro Gln Ile Tyr Tyr
                835                 840                 845
Gly Asp Leu Tyr Asn Glu Thr Ala Gln Tyr Met Gln Glu Lys Ser Ile
850                 855                 860
Tyr Tyr Asp Ala Ile Thr Thr Leu Met Lys Ala Arg Lys Gln Phe Val
865                 870                 875                 880
Ser Gly Gly Gln Thr Met Thr Lys Leu Ser Asp Asn Leu Ile Ala Ser
                885                 890                 895
Val Arg Tyr Gly Lys Gly Val Ala Asn Ala Asn Ser Glu Gly Thr Asp
                900                 905                 910
Ser Leu Ser Arg Thr Ser Gly Met Ala Val Ile Val Gly Asn Asn Pro
                915                 920                 925
Gln Met Ala Glu Gln Thr Ile Ser Ile Asn Met Gly Arg Ala His Ala
930                 935                 940
Asn Glu Gln Tyr Arg Asn Leu Leu Asp Thr Thr Asp Asn Gly Leu Thr
945                 950                 955                 960
Tyr Asn Ala Asp Gly Ala Glu Asn Pro Glu Thr Leu Thr Thr Asp Asp
                965                 970                 975
Asn Gly Ile Leu Lys Val Thr Val Lys Gly Tyr Ser Asn Pro Tyr Val
                980                 985                 990
Ser Gly Tyr Leu Gly Val Trp Val Pro Val Val Ser Gly Asn Gln Asp
                995                 1000                1005
Val Thr Thr Asn Ala Ala Thr Val Ser Ala Asp Ser Asn Lys Ile Phe
    1010                1015                1020
Glu Ser Asn Ala Ala Leu Asp Ser His Met Ile Tyr Gln Asp Phe Ser
```

-continued

```
            1025                1030                1035                1040

Leu Tyr Gln Pro Glu Pro Thr Ser Thr Glu Asn His Ala Tyr Asn Ile
                    1045                1050                1055

Ile Ala Gln Asn Ala Lys Leu Phe Asn Asn Leu Gly Ile Thr Asp Phe
            1060                1065                1070

Trp Met Ala Pro Pro Tyr Thr Pro Tyr Ser Glu Ser Arg Tyr Lys Asp
                1075                1080                1085

Gly Tyr Ser Val Thr Asp Arg Tyr Asn Leu Gly Thr Asn Ala Asn Pro
            1090                1095                1100

Thr Lys Tyr Gly Ser Gly Glu Glu Leu Ala Asn Ala Ile Ala Ala Leu
1105                1110                1115                1120

His Ser Ala Gly Leu Lys Val Gln Val Asp Ile Val Met Asn Gln Met
                    1125                1130                1135

Ile Gly Leu Pro Gly Gln Glu Ala Val Thr Val Thr Arg Ala Asp Asn
                1140                1145                1150

Arg Gly Ile Gln Thr Tyr Val Asn Gly Lys Thr Tyr Ala Asn Gln Met
            1155                1160                1165

Tyr Phe Ala Tyr Thr Thr Gly Gly Gly Asn Gly Gln Glu Thr Tyr Gly
        1170                1175                1180

Gly Lys Tyr Leu Ser Glu Leu Gln Ser Lys Tyr Pro Asp Leu Phe Thr
1185                1190                1195                1200

Thr Arg Ala Ile Ser Thr Gly Val Ala Pro Asp Pro Thr Thr Arg Ile
                    1205                1210                1215

Thr Lys Trp Ser Ala Lys Tyr Glu Asn Gly Thr Ser Leu Gln Asn Ile
                1220                1225                1230

Gly Ile Gly Leu Ala Val Lys Leu Pro Asn Gly Asp Tyr Ala Tyr Leu
            1235                1240                1245

Asn Gly Gly Asn Asn Asp Lys Phe Lys Thr Thr Leu Pro Glu Gln Met
            1250                1255                1260

Gly Ser Ile Asp Tyr Tyr Val Gln Gln Glu Leu Lys Asn Tyr Val Gln
1265                1270                1275                1280

Gln Lys

<210> SEQ ID NO 6
<211> LENGTH: 1619
<212> TYPE: PRT
<213> ORGANISM: Lactobacillus reuteri 121 (GtfB)

<400> SEQUENCE: 6

Met Glu Leu Lys Lys His Phe Lys Leu Tyr Lys Ser Gly Lys Gln Trp
1               5                   10                  15

Val Thr Ala Ala Val Ala Thr Ile Ala Phe Ser Ala Gly Val Leu Thr
                20                  25                  30

Thr Ser Glu Val Val His Ala Asp Thr Asn Thr Gly Asp Gln Gln Thr
            35                  40                  45

Glu Gln Val Thr Gln Pro Ser Asn Ser Thr Thr Gln Asp Val Lys Pro
        50                  55                  60

Val Ser Thr Asp Ala Ser Ser Asp Thr Lys Ile Val Ser Asp Asn Lys
65                  70                  75                  80

Glu Asn Asn Asn Gln Val Gly Asn Thr Asn Val Ser Gly Gln Asn Ser
                85                  90                  95

Ser Lys Asp Thr Lys Ser Val Leu Thr Gly Thr Asn Ser Val Thr Gln
                100                 105                 110

Asn Tyr Asp His Asn Asp Asn Gly Asn Tyr Gly Tyr Ile Asp Ser Ala
```

```
            115                 120                 125
Asn Leu Asn Asn Asn Gln Leu Gln Val Ser Gly Trp Ser Ala Thr Asn
130                 135                 140

Gln Asn Ile Asn Lys Asp Asn His Phe Ile Ile Ala Tyr Asp Ser Thr
145                 150                 155                 160

Ser Gln Gln Glu Leu Gly Arg Thr Lys Val Glu Thr Pro Val Ala Arg
                    165                 170                 175

Pro Asp Val Lys Ala Val His Asn Val Tyr Asn Ala Glu Asn Ser Gly
                180                 185                 190

Phe Asn Val Asn Val Ser Leu Asn Phe Asp Lys Met Asn Asn Tyr Arg
            195                 200                 205

Asp Ala Ile Lys Ile Ile Ser Arg Tyr Ser Gly Val Pro Asp Gly Asn
        210                 215                 220

Ser Asp Tyr Val Asp Phe Val Ser Gln Pro Ile Phe Asp Glu Asn
225                 230                 235                 240

Asn Tyr Ala His Leu Asp Asp Phe Ser Val Gln Asn Gly Lys Leu His
                245                 250                 255

Val Ser Gly Trp Asn Ala Thr Asn Lys Ala Ile Gln Asn Pro Asn His
                260                 265                 270

Phe Leu Ile Leu Phe Asp Arg Thr Ile Asn Arg Glu Val Ala Arg Gln
            275                 280                 285

Lys Val Thr Ala Gly Ile Asn Arg Pro Asp Val Glu Lys Ala Tyr Pro
        290                 295                 300

Gln Val Ile Asn Ala Asn Ile Ser Gly Phe Asp Ala Ala Phe Asp Ile
305                 310                 315                 320

Thr Thr Leu Asn Pro Asn Asp Glu Tyr Gln Ile Leu Ser Arg Tyr Ser
                325                 330                 335

Asn Asp Asp Asn Gly Glu Gly Ser Tyr Val Thr Tyr Trp Phe Lys Pro
                340                 345                 350

Gln Arg Ile Ala Pro Ala Asn Gln Phe Asn Ser Gly His Leu Asp Ser
            355                 360                 365

Phe Asn Ile Ser Lys Ala Gly Lys Val Thr Val Ser Gly Trp Gln Ala
        370                 375                 380

Thr Asn Leu Ser Asn Ile Gln Ser Asn Arg Phe Ile Ile Leu Phe Asp
385                 390                 395                 400

Asn Thr Ala Asn His Gln Ile Ala Ser Thr Lys Ile Thr Asn Thr Ala
                405                 410                 415

Arg Pro Asp Val Glu Lys Val Tyr Pro Gln Val Leu Asn Ala Thr Asn
                420                 425                 430

Ser Gly Tyr Asp Val Thr Phe Asp Leu Thr Gln Asp Gln Ile Ala Gln
            435                 440                 445

Leu Leu Pro Asn His Ser Tyr Ser Ile Val Ser Arg Tyr Ser Ala Asp
        450                 455                 460

Ala Asn Gly Asn Gly Asn Asp Lys Gln His Thr Asp Phe Trp Ser Thr
465                 470                 475                 480

Pro Ile Thr Leu Asn Lys Thr Ala Ser Tyr Ile Asp Ser Ile Ser Leu
                485                 490                 495

Asn Gly Asn Glu Leu Asn Val Arg Gly Trp Met Ala Ser Asp Ala Ser
                500                 505                 510

Ala Thr Gln Ala Asn Pro Tyr Leu Ile Val Leu Asn Asn Gly Lys Glu
            515                 520                 525

Val Thr Arg Gln Lys Leu Thr Leu Val Ala Arg Pro Asp Val Ala Lys
        530                 535                 540
```

-continued

```
Val Tyr Pro Asp Val Tyr Ser Ser Leu Asp Ser Gly Phe Asn Thr Thr
545                 550                 555                 560

Ile Lys Leu Thr Val Pro Gln Leu Asn Glu Leu Thr Gly Asn Met Gln
                565                 570                 575

Val Leu Leu Arg Tyr Ser Thr Ala Ala Asp Gly Asn Pro Ile Asn Asn
            580                 585                 590

Gly Gly Phe Thr Asp Gln Tyr Ser Lys Asn Tyr Ala Thr Asn Gly Gly
        595                 600                 605

Ser Phe Asp Phe Val Lys Val Asp Asn Asn Gln Val Ala Phe Ser Gly
    610                 615                 620

Trp His Val Ser Asp Gln Ala Thr Asp Lys Pro Tyr Gln Trp Ile Ile
625                 630                 635                 640

Val Leu Ala Asn Gly Lys Glu Val Gly Arg Gln Leu Ile Ser Ser Thr
                645                 650                 655

Thr Asn Gly Phe Val Ser Tyr Asn Arg Pro Asp Val Tyr Asn Val Asn
            660                 665                 670

Pro Ala Ile Ser Asn Ser Ser Thr Ser Gly Phe Gln Gly Ile Met Thr
        675                 680                 685

Leu Lys Asp Asn Ile Lys Asn Ala Asn Val Gln Leu Val His Arg Phe
    690                 695                 700

Ser Asp Asp Gly Gln Asn Gly Glu Gly Asn Arg Val Asp Tyr Trp Ser
705                 710                 715                 720

Glu Val Met Pro Val Thr Asn Thr Phe Gln Lys Gly Thr Asp Gln Leu
                725                 730                 735

Met Arg Asn Leu Val Ala Lys Pro Asn Lys Asn Gln Leu Lys Ile Tyr
            740                 745                 750

Asn Gly Asn Thr Leu Val Lys Thr Leu Gly Pro Gly Thr Trp Glu Asn
        755                 760                 765

Met Ala Phe Ala Gln Asp Ser Ser Ala Ile Asn Asn Ile Asp Gly Tyr
    770                 775                 780

Leu Ser Tyr Thr Asp Trp Tyr Arg Pro Tyr Gly Thr Ser Gln Asp Gly
785                 790                 795                 800

Lys Thr Trp Tyr Lys Thr Thr Ala Met Asp Trp Arg Pro Leu Leu Met
                805                 810                 815

Tyr Ile Trp Pro Ser Lys Asp Val Gln Ala Gln Phe Ile Lys Tyr Phe
            820                 825                 830

Val Asn Asn Gly Tyr Glu Asn Ala Asn Tyr Gly Leu Thr Lys Asp Thr
        835                 840                 845

Val Ala Asn Ile Asn Lys Asp Thr Asn Thr Thr Val Leu Ala Asn Met
    850                 855                 860

Ala Gln Asn Leu Arg Tyr Val Ile Glu Gln Ser Ile Ala Ala Asn Lys
865                 870                 875                 880

Gly Thr Ser Lys Leu Ala Asn Asp Ile Asn Ser Phe Ala Ala Thr Val
                885                 890                 895

Pro Glu Leu Ser Ala Ser Ser Glu Leu Ser Leu Gln Ser Met Pro Asn
            900                 905                 910

Tyr Arg Pro Asp Lys Ser Gly Thr Ile Asp Ser Asp Gln Val Ile Phe
        915                 920                 925

Val Asn Asn Asn Ser Lys Asp Pro Arg Lys Gly Asn Thr Ser Tyr Ala
    930                 935                 940

Asp Ser Asn Tyr Arg Leu Met Asn Arg Thr Ile Asn Asn Gln Ala Gly
945                 950                 955                 960
```

-continued

```
Asn Asn Asn Ser Asp Asn Ser Pro Glu Leu Val Gly Asn Asp Ile
                965             970             975
Asp Asn Ser Asn Pro Val Val Gln Ala Glu Asn Leu Asn Trp Glu Tyr
            980             985             990
Phe Leu Leu Asn Tyr Gly Lys Leu Met Gly Tyr Asn Pro Asp Gly Asn
            995             1000            1005
Phe Asp Gly Phe Arg Val Asp Ala Ala Asp Asn Ile Asp Ala Asp Val
    1010            1015            1020
Leu Asp Gln Met Gly Gln Leu Met Asn Asp Met Tyr His Thr Lys Gly
1025            1030            1035            1040
Asn Pro Gln Asn Ala Asn Asp His Leu Ser Tyr Asn Glu Gly Tyr His
                1045            1050            1055
Ser Gly Ala Ala Gln Met Leu Asn Glu Lys Gly Asn Pro Gln Leu Tyr
                1060            1065            1070
Met Asp Ser Gly Glu Phe Tyr Thr Leu Glu Asn Val Leu Gly Arg Ala
                1075            1080            1085
Asn Asn Arg Asp Asn Ile Gly Asn Leu Ile Thr Asn Ser Ile Val Asn
            1090            1095            1100
Arg Gln Asn Asp Thr Thr Glu Asn Glu Ala Thr Pro Asn Trp Ser Phe
1105            1110            1115            1120
Val Thr Asn His Asp Gln Arg Lys Asn Leu Ile Asn Arg Leu Ile Ile
                1125            1130            1135
Lys Asp His Ser Asn Ile Pro Asp Ile Met Gly Ser Ala Tyr Lys Val
                1140            1145            1150
Glu Tyr Ala Asn Gln Ala Trp Gln Glu Phe Tyr Ala Asp Gln Glu Lys
                1155            1160            1165
Thr Asn Lys Gln Tyr Ala Gln Tyr Asn Val Pro Ala Gln Tyr Ala Ile
    1170            1175            1180
Leu Leu Ser Asn Lys Asp Thr Val Pro Gln Val Tyr Tyr Gly Asp Leu
1185            1190            1195            1200
Tyr Asn Glu Thr Ala Gln Tyr Met Gln Glu Lys Ser Ile Tyr Tyr Asp
                1205            1210            1215
Ala Ile Thr Thr Leu Met Arg Ala Arg Lys Gln Phe Val Ser Gly Gly
                1220            1225            1230
Gln Thr Met Thr Lys Leu Asn Asn Asn Leu Leu Ala Ser Val Arg Tyr
                1235            1240            1245
Gly Lys Gly Val Val Asp Ala Asn Ser Asn Gly Thr Asp Lys Leu Ser
    1250            1255            1260
Arg Thr Ser Gly Met Ala Val Leu Val Gly Asn Asp Ser Asn Met Ala
1265            1270            1275            1280
Gln Gln Ser Val Ala Ile Asn Met Gly Arg Ala His Ala Asn Gln Gln
                1285            1290            1295
Tyr Arg Asn Leu Ile Asp Thr Thr Glu Asn Gly Leu Thr Tyr Asp Ala
                1300            1305            1310
Asp Asn Ser Glu Asn Pro Ala Ile Leu Thr Thr Asp Ser Asn Gly Ile
                1315            1320            1325
Leu Lys Val Thr Val Lys Gly Tyr Ser Asn Pro Tyr Val Ser Gly Tyr
    1330            1335            1340
Leu Gly Val Trp Val Pro Val Ile Ser Gly Asp Gln Asp Val Thr Thr
1345            1350            1355            1360
Asn Ala Ser Asp Val Val Ala Asn Lys Glu Lys Thr Phe Glu Ser Asn
                1365            1370            1375
Ala Ala Leu Asp Ser His Met Ile Tyr Glu Asp Phe Ser Leu Phe Gln
```

```
                1380                1385                1390
Pro Glu Pro Thr Ser Val Glu Asn His Ala Tyr Asn Val Ile Ala Lys
        1395                1400                1405
Asn Ala Ser Leu Phe Ser Asp Leu Gly Ile Thr Asp Phe Trp Met Ala
        1410                1415                1420
Pro Ala Tyr Thr Pro Phe Gly Arg Ser Arg Tyr Asn Glu Gly Tyr Ser
1425                1430                1435                1440
Met Thr Asp Arg Tyr Asn Leu Gly Thr Thr Ala Asn Pro Thr Lys Tyr
            1445                1450                1455
Gly Ser Gly Glu Glu Leu Ala Asn Thr Ile Ala Ala Leu His Lys Ala
            1460                1465                1470
Gly Leu Lys Val Gln Glu Asp Ile Val Met Asn Gln Met Ile Gly Phe
        1475                1480                1485
Ser Gly Gln Glu Ala Val Thr Val Thr Arg Thr Asn Asn Arg Gly Met
        1490                1495                1500
Gln Ile His Val Asn Gly Gln Thr Tyr Ala Asn Gln Ile Tyr Phe Ala
1505                1510                1515                1520
Tyr Thr Thr Gly Gly Gly Asn Gly Gln Glu Thr Tyr Gly Gly Lys Tyr
            1525                1530                1535
Leu Ala Glu Leu Gln Lys Asn Tyr Pro Asp Leu Phe Thr Thr Lys Ala
            1540                1545                1550
Ile Ser Thr Gly Val Ala Pro Asp Pro Thr Val Arg Ile Asn Lys Trp
        1555                1560                1565
Ser Ala Lys Tyr Gln Asn Gly Thr Ser Leu Gln Asn Ile Gly Ile Gly
        1570                1575                1580
Leu Ala Val Lys Leu Ala Asn Gly Asp Tyr Ala Tyr Leu Asn Ser Gly
1585                1590                1595                1600
Asp Asn Lys Ala Phe Asn Thr Leu Leu Pro Thr Ala Ile Ser Leu Asn
            1605                1610                1615
Phe Asn Asn

<210> SEQ ID NO 7
<211> LENGTH: 1620
<212> TYPE: PRT
<213> ORGANISM: Lactobacillus reuteri ML1 (ML4)

<400> SEQUENCE: 7

Met Glu Ile Lys Lys His Phe Lys Leu Tyr Lys Ser Gly Lys Gln Trp
1               5                   10                  15
Val Thr Ala Ser Ile Ala Thr Phe Ala Val Ser Thr Gly Leu Val Leu
            20                  25                  30
Gly Gly Gly Val Val His Ala Ala Asp Asn His Pro Thr Thr Thr Ser
        35                  40                  45
Ala Ser Val Thr Asn Thr Val Asn Asn Leu Lys Pro Gln Asn Asp Pro
    50                  55                  60
Glu Gln Gln Asn Asn Thr Gln Glu Ser Asn Thr Val Glu Phe Pro Lys
65                  70                  75                  80
Lys Asp Ser Gln Asp Asn Ala Val Gln Pro Leu Lys Glu Thr Ala Val
                85                  90                  95
Met Pro Asn Ala Thr Asn Lys Asp Gly Ala Lys Ala Ser Ile Thr Asn
            100                 105                 110
Asn Ala His Thr Asp Asn Thr Ile Tyr Gly Asn Ile Asp Pro Thr Thr
        115                 120                 125
Ile Asn Asp Lys Glu Leu His Val Thr Gly Trp Asn Ala Thr Asn Gln
```

```
              130                 135                 140
Ala Ile Asn Lys Asn Glu Ser Arg Tyr Val Ile Ala Tyr Asp Asp Thr
145                 150                 155                 160

Thr Asn Ser Glu Leu Gly Arg Thr Lys Ile Thr Asn Gln Ile Ala Arg
                165                 170                 175

Pro Asp Val Glu Lys Val His Lys Asp Ile Tyr Asn Ala Gln Asn Ser
            180                 185                 190

Gly Phe Asn Val Asn Ile Ser Leu Asp Phe Asn Lys Met Asn Asn Tyr
        195                 200                 205

Arg Asp Ala Ile Lys Ile Ile Ser Arg Tyr Ser Gly Val Pro Asn Gly
    210                 215                 220

Asn Ser Asp Tyr Val Asp Phe Val Ser Gln Pro Ile Ile Phe Asp Glu
225                 230                 235                 240

Asn Asn Tyr Ala Tyr Leu Asp Asp Phe Ser Val Gln Asn Gly Arg Leu
                245                 250                 255

His Val Ser Gly Arg Asn Ala Thr Asn Lys Ala Ile Gln Arg Pro Asn
            260                 265                 270

His Phe Leu Ile Leu Phe Asp Arg Thr Val Asn Arg Glu Val Ala Arg
        275                 280                 285

Gln Lys Val Thr Ala Gly Ile Asn Arg Ser Asp Val Glu Lys Val Tyr
    290                 295                 300

Pro Gln Val Val Asn Ala Asn Val Ser Gly Phe Asp Ala Thr Phe Asp
305                 310                 315                 320

Thr Ile Asn Leu Asn Pro Asn His Glu Tyr Gln Ile Leu Ser Arg Tyr
                325                 330                 335

Ser Asn Asn Gly Asp Gly Glu Gly Asp Tyr Val Thr Tyr Trp Phe Asn
            340                 345                 350

Pro Gln Arg Ile Ala Pro Val Asn Gln Phe Asn Asn Gly His Leu Asp
        355                 360                 365

Asn Phe Asp Ile Ser Lys Ala Gly Lys Val Thr Val Ser Gly Trp Gln
    370                 375                 380

Ala Thr Asn Leu Ser Asn Ile Gln Asn Asn Arg Tyr Ile Ile Leu Phe
385                 390                 395                 400

Asp Thr Thr Ala Asn Cys Gln Ile Ala Ser Met Lys Val Thr Gly Val
                405                 410                 415

Asp Arg Pro Asp Val Ala Lys Val Tyr Pro Gln Ile Leu Asn Ala Asn
            420                 425                 430

Lys Ser Gly Tyr Asn Val Thr Phe Asp Leu Thr Gln Ala Gln Ile Ala
        435                 440                 445

Gln Leu Phe Pro Asn His Ser Tyr Ser Ile Val Ser Arg Tyr Ser Ala
    450                 455                 460

Asp Pro Asn Gly Asn Gly Asn Asp Lys Gln His Thr Asp Phe Trp Ser
465                 470                 475                 480

Ala Pro Ile Val Leu Asn Lys Thr Ala Ser Tyr Ile Asp Asp Ile Ser
                485                 490                 495

Leu Asn Gly Asp Val Leu Asn Val Lys Gly Trp Met Ala Ser Asp Ala
            500                 505                 510

Ser Ala Thr Gln Ala Asn Pro Tyr Ile Ile Ile Leu Asn Asn Gly Lys
        515                 520                 525

Glu Val Thr Arg Gln Lys Leu Thr Leu Asn Asp Arg Pro Asp Val Ala
    530                 535                 540

Lys Val Tyr Pro Asp Val Tyr Asn Ser Leu Ala Ser Gly Phe Asp Thr
545                 550                 555                 560
```

```
Thr Ile Lys Leu Thr Asn Ser Gln Leu Asn Ala Leu Asn Gly Asn Met
                565                 570                 575

Gln Ile Leu Leu Arg Tyr Ser Ala Ala Asp Gly Asn Pro Ile Asn
                580                 585                 590

Asn Gly Gly Phe Thr Asp Gln Tyr Ser Lys Asn Tyr Ala Thr Asn Gly
                595                 600                 605

Gly Ser Phe Asp Phe Val Lys Val Asp Asn Asn Gln Val Ala Phe Ser
            610                 615                 620

Gly Trp His Val Ser Asp Gln Ala Thr Asp Lys Pro Tyr Gln Trp Ile
625                 630                 635                 640

Ile Val Leu Val Asn Gly Lys Glu Val Gly Arg Gln Leu Ile Ser Ser
                645                 650                 655

Thr Thr Asn Gly Leu Val Ser Tyr Asn Arg Pro Asp Val Tyr Asn Val
                660                 665                 670

Asn Pro Ala Ile Ser Asn Ser Thr Ser Gly Phe Gln Gly Ile Met
            675                 680                 685

Thr Leu Lys Asp Asn Ile Lys Asn Ala Asn Val Gln Leu Val His Arg
            690                 695                 700

Phe Ser Asp Asp Gly Gln Asn Gly Glu Gly Asn Arg Val Asp Tyr Trp
705                 710                 715                 720

Ser Glu Val Met Pro Val Thr Asn Thr Phe Gln Lys Gly Thr Asp Gln
                725                 730                 735

Leu Met Arg Asn Leu Val Ala Lys Pro Asn Lys Asn Gln Leu Lys Ile
            740                 745                 750

Tyr Asn Gly Asn Thr Leu Val Lys Thr Leu Gly Pro Gly Thr Trp Glu
            755                 760                 765

Asn Met Ala Phe Ala Gln Asp Ser Ser Ala Ile Asn Asn Ile Asp Gly
            770                 775                 780

Tyr Leu Ser Tyr Thr Gly Trp Tyr Arg Pro Tyr Gly Thr Ser Gln Asp
785                 790                 795                 800

Gly Lys Thr Trp Tyr Glu Thr Thr Ala Met Asp Trp Arg Pro Leu Leu
                805                 810                 815

Met Tyr Ile Trp Pro Ser Lys Asp Val Gln Ala Gln Phe Ile Lys Tyr
                820                 825                 830

Phe Val Asn Asn Gly Tyr Glu Asn Ala Asn Tyr Gly Leu Thr Glu Ser
            835                 840                 845

Ser Val Ala Ser Phe Ser Lys Asp Thr Asn Ala Asn Leu Leu Asp Val
            850                 855                 860

Thr Ala Gln Asn Leu Arg Tyr Val Ile Glu Gln Ser Ile Ala Ala Asn
865                 870                 875                 880

Lys Gly Thr Ser Lys Leu Ala Asn Asp Ile Asn Ser Phe Ala Ala Thr
                885                 890                 895

Val Pro Glu Leu Ser Ala Ser Ser Leu Ser Leu Gln Ser Met Pro
                900                 905                 910

Asn Tyr Arg Pro Asp Glu Ser Gly Thr Val Asp Ser Asp Gln Val Ile
            915                 920                 925

Phe Val Asn Asn Asn Ser Lys Asp Pro Arg Lys Gly Asn Thr Gly Tyr
            930                 935                 940

Ala Asp Ser Asn Tyr Arg Leu Met Asn Arg Thr Ile Asn Asn Gln Ala
945                 950                 955                 960

Gly Asn Asn Asn Ser Asp Asn Ser Pro Glu Leu Leu Val Gly Asn Asp
                965                 970                 975
```

-continued

Ile Asp Asn Ser Asn Pro Val Val Gln Ala Glu Asn Leu Asn Trp Glu
            980                 985                 990

Tyr Phe Leu Leu Asn Tyr Gly Lys Leu Met Gly Tyr Asn Pro Asp Gly
        995                 1000                1005

Asn Phe Asp Gly Phe Arg Val Asp Ala Ala Asp Asn Ile Asp Ala Asp
    1010                1015                1020

Val Leu Asp Gln Met Gly Gln Leu Met Asn Asp Met Tyr His Thr Lys
1025                1030                1035                1040

Gly Asn Pro Gln Asn Ala Asn Asp His Leu Ser Tyr Asn Glu Gly Tyr
            1045                1050                1055

His Ser Gly Ala Ala Gln Met Leu Asn Glu Lys Gly Asn Pro Gln Leu
        1060                1065                1070

Tyr Met Asp Ser Gly Glu Phe Tyr Thr Leu Glu Asn Val Leu Gly Arg
    1075                1080                1085

Ala Asn Asn Arg Asp Ser Ile Gly Asn Leu Ile Thr Asn Ser Val Val
    1090                1095                1100

Asn Arg Gln Asn Asp Thr Thr Glu Asn Glu Ala Thr Pro Asn Trp Ser
1105                1110                1115                1120

Phe Val Thr Asn His Asp Gln Arg Lys Asn Leu Ile Asn Arg Leu Ile
            1125                1130                1135

Ile Lys Gly His Pro Asn Ile Pro Asp Ile Met Gly Ser Ala Tyr Lys
        1140                1145                1150

Ala Glu Tyr Ala Asn Gln Ala Trp Gln Glu Phe Tyr Ala Asp Gln Lys
        1155                1160                1165

Lys Thr Asn Lys Gln Tyr Asp Gln Tyr Asn Val Pro Ala Gln Tyr Ala
    1170                1175                1180

Ile Leu Leu Ser Asn Lys Asp Thr Val Pro Gln Val Tyr Tyr Gly Asp
1185                1190                1195                1200

Leu Tyr Asn Glu Thr Ala Gln Tyr Met Gln Glu Lys Ser Ile Tyr Tyr
            1205                1210                1215

Asp Thr Ile Thr Thr Leu Met Lys Ala Arg Lys Gln Phe Val Ser Gly
        1220                1225                1230

Gly Gln Thr Met Thr Lys Leu Asn Asn Asn Leu Leu Ala Ser Val Arg
        1235                1240                1245

Tyr Gly Lys Gly Val Ala Asp Ser Asn Ser Asn Gly Thr Asp Lys Leu
    1250                1255                1260

Ser Arg Thr Ser Gly Ile Ala Val Leu Val Gly Asn Asp Ser Asn Met
1265                1270                1275                1280

Ala Gln Gln Thr Val Ala Ile Asn Met Gly Arg Ala His Ala Asn Gln
            1285                1290                1295

Gln Tyr Arg Asn Leu Ile Asp Thr Thr Glu Asn Gly Leu Thr Tyr Asp
        1300                1305                1310

Gly Glu Asn Ser Glu Asn Pro Ala Ile Leu Thr Thr Asp Ser Asn Gly
        1315                1320                1325

Ile Leu Lys Val Thr Val Lys Gly Tyr Ser Asn Pro Tyr Val Ser Gly
    1330                1335                1340

Tyr Leu Gly Val Trp Val Pro Val Ile Ser Gly Asp Gln Asp Val Thr
1345                1350                1355                1360

Thr Ser Ala Ser Asp Val Ala Asp Lys Glu Lys Thr Phe Glu Ser
            1365                1370                1375

Asn Ala Ala Leu Asp Ser His Met Ile Tyr Glu Asp Phe Ser Leu Phe
        1380                1385                1390

Gln Pro Glu Pro Thr Asn Val Glu Asn His Ala Tyr Asn Val Ile Ala

```
              1395                1400                1405
Lys Asn Ala Asn Leu Phe Asn Asp Leu Gly Ile Thr Asp Phe Trp Met
    1410                1415                1420
Ala Pro Ala Tyr Thr Pro Phe Gly Met Ser Arg Tyr Asn Glu Gly Tyr
1425                1430                1435                1440
Ser Met Thr Asp Arg Tyr Asn Leu Gly Thr Thr Ala Asn Pro Thr Lys
                1445                1450                1455
Tyr Gly Ser Gly Glu Glu Leu Ala Asn Thr Ile Ala Ala Leu His Lys
            1460                1465                1470
Val Gly Leu Lys Val Gln Glu Asp Ile Val Met Asn Gln Met Ile Gly
        1475                1480                1485
Phe Ser Gly Gln Glu Ala Val Thr Val Thr Arg Thr Asn Asn Arg Gly
    1490                1495                1500
Met Gln Ile His Val Asn Gly Gln Thr Tyr Ala Asn Gln Ile Tyr Phe
1505                1510                1515                1520
Ala Tyr Thr Thr Gly Gly Gly Asn Gly Gln Glu Thr Tyr Gly Gly Lys
                1525                1530                1535
Tyr Leu Ala Glu Leu Gln Lys Asn Tyr Pro Asp Leu Phe Thr Thr Lys
            1540                1545                1550
Ala Ile Ser Thr Glu Val Val Pro Asp Pro Thr Val Arg Ile Asn Lys
        1555                1560                1565
Trp Ser Ala Lys Tyr Glu Asn Gly Thr Ser Leu Gln Asn Ile Gly Ile
    1570                1575                1580
Gly Leu Ala Val Lys Leu Ala Asn Gly Asp Tyr Ala Tyr Leu Asn Ser
1585                1590                1595                1600
Gly Asp Asn Lys Ala Phe Asn Thr Leu Leu Pro Thr Ala Ile Ser Leu
                1605                1610                1615
Asn Phe Asn Asn
            1620

<210> SEQ ID NO 8
<211> LENGTH: 1363
<212> TYPE: PRT
<213> ORGANISM: Lactobacillus reuteri DSM 20016

<400> SEQUENCE: 8

Met Asn Leu Pro Thr Ile Pro Asn Thr Asn Val Gln Thr Asp Asn Asn
1               5                   10                  15
Trp Tyr Leu Val Asp Asn Gly Ile Ala Gln Ser Gly Val Gln Gln Trp
            20                  25                  30
Ala Gly Ser Tyr Tyr Phe Asn Pro Ser Thr Tyr Leu Arg Val Asp
        35                  40                  45
Asn Glu Tyr Arg Gln Ser Gln Trp Gly Asp Trp Tyr Met Phe Gly Lys
    50                  55                  60
Asp Gly Arg Ala Val Thr Gly Leu Tyr Asp Tyr Asn Gly Asn Thr Tyr
65                  70                  75                  80
Tyr Ala Asn Pro Thr Thr Tyr Leu Arg Glu Thr Asn Lys Tyr Ile Ser
                85                  90                  95
Thr Ser Lys Gly Asn Met Leu Leu Gly Asn Asp Gly Ala Ala Leu Ser
            100                 105                 110
Gly Ile Gln Ser Val Asn Gly Lys Tyr Tyr Phe Asp Pro Val Thr
        115                 120                 125
His Leu Gln Ala Asn Lys Glu Asn Tyr Val Gln Ser Gln Trp Gly Asp
    130                 135                 140
```

```
Trp Tyr Leu Ile Gly Asn Asp Gly Gln Val Leu Ser Gly Val Gln Gln
145                 150                 155                 160

Trp Ala Gly Thr Tyr Tyr Tyr Phe Asp Pro Thr Thr Tyr Leu Arg Val
            165                 170                 175

Asp Asn Asp Tyr Arg Gln Ser Gln Trp Gly Leu Trp Tyr Met Phe Gly
                180                 185                 190

His Asp Gly Arg Ile Val Thr Lys Val Tyr Pro Trp Ala Gly Thr Tyr
        195                 200                 205

Tyr Tyr Phe Asp Pro Thr Thr Tyr Leu Arg Val Asp Asn Ala Tyr Leu
    210                 215                 220

Gln Ser Gln Trp Gly Asp Trp Tyr Leu Phe Gly Asn Asp Gly Arg Ile
225                 230                 235                 240

Gln Ser Gly Val Gln Arg Trp Ala Gly Thr Tyr Tyr Tyr Phe Asp Pro
            245                 250                 255

Thr Thr Tyr Leu Arg Val Asp Asn Asp Tyr Val Thr Ser Gln Trp Gly
                260                 265                 270

Ser Lys Tyr Met Phe Gly Pro Asp Gly Arg Ile Val Thr Gly Leu Tyr
        275                 280                 285

Lys Trp Ser Lys Asn Asn Gln Leu Tyr Tyr Phe Asp Pro Val Thr Tyr
    290                 295                 300

Leu Ala Val Thr Asn Asn Tyr Ile Lys Ala Asn Asn Gly Asn Trp Tyr
305                 310                 315                 320

Leu Phe Thr Ala Asp Gly Thr Ala Ala Ser Lys Val Ala Pro Trp Ala
            325                 330                 335

Gly Ser Tyr Tyr Tyr Phe Asp Pro Val Thr His Leu Arg Val Asp Asn
                340                 345                 350

Ala Tyr Val Gln Ser Gln Trp Gly Asp Trp Tyr Met Phe Gly Pro Asp
        355                 360                 365

Gly Arg Ile Val Thr Gly Leu Lys Glu Trp Tyr Gly Ser Tyr Tyr Tyr
    370                 375                 380

Phe Asp Pro Thr Thr Tyr Leu Lys Val Thr Asn Lys Trp Ile Asp Asn
385                 390                 395                 400

Lys Tyr Phe Gly Pro Asp Gly Arg Gln Ala Ile Ser Ser Leu Glu Asn
            405                 410                 415

Ile Asn Asn Lys Phe Tyr Cys Phe Asp Gly Asn Gly Gln Ile Ile Arg
                420                 425                 430

Asn Gln Phe Lys Lys Ile Asp Thr His Thr Tyr Tyr Phe Gly Ser Asp
        435                 440                 445

Gly Ala Ala Leu Val Gly Lys Gln Thr Ile Asp Gly Lys Asn Tyr His
450                 455                 460

Phe Ala Ser Asn Gly Gln Leu Leu Gly Asn Leu Tyr Gly Lys Ile Val
465                 470                 475                 480

Asp Gly Lys Phe Asn Ile Tyr Asp Ser Leu Ser Asn Lys Leu Ile Lys
            485                 490                 495

Thr Leu Asp Ser Gly Asp Trp Glu Asn Met Ala Tyr Ser Gln Asp Ser
                500                 505                 510

Ser Ser Ile Asn Asn Thr Asp Gly Tyr Leu Ser Tyr Ser Gly Trp Tyr
        515                 520                 525

Arg Pro Tyr Gly Thr Ser Gln Asp Gly Lys Thr Trp Tyr Lys Thr Thr
    530                 535                 540

Ala Ser Asp Trp Arg Pro Leu Leu Met Tyr Thr Trp Pro Ser Lys Asp
545                 550                 555                 560

Val Glu Ala Lys Phe Ile Lys Tyr Phe Val Asp Asn Gly Tyr Thr Asn
```

```
                565                 570                 575
Thr Asp Tyr Gly Leu Thr Lys Asp Asn Val Thr Asn Leu Ser Gln Asp
                580                 585                 590

Thr Asp Thr Gln Thr Leu Asn Lys Tyr Ala Arg Asn Leu Arg Phe Val
            595                 600                 605

Ile Glu Lys Ser Ile Ala Ala Asn Lys Ser Thr Gly Pro Leu Ala Asn
    610                 615                 620

Asp Ile Asn Lys Phe Met Leu Thr Ile Pro Glu Leu Ser Ala Lys Ser
625                 630                 635                 640

Glu Leu Pro Val Glu Tyr Ser Asn Gly Tyr Val Pro Asp Val Ser Gly
                645                 650                 655

Ser Ile Asp Asn Asn Gln Leu Ile Phe Ile Asn Asn Ser Asp Asn
            660                 665                 670

Gln Ala Lys Gly Asn Thr Ser Tyr Ala Asp Ser Asn Tyr Arg Leu Met
            675                 680                 685

Asn Arg Thr Ile Asn Asn Gln Thr Asn Asn Asp Asn Ser Asp Gln Ser
        690                 695                 700

Pro Glu Leu Leu Val Gly Asn Asp Ile Asp Asn Ser Asn Pro Ala Val
705                 710                 715                 720

Gln Ala Glu Asn Phe Asn Trp Glu Tyr Phe Leu Asn Tyr Gly Lys
                725                 730                 735

Leu Met Lys Tyr Asn Ala Asp Gly Asn Phe Asp Gly Phe Arg Val Asp
            740                 745                 750

Ala Ala Asp Asn Ile Asp Ala Asp Val Leu Asp Gln Leu Gly Gln Leu
            755                 760                 765

Val Asn Asp Met Tyr His Thr Lys Gly Asn Gln Glu Asn Ala Asn Asn
        770                 775                 780

His Leu Val Tyr Asn Glu Gly Tyr His Ser Gly Ala Ala Arg Met Leu
785                 790                 795                 800

Asn Asp Lys Gly Asn Pro Glu Leu Phe Met Asp Ala Gly Tyr Phe Tyr
                805                 810                 815

Thr Leu Glu Asn Val Leu Gly Gln Ala Glu Asn Lys Arg Asp Asn Val
            820                 825                 830

Asn Asn Leu Ile Thr Asn Ser Val Val Asn Arg Ala Asn Asp Ile Thr
        835                 840                 845

Glu Asn Thr Ala Thr Pro Asn Trp Ser Phe Val Thr Asn His Asp Gln
    850                 855                 860

Arg Lys Asn Val Ile Asn Gln Ile Ile Asp Asn His Pro Asn Ile
865                 870                 875                 880

Pro Asp Ile Met Ala Asn Ser Tyr Lys Ser Thr Tyr Ala Gln Lys Ala
                885                 890                 895

Trp Asp Glu Phe Tyr Ala Asp Gln Ala Lys Ala Asp Lys Lys Tyr Ala
            900                 905                 910

Gln Tyr Asn Leu Pro Ala Gln Tyr Ala Leu Leu Leu Ser Asn Lys Asp
            915                 920                 925

Thr Val Pro Gln Val Tyr Tyr Gly Asp Leu Tyr Lys Glu Thr Asp Gln
        930                 935                 940

Tyr Met Lys Thr Lys Ser Met Tyr Tyr Asp Ala Ile Thr Thr Leu Met
945                 950                 955                 960

Lys Ala Arg Gly Glu Phe Val Asn Gly Gly Gln Thr Met Thr Lys Val
                965                 970                 975

Asn Asp Asn Leu Ile Thr Ser Val Arg Tyr Gly Lys Gly Val Val Asp
            980                 985                 990
```

Val Ser Ser Asn Gly Thr Asp Pro Leu Ser Arg Thr Gly Met Ala
    995                 1000                1005

Val Ile Val Gly Asn Asn Pro Ser Met Ser Glu Gln Val Val Ala Ile
1010                1015                1020

Asn Met Gly Leu Ala His Ala Asn Glu Gln Tyr Arg Asn Leu Ile Asp
1025                1030                1035                1040

Ser Thr Ala Asp Gly Leu Thr Tyr Asn Ser Asn Gly Ser Val Asn Pro
                1045                1050                1055

Ser Val Leu Thr Thr Asp Ser Lys Gly Ile Leu Arg Val Thr Val Lys
            1060                1065                1070

Gly Tyr Ser Asn Pro Tyr Val Ser Gly Tyr Leu Ser Val Trp Val Pro
        1075                1080                1085

Leu Ile Asn Gly Thr Gln Asn Ala Arg Thr Ser Ala Gln Glu Val Arg
    1090                1095                1100

Asn Val Pro Gly Lys Val Phe Thr Ser Asn Ala Ala Leu Asp Ser His
1105                1110                1115                1120

Met Ile Tyr Glu Asp Phe Ser Leu Phe Gln Pro Glu Pro Thr Thr Val
                1125                1130                1135

Asn Glu His Ala Tyr Asn Val Ile Lys Asp Asn Val Ala Leu Phe Asn
            1140                1145                1150

Gln Leu Gly Ile Thr Asp Phe Trp Met Ala Pro Ser Tyr Thr Pro Phe
        1155                1160                1165

Asn Thr Ser Arg Tyr Asn Glu Gly Tyr Ala Met Thr Asp Arg Tyr Asn
    1170                1175                1180

Leu Gly Thr Ala Asp Asn Pro Thr Lys Tyr Gly Asn Gly Glu Glu Leu
1185                1190                1195                1200

Ser Asn Ala Ile Ala Ala Leu His Gln Ala Gly Leu Lys Val Gln Glu
                1205                1210                1215

Asp Leu Val Met Asn Gln Met Ile Gly Phe Ser Thr Gln Glu Ala Val
            1220                1225                1230

Thr Val Thr Arg Val Asp Arg Asp Ala Lys Gln Leu Ser Val Asp Gly
        1235                1240                1245

Gln Thr Phe Ala Asp Gln Ile Tyr Phe Gly Tyr Thr Arg Gly Gly Gly
    1250                1255                1260

Gln Gly Gln Gln Asp Tyr Gly Gly Lys Tyr Leu Ala Glu Leu Lys Gln
1265                1270                1275                1280

Lys Tyr Pro Asp Leu Phe Thr Thr Lys Ala Ala Ser Thr Gly Val Ala
                1285                1290                1295

Pro Asp Pro Asn Thr Arg Ile Thr Glu Trp Ser Ala Lys Tyr Glu Asn
            1300                1305                1310

Gly Thr Ser Leu Gln Asn Val Gly Ile Gly Leu Ala Val Lys Met Pro
        1315                1320                1325

Asn Gly Tyr Tyr Ala Tyr Leu Asn Asp Gly Asn Asn Lys Ala Phe Ala
    1330                1335                1340

Thr Thr Leu Pro Asp Ala Ile Ser Ser Ala Asp Tyr Tyr Ala Asn Gln
1345                1350                1355                1360

Glu Asn Ile

<210> SEQ ID NO 9
<211> LENGTH: 1593
<212> TYPE: PRT
<213> ORGANISM: Lactobacillus fermentum

<400> SEQUENCE: 9

```
Met Glu Phe Lys Lys His Phe Lys Leu Tyr Lys Ser Gly Lys Gln Trp
1               5                   10                  15

Cys Ile Ala Ala Val Val Thr Phe Thr Ala Thr Leu Gly Leu Val Ala
                20                  25                  30

Gly Asn Thr Thr Val Asn Ala Asp Thr Leu Thr Thr Gly Gly Ser Thr
            35                  40                  45

Pro Gln Ala Gln Val Asn Gln Glu Lys Gly Ile Thr Asn Thr Ser Gln
50                  55                  60

Pro Ala Ser Asp Gln Gly Lys Thr Ser Asn Thr Gly Asp Val Arg Asn
65                  70                  75                  80

Thr Val Pro Gln Pro Asn Asn Ser Asp Lys Thr Asn Gln Tyr Gln Ala
                85                  90                  95

Asp Thr Leu Thr Thr Gly Gly Ser Thr Pro Gln Ala Gln Val Asn Gln
            100                 105                 110

Glu Lys Gly Ile Thr Asn Thr Ser Gln Pro Ala Ser Asp Gln Gly Lys
            115                 120                 125

Thr Ser Asn Thr Gly Asp Val Arg Asn Thr Val Pro Gln Pro Asn Asn
130                 135                 140

Ser Gly Lys Thr Asn Gln Ser Gln Asn Gly Gln Asp Gln Lys Glu Ser
145                 150                 155                 160

Ala Gly Asn Asp Asn Gly Ser Thr Gly Asn Asn Asp Gln Asn Lys Gly
                165                 170                 175

Gln Gln Thr Thr Asp Trp Gln Lys Asn Ala Asn Asn Gln Trp Val Tyr
            180                 185                 190

Asn Gly Lys Thr Asp Gln Asp Leu Lys Gly Thr Gln Tyr Val Gln Leu
            195                 200                 205

Pro Thr Ile Pro Asp Thr Asn Val Gln Gly Asn Thr Asn Trp Tyr Phe
210                 215                 220

Val Lys Asp Gly Ile Ala Gln Ser Gly Val Gln Gln Trp Ala Gly Thr
225                 230                 235                 240

Tyr Tyr Tyr Phe Asp Pro Thr Thr Tyr Leu Arg Val Asp Asn Asp Tyr
                245                 250                 255

Arg Gln Ser Gln Trp Gly Asp Trp Tyr Leu Phe Gly Asn Asp Gly Arg
            260                 265                 270

Ile Leu Ser Gly Val Gln Gln Trp Ala Gly Thr Tyr Tyr Tyr Phe Asp
            275                 280                 285

Pro Thr Thr Tyr Leu Arg Val Asp Asp Tyr Val Thr Ser Gln Trp
290                 295                 300

Gly Leu Lys Tyr Met Phe Gly Lys Asp Gly Arg Ile Ala Thr Gly Leu
305                 310                 315                 320

Tyr Lys Trp Asp Lys Asn Asn Gln Trp Tyr Tyr Phe Asn Pro Thr Thr
                325                 330                 335

Tyr Leu Ala Val Thr Asn Asn Tyr Ile Gln Ala Asn Asp Gly His Trp
            340                 345                 350

Tyr Leu Phe Thr Ala Asp Gly Thr Ala Ala Ser Arg Val Ala Lys Trp
            355                 360                 365

Ala Gly Thr Tyr Tyr Phe Asp Pro Gln Thr His Leu Arg Val Asp
370                 375                 380

Asp Asn Tyr Val Gln Ser Gln Trp Gly Asp Trp Tyr Met Phe Gly Lys
385                 390                 395                 400

Asp Gly Arg Ile Ala Thr Gly Leu Tyr Lys Trp Asp Lys Asn Asn Gln
            405                 410                 415
```

```
Trp Tyr Tyr Phe Asp Pro Thr Thr Tyr Leu Ala Val Thr Asn Asn Tyr
            420                 425                 430

Ile Gln Ala Asn Asp Gly His Trp Tyr Leu Phe Thr Ala Asp Gly Thr
        435                 440                 445

Ala Ala Ser Arg Val Ala Lys Trp Ala Gly Thr Tyr Tyr Phe Asp
    450                 455                 460

Pro Val Thr His Leu Arg Val Asp Asn Asn Tyr Val Gln Ser Gln Trp
465                 470                 475                 480

Gly Asp Trp Tyr Leu Phe Gly Asn Asp Gly Arg Ile Leu Ser Gly Val
                485                 490                 495

Gln Gln Trp Ala Gly Thr Tyr Tyr Phe Asp Pro Thr Thr Tyr Leu
        500                 505                 510

Arg Val Asp Asp Tyr Val Thr Ser Gln Trp Gly Leu Lys Tyr Met
            515                 520                 525

Phe Gly Lys Asp Gly Arg Ile Ala Thr Gly Leu Tyr Lys Trp Asp Lys
        530                 535                 540

Asn Asn Gln Trp Tyr Tyr Phe Asp Pro Thr Thr Tyr Leu Ala Val Thr
545                 550                 555                 560

Asn Asn Tyr Ile Gln Ala Asn Asp Gly His Trp Tyr Leu Phe Thr Ala
                565                 570                 575

Asp Gly Thr Ala Ala Ser Arg Val Ala Lys Trp Ala Gly Thr Tyr Tyr
            580                 585                 590

Tyr Phe Asp Pro Gln Thr His Leu Arg Val Asp Asp Asn Tyr Val Gln
        595                 600                 605

Ser Gln Trp Gly Asp Trp Tyr Met Phe Gly Lys Asp Gly Arg Ile Ala
    610                 615                 620

Thr Gly Leu Tyr Lys Trp Asp Lys Asn Asn Gln Trp Tyr Tyr Phe Asp
625                 630                 635                 640

Pro Val Thr Tyr Leu Lys Val Thr Asn Lys Trp Val Asp Gly Asn Tyr
                645                 650                 655

Tyr Asp Glu Asp Gly Ala Gln Ala Ile Ser Lys Leu Val Thr Ile Asn
            660                 665                 670

Asn Arg Leu Tyr Tyr Phe Asp Asp Gln Gly Lys Glu Ile Ser Asn Gln
        675                 680                 685

Phe Arg Thr Ile His Gly Asp Lys Tyr Tyr Phe Gly Asn Asp Ser Ala
    690                 695                 700

Ala Val Thr Gly Gln Gln Thr Ile Asp Gly Lys Val Tyr Lys Phe Ser
705                 710                 715                 720

Asn Tyr Gly Tyr Leu Leu Gly Asn Arg Tyr Gly Lys Ile Glu Asn Gly
                725                 730                 735

Lys Leu Asn Ile Tyr Ser Leu Ala Asp His Ser Leu Ile Lys Thr Val
            740                 745                 750

Glu Ala Gly Pro Trp Glu Asn Met Ala Tyr Ser Met Asp Ser Asn Ser
        755                 760                 765

Ile Asn Asn Ile Asp Gly Tyr Ile Ser Tyr Thr Gly Trp Tyr Arg Pro
    770                 775                 780

Tyr Gly Thr Ser Gln Asp Gly Lys Thr Trp Tyr Pro Thr Thr Val Ala
785                 790                 795                 800

Asp Trp Arg Pro Ile Leu Met Tyr Val Trp Pro Ser Lys Asp Val Gln
                805                 810                 815

Val Lys Phe Ile Gln Tyr Phe Val Asn His Gly Tyr Glu Asn Ser Asn
            820                 825                 830

Tyr Gly Leu Thr Ala Gly Ser Val Lys Asp Leu Ser Glu Asn Thr Ala
```

```
            835                 840                 845
Ser Ile Asn Leu Asn Glu Val Ala Gln Asn Leu Arg Tyr Val Ile Glu
    850                 855                 860

Gln His Ile Val Ala Ala Lys Ser Thr Ser Gln Leu Ala Asn Asp Ile
865                 870                 875                 880

Asn Asn Phe Ile Thr Thr Ile Pro Glu Leu Ser Ala Ser Ser Glu Leu
                885                 890                 895

Pro Asp Glu Ser Gly Ser Gly Gln Val Ile Phe Val Asn Asn Asp Asn
            900                 905                 910

Thr Ser Tyr Ala Asp Ser Lys Tyr Arg Leu Met Asn Arg Thr Val Asn
        915                 920                 925

Asn Gln Thr Gly Asn Asp Asn Ser Asp Tyr Cys Pro Glu Phe Val Val
    930                 935                 940

Gly Asn Asp Ile Asp Asn Ser Asn Pro Val Val Gln Ala Glu Asn Leu
945                 950                 955                 960

Asn Trp Glu Tyr Phe Leu Leu Asn Tyr Gly Lys Leu Met Gly Tyr Asn
                965                 970                 975

Gln Asp Gly Asn Phe Asp Gly Phe Arg Ile Asp Ala Ala Asp Asp Met
            980                 985                 990

Asp Ala Asp Val Leu Asp Gln Ile Gly Gln Leu Met Asn Asp Met Tyr
        995                 1000                1005

His Met Lys Gly Asn Pro Gln Asn Ala Asn His Leu Ser Tyr Asn
    1010                1015                1020

Glu Gly Tyr Gly Pro Gly Ala Ala Arg Met Leu Asn Lys Lys Gly Asn
1025                1030                1035                1040

Pro Gln Leu Phe Met Asp Ala Arg Glu Cys Asn Thr Leu Glu Asn Val
                1045                1050                1055

Leu Gly Arg Ala Asn Asn Arg Asp Thr Ile Ser His Leu Val Thr Asp
            1060                1065                1070

Ser Ile Val Asn Arg Gln Asn Asp Val Thr Glu Asn Glu Ala Thr Pro
        1075                1080                1085

Asn Trp Ser Tyr Val Thr Asn His Asp Ile Arg Asn Asn Leu Ile Asn
    1090                1095                1100

Gly Leu Ile Ile Lys Asp His Pro Gly Met Gly Ser Ala Tyr Lys Ala
1105                1110                1115                1120

Glu Tyr Ala Asn Gln Ala Trp Gln Glu Phe Tyr Ala Asp Gln Lys Lys
                1125                1130                1135

Thr Asp Lys Gln Tyr Ala Gln Tyr Asn Val Pro Ala Gln Tyr Ala Ile
            1140                1145                1150

Leu Leu Ser Asn Lys Asp Thr Val Pro Gln Ile Tyr Tyr Gly Asp Leu
        1155                1160                1165

Tyr Asn Glu Thr Ala Gln Tyr Met Gln Glu Lys Ser Ile Tyr Tyr Asp
    1170                1175                1180

Ala Ile Thr Thr Leu Met Lys Ala Arg Lys Gln Phe Val Ser Gly Gly
1185                1190                1195                1200

Gln Thr Met Thr Lys Leu Ser Asp Asn Leu Ile Ala Ser Val Arg Tyr
                1205                1210                1215

Gly Lys Gly Val Ala Asn Ala Asn Ser Glu Gly Thr Asp Ser Leu Ser
            1220                1225                1230

Arg Thr Ser Gly Met Ala Val Ile Val Gly Asn Asn Pro Gln Met Ala
        1235                1240                1245

Glu Gln Thr Ile Ser Ile Asn Met Gly Arg Ala His Ala Asn Glu Gln
    1250                1255                1260
```

Tyr Arg Asn Leu Leu Asp Thr Thr Asp Asn Gly Leu Thr Tyr Asn Ala
1265                1270                1275                1280

Asp Gly Ala Glu Asn Pro Glu Thr Leu Thr Thr Asp Asn Gly Ile
            1285                1290                1295

Leu Lys Val Thr Val Lys Gly Tyr Ser Asn Pro Tyr Val Ser Gly Tyr
1300                1305                1310

Leu Gly Val Trp Val Pro Val Ala Ser Gly Asn Gln Asp Val Thr Thr
            1315                1320                1325

Asn Ala Ala Thr Val Ser Ala Asp Ser Asn Lys Ile Phe Glu Ser Asn
1330                1335                1340

Ala Ala Leu Asp Ser His Met Ile Tyr Glu Asp Phe Ser Met Tyr Gln
1345                1350                1355                1360

Pro Lys Pro Thr Ser Thr Glu Asn His Ala Tyr Asn Ile Ile Ala Gln
            1365                1370                1375

Asn Ala Glu Leu Phe Asn Asn Leu Gly Ile Thr Asp Phe Trp Met Ala
1380                1385                1390

Pro Ala Tyr Thr Gln Ala Gly Thr Ser Arg Tyr Asn Glu Gly Tyr Ser
            1395                1400                1405

Val Ala Asp Arg Tyr Asn Leu Gly Thr Asn Ala Asn Pro Thr Lys Tyr
            1410                1415                1420

Gly Ser Gly Glu Glu Leu Ala Asn Ala Ile Ala Ala Leu His Ser Ala
1425                1430                1435                1440

Gly Leu Lys Val Gln Glu Asp Ile Val Met Asn Gln Met Ile Gly Leu
            1445                1450                1455

Pro Gly Gln Glu Ala Val Thr Val Thr Arg Ala Asp Asn Arg Gly Met
            1460                1465                1470

Gln Thr Tyr Val Asn Gly Lys Thr Tyr Ala Asn Gln Met Tyr Phe Ala
            1475                1480                1485

Tyr Thr Thr Gly Gly Gly Asn Gly Gln Glu Tyr Gly Gly Lys Tyr
            1490                1495                1500

Leu Ser Glu Leu Gln Ser Lys Tyr Pro Asp Leu Phe Thr Thr Arg Ala
1505                1510                1515                1520

Ile Ser Thr Gly Val Ala Pro Asp Pro Thr Thr His Ile Thr Lys Trp
            1525                1530                1535

Ser Ala Lys Tyr Glu Asn Gly Thr Ser Leu Gln Asn Ile Gly Ile Gly
            1540                1545                1550

Leu Ala Val Lys Leu Ala Asn Gly Asp Tyr Ala Tyr Leu Asn Asp Ser
            1555                1560                1565

Asn Asn Lys Ala Phe Asn Thr Thr Leu Pro Glu Thr Met Ser Ser Thr
            1570                1575                1580

Asp Tyr Tyr Ala Asn Ile Glu Asp Asn
1585                1590

<210> SEQ ID NO 10
<211> LENGTH: 893
<212> TYPE: PRT
<213> ORGANISM: Exiguobacterium sibiricum 255-15

<400> SEQUENCE: 10

Met Lys Asn Thr Lys Lys Val Ser Ala Gly Leu Leu Ala Thr Leu Val
1               5                   10                  15

Ala Thr Ser Ser Phe Gly Val Ala Pro Lys Gln Ala Ala Ala Tyr Thr
            20                  25                  30

Ser Gly Glu Lys Leu Asp Asn His Val Ile Phe Gln Ser Phe Ser Leu

```
                35                  40                  45
Tyr Gln Pro Tyr Asp Ser Asn Met Tyr Arg Thr Leu Ala Lys Lys Gly
 50                  55                  60

Asp Leu Leu Asn Ser Trp Gly Val Thr Asp Val Trp Met Pro Pro Ala
 65                  70                  75                  80

Tyr Arg Ser Phe Asp Met Ala Arg Tyr Met Glu Gly Tyr Ala Ile Ala
                 85                  90                  95

Asp Arg Tyr Asp Leu Gly Glu Phe Pro Gln Gly Pro Gly Gly Thr Thr
                100                 105                 110

Ala Thr Lys Tyr Gly Lys Ala Ser His Leu Glu Met Met Val Asp Met
                115                 120                 125

Leu His Asp Asp Asn Ile Lys Val Gln Met Asp Leu Val Pro Asn Gln
130                 135                 140

Met Leu Gly Leu Asn Lys Arg Glu Ala Val Phe Val Arg Arg Ala Thr
145                 150                 155                 160

Ser Ser Gly Glu Leu Phe Thr Asn Pro Tyr Thr Gly Gly Gln Thr Thr
                165                 170                 175

Lys Thr Leu Ala Thr Pro Tyr Leu Ala Tyr Thr Lys Gly Gly Gly Gln
                180                 185                 190

Gly Gln Glu Lys Tyr Gly Tyr Leu Lys Glu Trp Asn Lys Thr Phe Leu
                195                 200                 205

Asn Gly Thr Ser Leu Gln Gly Gln Gly Thr Gly Arg Val Met Thr Asp
210                 215                 220

Lys Asp Gly Lys Pro Tyr Arg Tyr Phe Gly Pro Glu Asn Glu Lys Asn
225                 230                 235                 240

Tyr Leu Pro Glu Trp Leu Ile Glu Ala Ser Lys Thr Gln Asn Leu Asn
                245                 250                 255

Val Val Asp Thr Tyr Leu Ala Ala Asp Gly Trp Tyr Glu Val Ser Pro
                260                 265                 270

Gln Asn Trp Lys Pro Met Leu Ser Gln Tyr Ala Lys Asp Pro Gly Tyr
                275                 280                 285

Leu Ala Tyr Met Lys Glu Asn Gly Phe Glu Thr Lys Glu Ala Leu Leu
290                 295                 300

Ala Ser Ala Asp Asn Gly Thr Ile Ala Lys Leu Thr Glu Glu Tyr Met
305                 310                 315                 320

Lys Thr Gln Ala Thr Tyr Gly Tyr Gly Thr Glu Glu Arg Ser Tyr Gln
                325                 330                 335

Asn Asp Asn Ser Gly Ile Asp Ile Glu Asp Gln Phe Leu Phe Val Asp
                340                 345                 350

Glu Thr Gly Phe Pro Leu Gln Ala Tyr Asn Lys Thr Met Thr Asn Asn
                355                 360                 365

Asp Glu Phe Leu Leu Gly Val Asp Leu Ala Asn Ser Asn Thr Glu Val
                370                 375                 380

Ile Lys Glu Gln Lys Asn Trp Met Lys Trp Met Leu Glu Thr Tyr Lys
385                 390                 395                 400

Phe Asp Gly Phe Arg Ile Asp Ala Ala Ser His Tyr Asp Thr Ala Ile
                405                 410                 415

Leu Lys Ala Glu Ala Gln Val Ala Lys Glu His Phe Gly Lys Lys Glu
                420                 425                 430

His Leu Ser Tyr Ile Glu Ser Tyr Lys Ser Glu Gln Lys Ala Tyr Met
                435                 440                 445

Lys Ala Asn Asn Asp Glu Gln Leu Ile Met Asp Ser Pro Leu Tyr Phe
450                 455                 460
```

```
Thr Met Arg Thr Ala Leu Gly Asn Glu Ala Ser Lys Arg Pro Leu Ser
465                 470                 475                 480

Ala Ile Ala Thr Gly Ser Thr Ile Asn Arg Ala Gly Asn Gly Ser Thr
                    485                 490                 495

Asp Val Ser Ala Asn Trp Ser Phe Val Asn Asn His Asp Gln Glu Lys
                500                 505                 510

Asn Arg Val Asn Gln Ile Met Leu Asp Leu Tyr Gly Ile Lys Thr Gly
                515                 520                 525

Ile Gln Tyr Lys Ala Gly Glu Pro Lys Ser Phe Glu Lys Met Tyr
                530                 535                 540

Asp Lys Asp Thr Glu Lys Gln Ala Leu Gly Ile Tyr Asn Ala Glu Leu
545                 550                 555                 560

Ala Ser Thr Lys Lys Lys Tyr Ser Val Asp Asn Val Val Ser Gln Tyr
                    565                 570                 575

Ala Phe Leu Leu Thr Asn Lys Asp Thr Val Pro Thr Val Tyr Tyr Gly
                580                 585                 590

Asp Leu Tyr Gln Thr Asp Ala Ser Tyr Met Ser Lys Gln Thr Pro Tyr
                595                 600                 605

Tyr Asp Glu Ile Thr Asn Leu Leu Lys Val Arg Lys Gln Tyr Ala Tyr
610                 615                 620

Gly Ala Gln Lys Val Ala Tyr His Thr Thr Asn Thr Ser Lys Val Ala
625                 630                 635                 640

Gly Ser His Leu Ile Ser Ser Val Arg Leu Gly Lys Asp Arg Asn Thr
                    645                 650                 655

Gly Val Ala Thr Val Ile Gly Lys Ser Thr Leu Asn Thr Thr Ile
                660                 665                 670

Lys Val Asp Met Gly Lys Gln His Thr Asn Gln Val Phe Val Asp Ala
                675                 680                 685

Ser Gly Val Thr Gln Thr Lys Leu Val Thr Asp Lys Asn Gly Ile Leu
    690                 695                 700

Thr Val Pro Val Lys Gly Met Arg Thr Ala Glu Val Asn Gly Tyr Leu
705                 710                 715                 720

Gly Val Phe Val Pro Gln Thr Thr Lys Ala Pro Thr Ala Thr Ile Glu
                    725                 730                 735

Lys Ala Ser Val Tyr Gln Gly Lys Gly Ile Asn Leu Lys Thr Lys Val
                740                 745                 750

Leu Asn Thr Ser Ser Thr Val Ser Ser Ile Arg Tyr Gln Val Ala Asp
                755                 760                 765

Thr Ser Lys Ala Thr Val Asp Thr Thr Gly Arg Leu Val Gly Lys Ala
                770                 775                 780

Ser Gly Lys Thr Thr Val Thr Ala Thr Val Thr Leu Lys Asp Gly Phe
785                 790                 795                 800

Val Leu Thr Thr Thr Leu Pro Ile Glu Thr Lys Val Asn Glu Val Lys
                    805                 810                 815

Leu Lys Ala Thr Gln Lys Thr Leu Lys Lys Gly Gln Thr Thr Thr Ile
                820                 825                 830

Gly Tyr Ala Ser Ala Thr Asp Lys Ile Lys Ser Val Ser Tyr Ala Ser
                835                 840                 845

Leu Asn Lys Lys Ile Ala Thr Val Asn Thr Lys Gly Gln Val Lys Ala
            850                 855                 860

Val Thr Lys Gly Thr Thr Ser Ile Arg Val Thr Tyr Thr Thr Val Gly
865                 870                 875                 880
```

Asn Tyr Lys Val Val Lys Thr Phe Lys Val Ile Val Lys
            885                 890

<210> SEQ ID NO 11
<211> LENGTH: 780
<212> TYPE: PRT
<213> ORGANISM: Azotobacter chroococcum

<400> SEQUENCE: 11

Met Arg Ala Ser Pro Ser Gln Phe Phe Ala Ile Ser Leu Leu Ser Ile
1               5                   10                  15

Ala Ile Ser Gly Leu Leu Ser Gly Ala Ala Val Ala Ala Pro Ala Pro
            20                  25                  30

Thr Ala Leu Glu Gln Val Pro Asp Gly Lys Gly Gly Val Lys Trp Gln
        35                  40                  45

Glu Val Thr His Asp Ala Ser Ala Glu Glu Gln Lys Gly Gln Asp
    50                  55                  60

Pro Lys Lys Phe Leu Gly Ile Gln Ala Ile Thr Thr Glu Pro Asp Gly
65                  70                  75                  80

Ser Val Lys Val Glu Met Gly Lys Pro Glu Val Arg Gln Pro Ala Ser
                85                  90                  95

Gly Asp Val Phe Val Ser Asn Glu Lys Leu Asp Glu His Val Ile Phe
            100                 105                 110

Gln Ala Phe Ala Leu Tyr Gln Pro Asn Asp Asn Ala Thr Tyr Lys Ala
        115                 120                 125

Leu Thr Glu Asn Ala Pro Gln Leu Ala Gln Trp Gly Ile Thr Asp Val
    130                 135                 140

Trp Ser Pro Pro Tyr Arg Ala Ala Ser Asp Ser Lys Tyr Gly Glu
145                 150                 155                 160

Gly Tyr Ala Ile Ala Asp Arg Tyr Asp Leu Gly Ala Tyr Asp Lys Gly
                165                 170                 175

Pro Thr Lys Tyr Gly Thr Ala Asp Glu Leu Lys Ala Ala Ile Gly Ala
            180                 185                 190

Leu His Asn Asn Asp Ile Arg Ile Gln Val Asp Val Val Pro Asn Gln
        195                 200                 205

Ile Ile Gly Leu Asn Glu Arg His Val Leu Pro Val Thr Gly Val Asp
    210                 215                 220

Met Tyr Gly Lys Pro Met Asn Pro Phe Leu Asp His Tyr Leu Tyr Ser
225                 230                 235                 240

Thr Tyr Ser Lys Gly Ser Ala Pro Gly Gln Ala Glu His Gly Val Ile
                245                 250                 255

Lys Glu Trp Asp Tyr Phe His Phe His Gly Thr Thr Thr Gln Tyr Gln
            260                 265                 270

Gly Leu Phe Arg Val Leu Ser Asp Ala Asn Ser Thr Leu Tyr Arg Tyr
        275                 280                 285

Leu Gly Pro Asn His Pro Glu Asn Tyr Leu Pro Ala Phe Leu Ala Glu
    290                 295                 300

Ser Asp Ala Ala Lys Tyr Gly Lys Ile Asn Thr Ile Asp Gly Tyr Leu
305                 310                 315                 320

Leu Ala Asp Thr Trp Phe Ala Val Glu Asn Ala Glu Ser Glu Asn Ala
                325                 330                 335

Val Tyr Ala Pro Leu Phe Leu Tyr Tyr Glu Glu Pro Arg Asn Gly Val
            340                 345                 350

Val Glu Gln Thr Phe Met Asp Phe Ala Arg Glu Asn Gly Tyr Thr Gly
        355                 360                 365

```
Ser Asp Glu Asp Ile Arg Ala Thr Met Leu Ala Glu Leu Arg Met Thr
    370                 375                 380

Pro Asn Pro Ile Gly Pro Leu Met Asp Glu Tyr Leu Ala Ala Gln Pro
385                 390                 395                 400

Gly Tyr Ser Lys Lys Ser Glu Asp Asp Ala Lys Val Thr Ala Leu Arg
                405                 410                 415

Tyr Asp Gly Pro Glu Asn Asp Ala Ser His Ile Gly Thr Asn Val Leu
                420                 425                 430

Asp Phe Glu Phe Leu Val Gly Asn Asp Leu Asp Thr Ile Arg Glu Asp
        435                 440                 445

Val Gln Gln Glu Gln Leu Asn Trp Gln Lys Tyr Leu Leu Asp Phe Gly
    450                 455                 460

Phe Asp Gly Phe Arg Ile Asp Ala Ala Ser His Ile Asn Thr Asp Met
465                 470                 475                 480

Leu Arg Asp Glu Val Thr Gln Arg Leu Asn His Phe Ala Gly Glu Asp
                485                 490                 495

Val Asn Glu His Leu Ser Tyr Ile Glu Ser Tyr Val Thr Gln Gln Val
                500                 505                 510

Asp Phe Leu Gln Ser Asn Asn Tyr Gly Gln Met Ala Met Asp Ala Gly
        515                 520                 525

Pro Phe Ser Gly Leu Met Phe Ser Phe Gly Arg Asp Trp Ala Pro Leu
    530                 535                 540

Arg Tyr Ala Phe Glu Ala Ser Leu Ile Asp Arg Val Asn Gly Gly Pro
545                 550                 555                 560

Ala Leu Pro Asn Trp Ser Phe Val Asn Asn His Asp Gln Glu His Asn
                565                 570                 575

Ile Leu Val Thr Val Pro Leu Thr Glu Glu Ala Gly Gly Tyr Glu
                580                 585                 590

Pro Asn Ser Gln Pro Tyr Glu Leu Arg Gln Leu Glu Lys Tyr Asp Ala
                595                 600                 605

Asp Arg Asn Ser Val Glu Lys Gln Trp Ala Pro His Asn Val Pro Ala
    610                 615                 620

Met Tyr Ala Ile Leu Leu Thr Thr Lys Asp Thr Val Pro Thr Val Phe
625                 630                 635                 640

Tyr Gly Asp Met Phe Val Ser Ser Lys Pro Tyr Met Ser Thr Pro Thr
                645                 650                 655

Pro Tyr Arg Asp Asp Ile Val Asn Ile Leu Lys Leu Arg Lys Gln Phe
                660                 665                 670

Ala Lys Gly Glu Gln Val Ile Arg Tyr Glu Asn Ser Asn Thr Gly Ser
                675                 680                 685

Asn Gly Glu Asp Leu Val Ser Asn Ile Arg Leu Gly Asn Asp Arg Lys
    690                 695                 700

Thr Gly Val Ala Val Ala Gly Asn Asn Pro Ala Leu Asp Thr Thr
705                 710                 715                 720

Ile Thr Val Asp Met Gly Ala Gln His Arg Asn Gln Trp Phe Val Asp
                725                 730                 735

Ala Met Gly Tyr Gln Pro Glu Arg Leu Lys Thr Asp Lys Asp Gly Arg
                740                 745                 750

Leu Thr Val Gln Val Lys Gly Thr Gln Asn Val Asp Val Lys Gly Tyr
        755                 760                 765

Leu Ala Ala Trp Val Pro Asp Leu Gln Ala Gln Glu
    770                 775                 780
```

<210> SEQ ID NO 12
<211> LENGTH: 708
<212> TYPE: PRT
<213> ORGANISM: Paenibacillus beijingensis

<400> SEQUENCE: 12

```
Met Lys Val Ser Leu Ser Leu Leu Ala Gly Thr Ala Ile Ala
1               5                   10                  15

Gly Val Ala Pro Ala Asn Ala Ala Glu Ser Asn Ala Lys Gly Phe Val
                20                  25                  30

Ser Asn Ala Glu Leu Asp Lys His Val Ile Phe Gln Ser Phe Ser Leu
            35                  40                  45

Tyr Gln Pro Tyr Glu Lys Asn Met Tyr Asn Ile Leu Gly Lys Asn Ser
        50                  55                  60

Ala Lys Leu Lys Asp Trp Gly Ile Thr Asp Ile Trp Met Pro Pro Ala
65                  70                  75                  80

Tyr Arg Thr Phe Ser Gly Ser Tyr Tyr Gly Glu Gly Tyr Ala Ile Ser
                85                  90                  95

Asp Arg Tyr Asp Leu Gly Glu Phe Pro Asn Gly Leu Asn Gly Glu Arg
            100                 105                 110

Ala Thr Lys Tyr Gly Thr Ser Asp Glu Leu Lys Arg Ala Ile Lys Gln
        115                 120                 125

Leu His Ser Lys Asp Leu Asn Val Gln Val Asp Leu Val Pro Asn Gln
130                 135                 140

Met Met Gly Phe Pro Lys Gln Glu Ile Val Asn Val Thr Ala Val Asp
145                 150                 155                 160

Ser Tyr Gly Asn Glu Ile Asp Pro Ala Phe Lys Asp Lys Leu Val Pro
                165                 170                 175

Leu Tyr Thr Lys Gly Gly Gly Pro Gly Gln Ala Lys Tyr Gly Leu Ile
            180                 185                 190

Lys Glu Trp Ser Ser Lys Tyr Phe Asn Gly Gly Pro Met Gln Met
        195                 200                 205

Gly Ser Met Arg Ile Met Val Asp Ala Glu Gly Lys Pro Tyr Arg Tyr
210                 215                 220

Phe Gly Pro Asp His Gln Asp Asn Tyr Leu Pro Glu Trp Leu Ala Ser
225                 230                 235                 240

Ser Glu Ala Gln Lys Tyr Gly Lys Ile Asn His Ile Asp Asn Tyr Leu
                245                 250                 255

Thr Val Asp Ser Tyr Phe Ala Val Lys Gly Ala Asn Thr Asp Asn Asp
            260                 265                 270

Gln Val Trp Arg Ser Leu Leu Leu Tyr Tyr Val Asp Pro Gln Ala Gly
        275                 280                 285

Ser Ala Asn Glu Ser Tyr Leu Asp Phe Met Arg Lys Asn Gly Phe Glu
290                 295                 300

Gly Ala Thr Asp Asp Glu Val Arg Glu Lys Ile Ile Ala Ala Asp Ser
305                 310                 315                 320

Ala Ala Val Thr Lys Leu Thr Asp Ser Tyr Ile Asn Ala Gln Pro Gly
                325                 330                 335

Tyr Ser Ala Ala Thr Asp Pro Lys Gly Leu His Arg Tyr Asn Asn Gly
            340                 345                 350

Val Asn Gly Asn Val Asn Gln Asn Val Leu Gln Tyr Glu Phe Leu Val
        355                 360                 365

Gly Thr Asp Ile Asp Asn Ser Asn Pro Thr Val Gln Ala Glu Gln Leu
370                 375                 380
```

Asn Trp Val Lys Phe Leu Ile Asp Lys Tyr Gly Phe Asp Gly Phe Arg
385                 390                 395                 400

Ile Asp Ala Ala Ser His Tyr Asn Thr Lys Ile Leu Thr Asp Met Arg
                405                 410                 415

Asp Glu Met Ser Ser Arg Phe Gly Asp Asp Leu Asn Asn His Leu Ser
            420                 425                 430

Tyr Ile Glu Ser Tyr Thr Asp Asn Gln Leu Gly Phe Glu Asn Ser Thr
        435                 440                 445

Gly Asn Gly Gln Leu Val Tyr Asp His Gly Val Phe Gly Ala Leu Arg
    450                 455                 460

Asp Ser Leu Gly Lys Glu His Asn Trp Arg Pro Leu Ser Asp Ile Val
465                 470                 475                 480

Thr Ser Ser Tyr Val Asn Arg Ala Asn Pro Asp Ala Lys Pro Thr Pro
                485                 490                 495

Asn Trp Ser Phe Val Met Asn His Asp Gln Glu His Asn Gly Ile Lys
            500                 505                 510

Gly Ile Pro Leu Thr Glu Glu Ala Gly Gly Thr Lys Lys Asn Thr
        515                 520                 525

Val Asp Tyr Glu Lys Lys Gln Phe Glu Lys Tyr Ala Asp Met Val
530                 535                 540

Asn Ala Asp Lys Lys Tyr Ala Asn Tyr Asn Val Pro Ser Gln Tyr Ala
545                 550                 555                 560

Tyr Leu Leu Thr Asn Lys Asp Thr Val Pro Thr Val Tyr Tyr Gly Asp
                565                 570                 575

Met Phe Lys Ser Thr Ala Ser Tyr Met Ser Glu Lys Thr Gln Tyr Phe
            580                 585                 590

Glu Pro Ile Val Lys Leu Leu Gln Ala Arg Gln Lys Tyr Val Ser Gly
        595                 600                 605

Asp Gln Lys Ile Thr Tyr Tyr Asn Ser Asn Thr Ser Trp Ser Ala Gly
    610                 615                 620

Trp Asp Leu Leu Ala Ser Val Arg Phe Gly Thr Ser Arg Asp Thr Gly
625                 630                 635                 640

Val Ala Thr Val Ile Gly Ser Asn Pro Asn Thr Gln Glu Leu Ile Ser
                645                 650                 655

Val Asp Met Gly Lys Leu His Ala Asn Gln Thr Phe Glu Asp Val Met
            660                 665                 670

Gly Phe Asn Thr Gln Lys Leu Thr Thr Asp Glu Asn Gly Val Leu Thr
        675                 680                 685

Val Pro Val Lys Gly Val Ser Asn Pro Leu Val His Gly Tyr Leu Gly
    690                 695                 700

Val Trp Val Pro
705

<210> SEQ ID NO 13
<211> LENGTH: 1772
<212> TYPE: PRT
<213> ORGANISM: Lactobacillus reuteri 180 (Gtf180)

<400> SEQUENCE: 13

Met Glu Ile Lys Lys His Phe Lys Leu Tyr Lys Ser Gly Lys Gln Trp
1               5                   10                  15

Val Thr Ala Ala Val Ala Thr Val Ala Val Ser Thr Ala Leu Leu Tyr
            20                  25                  30

Gly Gly Val Ala His Ala Asp Gln Gln Val Gln Ser Ser Thr Thr Gln

```
                35                  40                  45
Glu Gln Thr Ser Thr Val Asn Ala Asp Thr Thr Lys Thr Val Asn Leu
 50                  55                  60

Asp Thr Asn Thr Asp Gln Pro Ala Gln Thr Thr Asp Lys Asn Gln Val
 65                  70                  75                  80

Ala Asn Asp Thr Thr Asn Gln Ser Lys Thr Asp Ser Thr Ser Thr
                 85                  90                  95

Thr Val Lys Asn Pro Thr Phe Ile Pro Val Ser Thr Leu Ser Ser Ser
                100                 105                 110

Asp Asn Glu Lys Gln Ser Gln Asn Tyr Asn Lys Pro Asp Asn Gly Asn
                115                 120                 125

Tyr Gly Asn Val Asp Ala Ala Tyr Phe Asn Asn Gln Leu His Ile
                130                 135                 140

Ser Gly Trp His Ala Thr Asn Ala Ser Gln Gly Thr Asp Ser Arg Gln
145                 150                 155                 160

Val Ile Val Arg Asp Ile Thr Thr Lys Thr Glu Leu Gly Arg Thr Asn
                165                 170                 175

Val Thr Asn Asn Val Leu Arg Pro Asp Val Lys Asn Val His Asn Val
                180                 185                 190

Tyr Asn Ala Asp Asn Ser Gly Phe Asp Val Asn Ile Asn Ile Asp Phe
                195                 200                 205

Ser Lys Met Lys Asp Tyr Arg Asp Ser Ile Glu Ile Val Ser Arg Tyr
210                 215                 220

Ser Gly Asn Gly Lys Ser Val Asp Trp Trp Ser Gln Pro Ile Thr Phe
225                 230                 235                 240

Asp Lys Asn Asn Tyr Ala Tyr Leu Asp Thr Phe Glu Val Lys Asn Gly
                245                 250                 255

Glu Leu His Ala Thr Gly Trp Asn Ala Thr Asn Lys Ala Ile Asn Tyr
                260                 265                 270

Asn His His Phe Val Ile Leu Phe Asp Arg Thr Asn Gly Lys Glu Val
                275                 280                 285

Thr Arg Gln Glu Val Arg Asp Gly Gln Ser Arg Pro Asp Val Ala Lys
290                 295                 300

Val Tyr Pro Gln Val Val Gly Ala Asn Asn Ser Gly Phe Asp Val Thr
305                 310                 315                 320

Phe Asn Ile Gly Asp Leu Asp Tyr Thr His Gln Tyr Gln Ile Leu Ser
                325                 330                 335

Arg Tyr Ser Asn Ala Asp Asn Gly Glu Gly Asp Tyr Val Thr Tyr Trp
                340                 345                 350

Phe Ala Pro Gln Ser Ile Ala Pro Ala Asn Gln Ser Asn Gln Gly Tyr
                355                 360                 365

Leu Asp Ser Phe Asp Ile Ser Lys Asn Gly Glu Val Thr Val Thr Gly
                370                 375                 380

Trp Asn Ala Thr Asp Leu Ser Glu Leu Gln Thr Asn His Tyr Val Ile
385                 390                 395                 400

Leu Phe Asp Gln Thr Ala Gly Gln Gln Val Ala Ser Ala Lys Val Asp
                405                 410                 415

Leu Ile Ser Arg Pro Asp Val Ala Lys Ala Tyr Pro Val Lys Thr
                420                 425                 430

Ala Glu Thr Ser Gly Phe Lys Val Thr Phe Lys Val Ser Asn Leu Gln
                435                 440                 445

Pro Gly His Gln Tyr Ser Val Val Ser Arg Phe Ser Ala Asp Glu Asn
                450                 455                 460
```

```
Gly Asn Gly Asn Asp Lys Arg His Thr Asp Tyr Trp Tyr Ser Pro Val
465                 470                 475                 480

Thr Leu Asn Gln Thr Ala Ser Asn Ile Asp Thr Ile Thr Met Thr Ser
            485                 490                 495

Asn Gly Leu His Ile Thr Gly Trp Met Ala Ser Asp Asn Ser Ile Asn
        500                 505                 510

Glu Ala Thr Pro Tyr Ala Ile Ile Leu Asn Asn Gly Arg Glu Val Thr
        515                 520                 525

Arg Gln Lys Leu Thr Leu Ile Ala Arg Pro Asp Val Ala Ala Val Tyr
530                 535                 540

Pro Ser Leu Tyr Asn Ser Ala Val Ser Gly Phe Asp Thr Thr Ile Lys
545                 550                 555                 560

Leu Thr Asn Ala Gln Tyr Gln Ala Leu Asn Gly Gln Leu Gln Val Leu
            565                 570                 575

Leu Arg Phe Ser Lys Ala Val Asp Gly Asn Pro Asn Gly Thr Asn Thr
            580                 585                 590

Val Thr Asp Gln Phe Ser Lys Asn Tyr Ala Thr Thr Gly Gly Asn Phe
        595                 600                 605

Asp Tyr Val Lys Val Asn Gly Asn Gln Ile Glu Phe Ser Gly Trp His
        610                 615                 620

Ala Thr Asn Gln Ser Asn Asp Lys Asn Ser Gln Trp Ile Ile Val Leu
625                 630                 635                 640

Val Asn Gly Lys Glu Val Lys Arg Gln Leu Val Asn Asp Thr Lys Asp
            645                 650                 655

Gly Ala Ala Gly Phe Asn Arg Asn Asp Val Tyr Lys Val Asn Pro Ala
            660                 665                 670

Ile Glu Asn Ser Ile Met Ser Gly Phe Gln Gly Ile Ile Thr Leu Pro
            675                 680                 685

Val Thr Val Lys Asp Glu Asn Val Gln Leu Val His Arg Phe Ser Asn
        690                 695                 700

Asp Ala Lys Thr Gly Glu Gly Asn Tyr Val Asp Phe Trp Ser Glu Val
705                 710                 715                 720

Met Ser Val Lys Asp Ser Phe Gln Lys Gly Asn Gly Pro Leu Asn Gln
            725                 730                 735

Phe Gly Leu Gln Thr Ile Asn Gly Gln Gln Tyr Tyr Ile Asp Pro Thr
            740                 745                 750

Thr Gly Gln Pro Arg Lys Asn Phe Leu Leu Gln Asn Gly Asn Asp Trp
            755                 760                 765

Ile Tyr Phe Asp Lys Asp Thr Gly Ala Gly Thr Asn Ala Leu Lys Leu
            770                 775                 780

Gln Phe Asp Lys Gly Thr Ile Ser Ala Asp Glu Gln Tyr Arg Arg Gly
785                 790                 795                 800

Asn Glu Ala Tyr Ser Tyr Asp Asp Lys Ser Ile Glu Asn Val Asn Gly
            805                 810                 815

Tyr Leu Thr Ala Asp Thr Trp Tyr Arg Pro Lys Gln Ile Leu Lys Asp
            820                 825                 830

Gly Thr Thr Trp Thr Asp Ser Lys Glu Thr Asp Met Arg Pro Ile Leu
            835                 840                 845

Met Val Trp Trp Pro Asn Thr Val Thr Gln Ala Tyr Tyr Leu Asn Tyr
            850                 855                 860

Met Lys Gln Tyr Gly Asn Leu Leu Pro Ala Ser Leu Pro Ser Phe Ser
865                 870                 875                 880
```

-continued

Thr Asp Ala Asp Ser Ala Glu Leu Asn His Tyr Ser Glu Leu Val Gln
                885                 890                 895

Gln Asn Ile Glu Lys Arg Ile Ser Glu Thr Gly Ser Thr Asp Trp Leu
            900                 905                 910

Arg Thr Leu Met His Glu Phe Val Thr Lys Asn Ser Met Trp Asn Lys
        915                 920                 925

Asp Ser Glu Asn Val Asp Tyr Gly Gly Leu Gln Leu Gln Gly Gly Phe
    930                 935                 940

Leu Lys Tyr Val Asn Ser Asp Leu Thr Lys Tyr Ala Asn Ser Asp Trp
945                 950                 955                 960

Arg Leu Met Asn Arg Thr Ala Thr Asn Ile Asp Gly Lys Asn Tyr Gly
                965                 970                 975

Gly Ala Glu Phe Leu Leu Ala Asn Asp Ile Asp Asn Ser Asn Pro Val
            980                 985                 990

Val Gln Ala Glu Glu Leu Asn Trp Leu Tyr Tyr Leu Met Asn Phe Gly
        995                 1000                1005

Thr Ile Thr Gly Asn Asn Pro Glu Ala Asn Phe Asp Gly Ile Arg Val
    1010                1015                1020

Asp Ala Val Asp Asn Val Asp Val Asp Leu Leu Ser Ile Ala Arg Asp
1025                1030                1035                1040

Tyr Phe Asn Ala Ala Tyr Asn Met Glu Gln Ser Asp Ala Ser Ala Asn
                1045                1050                1055

Lys His Ile Asn Ile Leu Glu Asp Trp Gly Trp Asp Pro Ala Tyr
            1060                1065                1070

Val Asn Lys Ile Gly Asn Pro Gln Leu Thr Met Asp Asp Arg Leu Arg
            1075                1080                1085

Asn Ala Ile Met Asp Thr Leu Ser Gly Ala Pro Asp Lys Asn Gln Ala
            1090                1095                1100

Leu Asn Lys Leu Ile Thr Gln Ser Leu Val Asn Arg Ala Asn Asp Asn
1105                1110                1115                1120

Thr Glu Asn Ala Val Ile Pro Ser Tyr Asn Phe Val Arg Ala His Asp
                1125                1130                1135

Ser Asn Ala Gln Asp Gln Ile Arg Gln Ala Ile Gln Ala Ala Thr Gly
            1140                1145                1150

Lys Pro Tyr Gly Glu Phe Asn Leu Asp Asp Glu Lys Lys Gly Met Glu
        1155                1160                1165

Ala Tyr Ile Asn Asp Gln Asn Ser Thr Asn Lys Lys Trp Asn Leu Tyr
    1170                1175                1180

Asn Met Pro Ser Ala Tyr Thr Ile Leu Leu Thr Asn Lys Asp Ser Val
1185                1190                1195                1200

Pro Arg Val Tyr Tyr Gly Asp Leu Tyr Gln Asp Gly Gly Gln Tyr Met
                1205                1210                1215

Glu His Lys Thr Arg Tyr Phe Asp Thr Ile Thr Asn Leu Leu Lys Thr
            1220                1225                1230

Arg Val Lys Tyr Val Ala Gly Gly Gln Thr Met Ser Val Asp Lys Asn
        1235                1240                1245

Gly Ile Leu Thr Asn Val Arg Phe Gly Lys Gly Ala Met Asn Ala Thr
    1250                1255                1260

Asp Thr Gly Thr Asp Glu Thr Arg Thr Glu Gly Ile Gly Val Val Ile
1265                1270                1275                1280

Ser Asn Asn Thr Asn Leu Lys Leu Asn Asp Gly Glu Ser Val Val Leu
                1285                1290                1295

His Met Gly Ala Ala His Lys Asn Gln Lys Tyr Arg Ala Val Ile Leu

-continued

```
                1300                1305                1310
Thr Thr Glu Asp Gly Val Lys Asn Tyr Thr Asn Asp Thr Asp Ala Pro
        1315                1320                1325
Val Ala Tyr Thr Asp Ala Asn Gly Asp Leu His Phe Thr Asn Thr Asn
    1330                1335                1340
Leu Asp Gly Gln Gln Tyr Thr Ala Val Arg Gly Tyr Ala Asn Pro Asp
1345                1350                1355                1360
Val Thr Gly Tyr Leu Ala Val Trp Val Pro Ala Gly Ala Ala Asp Asp
            1365                1370                1375
Gln Asp Ala Arg Thr Ala Pro Ser Asp Glu Ala His Thr Thr Lys Thr
        1380                1385                1390
Ala Tyr Arg Ser Asn Ala Ala Leu Asp Ser Asn Val Ile Tyr Glu Gly
    1395                1400                1405
Phe Ser Asn Phe Ile Tyr Trp Pro Thr Thr Glu Ser Glu Arg Thr Asn
        1410                1415                1420
Val Arg Ile Ala Gln Asn Ala Asp Leu Phe Lys Ser Trp Gly Ile Thr
1425                1430                1435                1440
Thr Phe Glu Leu Ala Pro Gln Tyr Asn Ser Ser Lys Asp Gly Thr Phe
            1445                1450                1455
Leu Asp Ser Ile Ile Asp Asn Gly Tyr Ala Phe Thr Asp Arg Tyr Asp
        1460                1465                1470
Leu Gly Met Ser Thr Pro Asn Lys Tyr Gly Ser Asp Glu Asp Leu Arg
    1475                1480                1485
Asn Ala Leu Gln Ala Leu His Lys Ala Gly Leu Gln Ala Ile Ala Asp
        1490                1495                1500
Trp Val Pro Asp Gln Ile Tyr Asn Leu Pro Gly Lys Glu Ala Val Thr
1505                1510                1515                1520
Val Thr Arg Ser Asp Asp His Gly Thr Thr Trp Glu Val Ser Pro Ile
            1525                1530                1535
Lys Asn Val Val Tyr Ile Thr Asn Thr Ile Gly Gly Gly Glu Tyr Gln
        1540                1545                1550
Lys Lys Tyr Gly Gly Glu Phe Leu Asp Thr Leu Gln Lys Glu Tyr Pro
    1555                1560                1565
Gln Leu Phe Ser Gln Val Tyr Pro Val Thr Gln Thr Thr Ile Asp Pro
1570                1575                1580
Ser Val Lys Ile Lys Glu Trp Ser Ala Lys Tyr Phe Asn Gly Thr Asn
1585                1590                1595                1600
Ile Leu His Arg Gly Ala Gly Tyr Val Leu Arg Ser Asn Asp Gly Lys
            1605                1610                1615
Tyr Tyr Asn Leu Gly Thr Ser Thr Gln Gln Phe Leu Pro Ser Gln Leu
        1620                1625                1630
Ser Val Gln Asp Asn Glu Gly Tyr Gly Phe Val Lys Glu Gly Asn Asn
    1635                1640                1645
Tyr His Tyr Tyr Asp Glu Asn Lys Gln Met Val Lys Asp Ala Phe Ile
        1650                1655                1660
Gln Asp Ser Val Gly Asn Trp Tyr Tyr Phe Asp Lys Asn Gly Asn Met
1665                1670                1675                1680
Val Ala Asn Gln Ser Pro Val Glu Ile Ser Ser Asn Gly Ala Ser Gly
            1685                1690                1695
Thr Tyr Leu Phe Leu Asn Asn Gly Thr Ser Phe Arg Ser Gly Leu Val
        1700                1705                1710
Lys Thr Asp Ala Gly Thr Tyr Tyr Tyr Asp Gly Asp Gly Arg Met Val
    1715                1720                1725
```

```
Arg Asn Gln Thr Val Ser Asp Gly Ala Met Thr Tyr Val Leu Asp Glu
    1730            1735                1740

Asn Gly Lys Leu Val Ser Glu Ser Phe Asp Ser Ser Ala Thr Glu Ala
1745                1750                1755                1760

His Pro Leu Lys Pro Gly Asp Leu Asn Gly Gln Lys
            1765                1770

<210> SEQ ID NO 14
<211> LENGTH: 1781
<212> TYPE: PRT
<213> ORGANISM: Lactobacillus reuteri 121 (GtfA)

<400> SEQUENCE: 14

Met Glu Ile Lys Lys His Phe Lys Leu Tyr Lys Ser Gly Lys Gln Trp
1               5                   10                  15

Val Thr Ala Ala Val Ala Thr Val Ala Val Ser Thr Ala Leu Leu Tyr
                20                  25                  30

Gly Gly Val Ala His Ala Asp Gln Gln Val Gln Gln Ala Ser Thr Thr
        35                  40                  45

Gln Asp Gln Thr Ser Thr Val Asn Asn Asp Thr Asp Lys Thr Val Ala
50                  55                  60

Leu Asp Thr Asn Thr Asp Gln Ser Ala Gln Thr Thr Asp Lys Lys Gln
65                  70                  75                  80

Val Val Ser Asn Thr Asn Gln Ser Lys Thr Asp Asp Thr Ser Thr Ala
                85                  90                  95

Asp Lys Asn Ser Thr Ser Thr Pro Val Ser Val Leu Pro Ser Asn Asn
            100                 105                 110

Thr Glu Lys Gln Ala Lys Asn Tyr Asn Glu Gln Asp Lys Gly Asn Tyr
        115                 120                 125

Gly Asn Ile Asp Thr Ala Tyr Phe Ser Asn Asn Gln Leu His Val Ser
130                 135                 140

Gly Trp Asn Ala Thr Asn Ala Ser Gln Gly Thr Asn Ser Arg Gln Ile
145                 150                 155                 160

Ile Val Arg Asp Ile Thr Thr Asn Asn Glu Leu Gly Arg Thr Asp Val
                165                 170                 175

Thr Asn Asn Val Ala Arg Pro Asp Val Lys Asn Val His Asn Val Tyr
            180                 185                 190

Asn Ala Asp Asn Ser Gly Phe Asp Val Asn Val Asn Ile Asp Phe Ser
        195                 200                 205

Lys Met Lys Asp Tyr Arg Asp Ser Ile Glu Ile Val Ser Arg Tyr Ser
210                 215                 220

Gly Asn Gly Lys Ser Val Asp Trp Trp Ser Gln Pro Ile Thr Phe Asp
225                 230                 235                 240

Lys Asn Asn Tyr Ala Tyr Leu Asp Thr Phe Glu Val Lys Asn Gly Glu
                245                 250                 255

Leu His Ala Thr Gly Trp Asn Ala Thr Asn Ser Ala Ile Asn Tyr Asn
            260                 265                 270

His His Phe Val Ile Leu Phe Asp Gln Thr Asn Gly Lys Glu Val Ala
        275                 280                 285

Arg Gln Glu Val Arg Glu Gly Gln Ser Arg Pro Asp Val Ala Lys Val
        290                 295                 300

Tyr Pro Gln Val Val Gly Ala Ala Asn Ser Gly Phe Asn Val Thr Phe
305                 310                 315                 320

Asn Ile Ser Asp Leu Asp Tyr Thr His Gln Tyr Gln Val Leu Ser Arg
```

-continued

```
                325                 330                 335
Tyr Ser Asn Ser Asp Asn Gly Glu Gly Asp Asn Val Thr Tyr Trp Phe
                    340                 345                 350
Asn Pro Gln Ser Ile Ala Pro Ala Asn Gln Ser Asn Gln Gly Tyr Leu
                    355                 360                 365
Asp Ser Phe Asp Ile Ser Lys Asn Gly Glu Val Thr Val Thr Gly Trp
                    370                 375                 380
Asn Ala Thr Asp Leu Ser Glu Leu Gln Asn Asn His Tyr Val Ile Leu
385                 390                 395                 400
Phe Asp Gln Thr Ala Gly Lys Gln Val Ala Ser Ala Lys Ala Asp Leu
                    405                 410                 415
Ile Ser Arg Pro Asp Val Ala Lys Ala Tyr Pro Val Lys Thr Ala
                    420                 425                 430
Thr Asn Ser Gly Phe Lys Val Thr Phe Lys Val Asn Asn Leu Gln Pro
                    435                 440                 445
Gly His Gln Tyr Ser Val Val Ser Arg Phe Ser Ala Asp Glu Asn Gly
                    450                 455                 460
Asn Gly Asn Asp Lys Arg His Thr Asp Tyr Trp Phe Ser Pro Val Ile
465                 470                 475                 480
Leu Asn Gln Thr Ala Ser Asn Ile Asp Thr Ile Thr Met Thr Ser Asn
                    485                 490                 495
Gly Leu His Ile Ala Gly Trp Met Ala Ser Asp Asn Ser Ile Asn Glu
                    500                 505                 510
Thr Thr Pro Tyr Ala Ile Ile Leu Asn Asn Gly Lys Glu Val Thr Arg
                    515                 520                 525
Gln Lys Met Ser Leu Thr Ala Arg Pro Asp Val Ala Ala Val Tyr Pro
                    530                 535                 540
Ser Leu Tyr Asn Ser Ala Val Ser Gly Phe Asp Thr Thr Ile Lys Leu
545                 550                 555                 560
Thr Asn Asp Gln Tyr Gln Ala Leu Asn Gly Gln Leu Gln Val Leu Leu
                    565                 570                 575
Arg Phe Ser Lys Ala Ala Asp Gly Asn Pro Ser Gly Asp Asn Thr Val
                    580                 585                 590
Thr Asp Gln Phe Ser Lys Asn Tyr Ala Thr Thr Gly Asn Phe Asp
                    595                 600                 605
Tyr Val Lys Val Asn Gly Asn Gln Val Glu Phe Ser Gly Trp His Ala
                    610                 615                 620
Thr Asn Gln Ser Asn Asp Lys Asp Ser Gln Trp Ile Ile Val Leu Val
625                 630                 635                 640
Asn Gly Lys Glu Val Lys Arg Gln Leu Val Asn Asp Thr Lys Glu Gly
                    645                 650                 655
Ala Ala Gly Phe Asn Arg Asn Asp Val Tyr Lys Val Asn Pro Ala Ile
                    660                 665                 670
Glu Asn Ser Ser Met Ser Gly Phe Gln Gly Ile Ile Thr Leu Pro Val
                    675                 680                 685
Thr Val Lys Asn Glu Asn Val Gln Leu Val His Arg Phe Ser Asn Asp
                    690                 695                 700
Val Lys Thr Gly Glu Gly Asn Tyr Val Asp Phe Trp Ser Glu Leu Met
705                 710                 715                 720
Pro Val Lys Asp Ser Phe Gln Lys Gly Asn Gly Pro Leu Lys Gln Phe
                    725                 730                 735
Gly Leu Gln Thr Ile Asn Gly Gln Gln Tyr Tyr Ile Asp Pro Thr Thr
                    740                 745                 750
```

-continued

Gly Gln Pro Arg Lys Asn Phe Leu Leu Gln Ser Gly Asn Asn Trp Ile
            755                 760                 765

Tyr Phe Asp Ser Asp Thr Gly Val Gly Thr Asn Ala Leu Glu Leu Gln
770                 775                 780

Phe Ala Lys Gly Thr Val Ser Ser Asn Glu Gln Tyr Arg Asn Gly Asn
785                 790                 795                 800

Ala Ala Tyr Ser Tyr Asp Asp Lys Ser Ile Glu Asn Val Asn Gly Tyr
            805                 810                 815

Leu Thr Ala Asp Thr Trp Tyr Arg Pro Lys Gln Ile Leu Lys Asp Gly
            820                 825                 830

Thr Thr Trp Thr Asp Ser Lys Glu Thr Asp Met Arg Pro Ile Leu Met
            835                 840                 845

Val Trp Trp Pro Asn Thr Leu Thr Gln Ala Tyr Tyr Leu Asn Tyr Met
850                 855                 860

Lys Gln His Gly Asn Leu Leu Pro Ser Ala Leu Pro Phe Phe Asn Ala
865                 870                 875                 880

Asp Ala Asp Pro Ala Glu Leu Asn His Tyr Ser Glu Ile Val Gln Gln
            885                 890                 895

Asn Ile Glu Lys Arg Ile Ser Thr Gly Asn Thr Asp Trp Leu Arg
            900                 905                 910

Thr Leu Met His Asp Phe Val Thr Asn Asn Pro Met Trp Asn Lys Asp
            915                 920                 925

Ser Glu Asn Val Asn Phe Ser Gly Ile Gln Phe Gln Gly Gly Phe Leu
930                 935                 940

Lys Tyr Glu Asn Ser Asp Leu Thr Pro Tyr Ala Asn Ser Asp Tyr Arg
945                 950                 955                 960

Leu Leu Gly Arg Met Pro Ile Asn Ile Lys Asp Gln Thr Tyr Arg Gly
            965                 970                 975

Gln Glu Phe Leu Leu Ala Asn Asp Ile Asp Asn Ser Asn Pro Val Val
            980                 985                 990

Gln Ala Glu Gln Leu Asn Trp Leu Tyr Tyr Leu Leu Asn Phe Gly Thr
            995                 1000                1005

Ile Thr Ala Asn Asn Asp Gln Ala Asn Phe Asp Ser Val Arg Val Asp
    1010                1015                1020

Ala Pro Asp Asn Ile Asp Ala Asp Leu Met Asn Ile Ala Gln Asp Tyr
1025                1030                1035                1040

Phe Asn Ala Ala Tyr Gly Met Asp Ser Asp Ala Val Ser Asn Lys His
                1045                1050                1055

Ile Asn Ile Leu Glu Asp Trp Asn His Ala Asp Pro Glu Tyr Phe Asn
                1060                1065                1070

Lys Ile Gly Asn Pro Gln Leu Thr Met Asp Asp Thr Ile Lys Asn Ser
            1075                1080                1085

Leu Asn His Gly Leu Ser Asp Ala Thr Asn Arg Trp Gly Leu Asp Ala
    1090                1095                1100

Ile Val His Gln Ser Leu Ala Asp Arg Glu Asn Asn Ser Thr Glu Asn
1105                1110                1115                1120

Val Val Ile Pro Asn Tyr Ser Phe Val Arg Ala His Asp Asn Asn Ser
                1125                1130                1135

Gln Asp Gln Ile Gln Asn Ala Ile Arg Asp Val Thr Gly Lys Asp Tyr
            1140                1145                1150

His Thr Phe Thr Phe Glu Asp Glu Gln Lys Gly Ile Asp Ala Tyr Ile
    1155                1160                1165

-continued

```
Gln Asp Gln Asn Ser Thr Val Lys Lys Tyr Asn Leu Tyr Asn Ile Pro
    1170                1175                1180

Ala Ser Tyr Ala Ile Leu Leu Thr Asn Lys Asp Thr Ile Pro Arg Val
1185                1190                1195                1200

Tyr Tyr Gly Asp Leu Tyr Thr Asp Gly Gly Gln Tyr Met Glu His Gln
                1205                1210                1215

Thr Arg Tyr Tyr Asp Thr Leu Thr Asn Leu Leu Lys Ser Arg Val Lys
        1220                1225                1230

Tyr Val Ala Gly Gly Gln Ser Met Gln Thr Met Ser Val Gly Gly Asn
                1235                1240                1245

Asn Asn Ile Leu Thr Ser Val Arg Tyr Gly Lys Gly Ala Met Thr Ala
        1250                1255                1260

Thr Asp Thr Gly Thr Asp Glu Thr Arg Thr Gln Gly Ile Gly Val Val
1265                1270                1275                1280

Val Ser Asn Thr Pro Asn Leu Lys Leu Gly Ala Asn Asp Lys Val Val
                1285                1290                1295

Leu His Met Gly Ala Ala His Lys Asn Gln Gln Tyr Arg Ala Ala Val
        1300                1305                1310

Leu Thr Thr Thr Asp Gly Val Ile Asn Tyr Thr Ser Asp Gln Gly Ala
        1315                1320                1325

Pro Val Ala Met Thr Asp Glu Asn Gly Asp Leu Tyr Leu Ser Ser His
        1330                1335                1340

Asn Leu Val Val Asn Gly Lys Glu Glu Ala Asp Thr Ala Val Gln Gly
1345                1350                1355                1360

Tyr Ala Asn Pro Asp Val Ser Gly Tyr Leu Ala Val Trp Val Pro Val
                1365                1370                1375

Gly Ala Ser Asp Asn Gln Asp Ala Arg Thr Ala Pro Ser Thr Glu Lys
        1380                1385                1390

Asn Ser Gly Asn Ser Ala Tyr Arg Thr Asn Ala Ala Phe Asp Ser Asn
        1395                1400                1405

Val Ile Phe Glu Ala Phe Ser Asn Phe Val Tyr Thr Pro Thr Lys Glu
        1410                1415                1420

Ser Glu Arg Ala Asn Val Arg Ile Ala Gln Asn Ala Asp Phe Phe Ala
1425                1430                1435                1440

Ser Leu Gly Phe Thr Ser Phe Glu Met Ala Pro Gln Tyr Asn Ser Ser
                1445                1450                1455

Lys Asp Arg Thr Phe Leu Asp Ser Thr Ile Asp Asn Gly Tyr Ala Phe
        1460                1465                1470

Thr Asp Arg Tyr Asp Leu Gly Met Ser Glu Pro Asn Lys Tyr Gly Thr
        1475                1480                1485

Asp Glu Asp Leu Arg Asn Ala Ile Gln Ala Leu His Lys Ala Gly Leu
        1490                1495                1500

Gln Val Met Ala Asp Trp Val Pro Asp Gln Ile Tyr Asn Leu Pro Gly
1505                1510                1515                1520

Lys Glu Val Ala Thr Val Thr Arg Val Asp Asp Arg Gly Asn Val Trp
                1525                1530                1535

Lys Asp Ala Ile Ile Asn Asn Asn Leu Tyr Val Val Asn Thr Ile Gly
        1540                1545                1550

Gly Gly Glu Tyr Gln Lys Lys Tyr Gly Gly Ala Phe Leu Asp Lys Leu
        1555                1560                1565

Gln Lys Leu Tyr Pro Glu Ile Phe Thr Lys Lys Gln Val Ser Thr Gly
        1570                1575                1580

Val Ala Ile Asp Pro Ser Gln Lys Ile Thr Glu Trp Ser Ala Lys Tyr
```

```
                  1585                1590                1595                1600
       Phe Asn Gly Thr Asn Ile Leu His Arg Gly Ser Gly Tyr Val Leu Lys
                       1605                1610                1615

Ala Asp Gly Gly Gln Tyr Tyr Asn Leu Gly Thr Thr Lys Gln Phe
                   1620                1625                1630

Leu Pro Ile Gln Leu Thr Gly Glu Lys Lys Gln Gly Asn Glu Gly Phe
               1635                1640                1645

Val Lys Gly Asn Asp Gly Asn Tyr Tyr Phe Tyr Asp Leu Ala Gly Asn
           1650                1655                1660

Met Val Lys Asn Thr Phe Ile Glu Asp Ser Val Gly Asn Trp Tyr Phe
       1665                1670                1675                1680

Phe Asp Gln Asp Gly Lys Met Val Glu Asn Lys His Phe Val Asp Val
                       1685                1690                1695

Asp Ser Tyr Gly Glu Lys Gly Thr Tyr Phe Phe Leu Lys Asn Gly Val
                   1700                1705                1710

Ser Phe Arg Gly Gly Leu Val Gln Thr Asp Asn Gly Thr Tyr Tyr Phe
               1715                1720                1725

Asp Asn Tyr Gly Lys Met Val Arg Asn Gln Thr Ile Asn Ala Gly Ala
           1730                1735                1740

Met Ile Tyr Thr Leu Asp Glu Asn Gly Lys Leu Ile Lys Ala Ser Tyr
       1745                1750                1755                1760

Asn Ser Asp Ala Glu Tyr Pro Thr Ser Thr Asp Val Gly Lys Met Leu
                       1765                1770                1775

Asp Gln Asn Lys Leu
                   1780

<210> SEQ ID NO 15
<211> LENGTH: 1455
<212> TYPE: PRT
<213> ORGANISM: streptococcus mutans SI (GtfSI)

<400> SEQUENCE: 15

Met Glu Lys Lys Val Arg Phe Lys Leu Arg Lys Val Lys Lys Arg Trp
1               5                   10                  15

Val Thr Val Ser Val Ala Ser Ala Val Val Thr Leu Thr Ser Leu Ser
            20                  25                  30

Gly Ser Leu Val Lys Ala Asp Ser Thr Asp Arg Gln Gln Ala Val
        35                  40                  45

Thr Glu Ser Gln Ala Ser Leu Val Thr Thr Ser Glu Ala Ala Lys Glu
    50                  55                  60

Thr Leu Thr Ala Thr Asp Thr Ser Thr Ala Thr Ser Ala Thr Ser Gln
65                  70                  75                  80

Pro Thr Ala Thr Val Thr Asp Asn Val Ser Thr Thr Asn Gln Ser Thr
                85                  90                  95

Asn Thr Thr Ala Asn Thr Ala Asn Phe Asp Val Lys Pro Thr Thr Thr
            100                 105                 110

Ser Glu Gln Ser Lys Thr Asp Asn Ser Asp Lys Ile Ile Ala Thr Ser
        115                 120                 125

Lys Ala Val Asn Arg Leu Thr Ala Thr Gly Lys Phe Val Pro Ala Asn
    130                 135                 140

Asn Asn Thr Ala His Ser Arg Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175
```

```
Asp Ile Ala Ala Leu Gly Asn Val Lys Asn Ile Arg Lys Val Asn Gly
            180                 185                 190

Lys Tyr Tyr Tyr Tyr Lys Glu Asp Gly Thr Leu Gln Lys Asn Tyr Ala
    195                 200                 205

Leu Asn Ile Asn Gly Lys Thr Phe Phe Phe Asp Glu Thr Gly Ala Leu
        210                 215                 220

Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Ala
            245                 250                 255

Ala Asn Phe Glu His Val Asp His Tyr Leu Thr Ala Glu Ser Trp Tyr
            260                 265                 270

Arg Pro Lys Tyr Ile Leu Lys Asp Gly Lys Thr Trp Thr Gln Ser Thr
            275                 280                 285

Glu Lys Asp Phe Arg Pro Leu Leu Met Thr Trp Trp Pro Asp Gln Glu
            290                 295                 300

Thr Gln Arg Gln Tyr Val Asn Tyr Met Asn Ala Gln Leu Gly Ile His
305                 310                 315                 320

Gln Thr Tyr Asn Thr Ala Thr Ser Pro Leu Gln Leu Asn Leu Ala Ala
            325                 330                 335

Gln Thr Ile Gln Thr Lys Ile Glu Glu Lys Ile Thr Ala Glu Lys Asn
            340                 345                 350

Thr Asn Trp Leu Arg Gln Thr Ile Ser Ala Phe Val Lys Thr Gln Ser
            355                 360                 365

Ala Trp Asn Ser Asp Ser Glu Lys Pro Phe Asp His Leu Gln Lys
370                 375                 380

Gly Ala Leu Leu Tyr Ser Asn Asn Ser Lys Leu Thr Ser Gln Ala Asn
385                 390                 395                 400

Ser Asn Tyr Arg Ile Leu Asn Arg Thr Pro Thr Asn Gln Thr Gly Lys
            405                 410                 415

Lys Asp Pro Arg Tyr Thr Ala Asp Arg Thr Ile Gly Gly Tyr Glu Phe
            420                 425                 430

Leu Leu Ala Asn Asp Val Asp Asn Ser Asn Pro Val Val Gln Ala Glu
            435                 440                 445

Gln Leu Asn Trp Leu His Phe Leu Met Asn Phe Gly Asn Ile Tyr Ala
450                 455                 460

Asn Asp Pro Asp Ala Asn Phe Asp Ser Ile Arg Val Asp Ala Val Asp
465                 470                 475                 480

Asn Val Asp Ala Asp Leu Leu Gln Ile Ala Gly Asp Tyr Leu Lys Ala
            485                 490                 495

Ala Lys Gly Ile His Lys Asn Asp Lys Ala Ala Asn Asp His Leu Ser
            500                 505                 510

Ile Leu Glu Ala Trp Ser Tyr Asn Asp Thr Pro Tyr Leu His Asp Asp
            515                 520                 525

Gly Asp Asn Met Ile Asn Met Asp Asn Arg Leu Arg Leu Ser Leu Leu
            530                 535                 540

Tyr Ser Leu Ala Lys Pro Leu Asn Gln Arg Ser Gly Met Asn Pro Leu
545                 550                 555                 560

Ile Thr Asn Ser Leu Val Asn Arg Thr Asp Asp Asn Ala Glu Thr Ala
            565                 570                 575

Ala Val Pro Ser Tyr Ser Phe Ile Arg Ala His Asp Ser Glu Val Gln
            580                 585                 590

Asp Leu Ile Arg Asn Ile Ile Arg Ala Glu Ile Asn Pro Asn Val Val
```

```
                595                 600                 605
Gly Tyr Ser Phe Thr Met Glu Glu Ile Lys Lys Ala Phe Glu Ile Tyr
610                 615                 620

Asn Lys Asp Leu Leu Ala Thr Glu Lys Lys Tyr Thr His Tyr Asn Thr
625                 630                 635                 640

Ala Leu Ser Tyr Ala Leu Leu Leu Thr Asn Lys Ser Ser Val Pro Arg
                645                 650                 655

Val Tyr Tyr Gly Asp Met Phe Thr Asp Asp Gly Gln Tyr Met Ala His
                660                 665                 670

Lys Thr Ile Asn Tyr Glu Ala Ile Glu Thr Leu Leu Lys Ala Arg Ile
                675                 680                 685

Lys Tyr Val Ser Gly Gly Gln Ala Met Arg Asn Gln Gln Val Gly Asn
                690                 695                 700

Ser Glu Ile Ile Thr Ser Val Arg Tyr Gly Lys Gly Ala Leu Lys Ala
705                 710                 715                 720

Thr Asp Thr Gly Asp Arg Thr Thr Arg Thr Ser Gly Val Ala Val Ile
                725                 730                 735

Glu Gly Asn Asn Pro Ser Leu Arg Leu Lys Ala Ser Asp Arg Val Val
                740                 745                 750

Val Asn Met Gly Ala Ala His Lys Asn Gln Ala Tyr Arg Pro Leu Leu
                755                 760                 765

Leu Thr Thr Asp Asn Gly Ile Lys Ala Tyr His Ser Asp Gln Glu Ala
                770                 775                 780

Ala Gly Leu Val Arg Tyr Thr Asn Asp Arg Gly Glu Leu Ile Phe Thr
785                 790                 795                 800

Ala Ala Asp Ile Lys Gly Tyr Ala Asn Pro Gln Val Ser Gly Tyr Leu
                805                 810                 815

Gly Val Trp Val Pro Val Gly Ala Ala Asp Gln Asp Val Arg Val
                820                 825                 830

Ala Ala Ser Thr Ala Pro Ser Thr Asp Gly Lys Ser Val His Gln Asn
                835                 840                 845

Ala Ala Leu Asp Ser Arg Val Met Phe Glu Gly Phe Ser Asn Phe Gln
850                 855                 860

Ala Phe Ala Thr Lys Lys Glu Glu Tyr Thr Asn Val Val Ile Ala Lys
865                 870                 875                 880

Asn Val Asp Lys Phe Ala Glu Trp Gly Val Thr Asp Phe Glu Met Ala
                885                 890                 895

Pro Gln Tyr Val Ser Ser Thr Asp Gly Ser Phe Leu Asp Ser Val Ile
                900                 905                 910

Gln Asn Gly Tyr Ala Phe Thr Asp Arg Tyr Asp Leu Gly Ile Ser Lys
                915                 920                 925

Pro Asn Lys Tyr Gly Thr Ala Asp Asp Leu Val Lys Ala Ile Lys Ala
930                 935                 940

Leu His Ser Lys Gly Ile Lys Val Met Ala Asp Trp Val Pro Asp Gln
945                 950                 955                 960

Met Tyr Ala Leu Pro Glu Lys Glu Val Val Thr Ala Thr Arg Val Asp
                965                 970                 975

Lys Tyr Gly Thr Pro Val Ala Gly Ser Gln Ile Lys Asn Thr Leu Tyr
                980                 985                 990

Val Val Asp Gly Lys Ser Ser Gly Lys Asp Gln Gln Ala Lys Tyr Gly
                995                 1000                1005

Gly Ala Phe Leu Glu Glu Leu Gln Ala Lys Tyr Pro Glu Leu Phe Ala
                1010                1015                1020
```

Arg Lys Gln Ile Ser Thr Gly Val Pro Met Asp Pro Ser Val Lys Ile
1025                1030                1035                1040

Lys Gln Trp Ser Ala Lys Tyr Phe Asn Gly Thr Asn Ile Leu Gly Arg
            1045                1050                1055

Gly Ala Gly Tyr Val Leu Lys Asp Gln Ala Thr Asn Thr Tyr Phe Ser
        1060                1065                1070

Leu Val Ser Asp Asn Thr Phe Leu Pro Lys Ser Leu Val Asn Pro Asn
    1075                1080                1085

His Gly Thr Ser Ser Ser Val Thr Gly Leu Val Phe Asp Gly Lys Gly
1090                1095                1100

Tyr Val Tyr Tyr Ser Thr Ser Gly Asn Gln Ala Lys Asn Ala Phe Ile
1105                1110                1115                1120

Ser Leu Gly Asn Asn Trp Tyr Tyr Phe Asp Asn Asn Gly Tyr Met Val
                1125                1130                1135

Thr Gly Ala Gln Ser Ile Asn Gly Ala Asn Tyr Tyr Phe Leu Ser Asn
            1140                1145                1150

Gly Ile Gln Leu Arg Asn Ala Ile Tyr Asp Asn Gly Asn Lys Val Leu
        1155                1160                1165

Ser Tyr Tyr Gly Asn Asp Gly Arg Arg Tyr Glu Asn Gly Tyr Tyr Leu
    1170                1175                1180

Phe Gly Gln Gln Trp Arg Tyr Phe Gln Asn Gly Ile Met Ala Val Gly
1185                1190                1195                1200

Leu Thr Arg Ile His Gly Ala Val Gln Tyr Phe Asp Ala Ser Gly Phe
                1205                1210                1215

Gln Ala Lys Gly Gln Phe Ile Thr Thr Ala Asp Gly Lys Leu Arg Tyr
            1220                1225                1230

Phe Asp Arg Asp Ser Gly Asn Gln Ile Ser Asn Arg Phe Val Arg Asn
        1235                1240                1245

Ser Lys Gly Glu Trp Phe Leu Phe Asp His Asn Gly Val Ala Val Thr
    1250                1255                1260

Gly Thr Val Thr Phe Asn Gly Gln Arg Leu Tyr Phe Lys Pro Asn Gly
1265                1270                1275                1280

Val Gln Ala Lys Gly Glu Phe Ile Arg Asp Ala Asp Gly His Leu Arg
                1285                1290                1295

Tyr Tyr Asp Pro Asn Ser Gly Asn Glu Val Arg Asn Arg Phe Val Arg
            1300                1305                1310

Asn Ser Lys Gly Glu Trp Phe Leu Phe Asp His Asn Gly Ile Ala Val
        1315                1320                1325

Thr Gly Thr Arg Val Val Asn Gly Gln Arg Leu Tyr Phe Lys Ser Asn
    1330                1335                1340

Gly Val Gln Ala Lys Gly Glu Leu Ile Thr Glu Arg Lys Gly Arg Ile
1345                1350                1355                1360

Lys Tyr Tyr Asp Pro Asn Ser Gly Asn Glu Val Arg Asn Arg Tyr Val
                1365                1370                1375

Arg Thr Ser Ser Gly Asn Trp Tyr Tyr Phe Gly Asn Asp Gly Tyr Ala
            1380                1385                1390

Leu Ile Gly Trp His Val Val Glu Gly Arg Arg Val Tyr Phe Asp Glu
        1395                1400                1405

Asn Gly Val Tyr Arg Tyr Ala Ser His Asp Gln Arg Asn His Trp Asp
    1410                1415                1420

Tyr Asp Tyr Arg Arg Asp Phe Gly Arg Gly Ser Ser Ser Ala Val Arg
1425                1430                1435                1440

```
Phe Arg His Ser Arg Asn Gly Phe Phe Asp Asn Phe Phe Arg Phe
                1445                1450                1455

<210> SEQ ID NO 16
<211> LENGTH: 2057
<212> TYPE: PRT
<213> ORGANISM: Leuconostoc mesenteroides

<400> SEQUENCE: 16

Met Lys Gln Gln Glu Thr Val Thr Arg Lys Lys Leu Tyr Lys Ser Gly
  1               5                  10                  15

Lys Val Trp Val Ala Ala Ala Thr Ala Phe Ala Val Leu Gly Val Ser
                 20                  25                  30

Thr Val Thr Thr Val His Ala Asp Thr Asn Ser Asn Val Ala Val Lys
             35                  40                  45

Gln Ile Asn Asn Thr Gly Thr Asn Asp Ser Gly Glu Lys Lys Val Pro
         50                  55                  60

Val Pro Ser Thr Asn Asn Asp Ser Leu Lys Gln Gly Thr Asp Gly Phe
 65                  70                  75                  80

Trp Tyr Asp Ser Asp Gly Asn Arg Val Asp Gln Lys Thr Asn Gln Ile
                 85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Glu Asn Ile Ser Lys
            115                 120                 125

Gln Thr Lys Ile Ala Asn Gln Gln Thr Val Asp Thr Ala Lys Gly Leu
        130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Phe Gln Asp Val Asn Asn
        275                 280                 285

Lys Arg Ile Tyr Phe Ala Pro Asn Thr Gly Asn Ala Val Ala Asn Thr
    290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365
```

```
Thr Phe Asn Asn Gln Phe Met Tyr Phe Asp Ala Asp Thr Gly Ala Gly
    370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495

Val Ile Gln Thr Ala Ile Glu Gln Gln Ile Ser Leu Lys Lys Ser Thr
            500                 505                 510

Glu Trp Leu Arg Asp Ala Ile Asp Ser Phe Val Lys Thr Gln Ala Asn
        515                 520                 525

Trp Asn Lys Gln Thr Glu Asp Glu Ala Phe Asp Gly Leu Gln Trp Leu
530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
        595                 600                 605

Asn Trp Leu His Tyr Leu Met Asn Phe Gly Ser Ile Thr Gly Asn Asn
        610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gln Gly Asn
        675                 680                 685

Ala Gln Leu Thr Met Asp Tyr Thr Val Thr Ser Gln Phe Gly Asn Ser
        690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
        755                 760                 765

Asp Ala Gln Asp Pro Ile Arg Lys Ala Met Ile Asp His Gly Ile Ile
770                 775                 780
```

```
Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
            805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
            835                 840                 845

Gln Tyr Met Glu Lys Gly Thr Ile Tyr Asn Pro Val Ile Ser Ala Leu
            850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
            885                 890                 895

Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
            915                 920                 925

Gly Asn Asn Pro Asp Leu Lys Leu Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
            965                 970                 975

Thr Leu Arg Thr Asn Asp Asn Gly Asp Leu Ile Phe His Lys Thr Asn
            980                 985                 990

Thr Phe Val Lys Gln Asp Gly Thr Ile Ile Asn Tyr Glu Met Lys Gly
            995                 1000                1005

Ser Leu Asn Ala Leu Ile Ser Gly Tyr Leu Gly Val Trp Val Pro Val
            1010                1015                1020

Gly Ala Ser Asp Ser Gln Asp Ala Arg Thr Val Ala Thr Glu Ser Ser
            1025                1030                1035                1040

Ser Ser Asn Asp Gly Ser Val Phe His Ser Asn Ala Ala Leu Asp Ser
                        1045                1050                1055

Asn Val Ile Tyr Glu Gly Phe Ser Asn Phe Gln Ala Met Pro Thr Ser
            1060                1065                1070

Pro Glu Gln Ser Thr Asn Val Val Ile Ala Thr Lys Ala Asn Leu Phe
            1075                1080                1085

Lys Glu Leu Gly Ile Thr Ser Phe Glu Leu Ala Pro Gln Tyr Arg Ser
            1090                1095                1100

Ser Gly Asp Thr Asn Tyr Gly Gly Met Ser Phe Leu Asp Ser Phe Leu
1105                1110                1115                1120

Asn Asn Gly Tyr Ala Phe Thr Asp Arg Tyr Asp Leu Gly Phe Asn Lys
            1125                1130                1135

Ala Asp Gly Asn Pro Asn Pro Thr Lys Tyr Gly Thr Gln Asp Leu
            1140                1145                1150

Arg Asn Ala Ile Glu Ala Leu His Lys Asn Gly Met Gln Ala Ile Ala
            1155                1160                1165

Asp Trp Val Pro Asp Gln Ile Tyr Ala Leu Pro Gly Lys Glu Val Val
            1170                1175                1180

Thr Ala Thr Arg Val Asp Glu Arg Gly Asn Gln Leu Lys Asp Thr Asp
1185                1190                1195                1200

Phe Val Asn Leu Leu Tyr Val Ala Asn Thr Lys Ser Ser Gly Val Asp
```

-continued

```
                1205                1210                1215
Tyr Gln Ala Lys Tyr Gly Gly Glu Phe Leu Asp Lys Leu Arg Glu Glu
                1220                1225                1230
Tyr Pro Ser Leu Phe Lys Gln Asn Gln Val Ser Thr Gly Gln Pro Ile
                1235                1240                1245
Asp Ala Ser Thr Lys Ile Lys Gln Trp Ser Ala Lys Tyr Met Asn Gly
                1250                1255                1260
Thr Asn Ile Leu His Arg Gly Ala Tyr Tyr Val Leu Lys Asp Trp Ala
1265                1270                1275                1280
Thr Asn Gln Tyr Phe Asn Ile Ala Lys Thr Asn Glu Val Phe Leu Pro
                1285                1290                1295
Leu Gln Leu Gln Asn Lys Asp Ala Gln Thr Gly Phe Ile Ser Asp Ala
                1300                1305                1310
Ser Gly Val Lys Tyr Tyr Ser Ile Ser Gly Tyr Gln Ala Lys Asp Thr
                1315                1320                1325
Phe Ile Glu Asp Gly Asn Gly Asn Trp Tyr Tyr Phe Asp Lys Asp Gly
                1330                1335                1340
Tyr Met Val Arg Ser Gln Gln Gly Glu Asn Pro Ile Arg Thr Val Glu
1345                1350                1355                1360
Thr Ser Val Asn Thr Arg Asn Gly Asn Tyr Tyr Phe Met Pro Asn Gly
                1365                1370                1375
Val Glu Leu Arg Lys Gly Phe Gly Thr Asp Asn Ser Gly Asn Val Tyr
                1380                1385                1390
Tyr Phe Asp Asp Gln Gly Lys Met Val Arg Asp Lys Tyr Ile Asn Asp
                1395                1400                1405
Asp Ala Asn Asn Phe Tyr His Leu Asn Val Asp Gly Thr Met Ser Arg
                1410                1415                1420
Gly Leu Phe Lys Phe Asp Ser Asp Thr Leu Gln Tyr Phe Ala Ser Asn
1425                1430                1435                1440
Gly Val Gln Ile Lys Asp Ser Tyr Ala Lys Asp Ser Lys Gly Asn Lys
                1445                1450                1455
Tyr Tyr Phe Asp Ser Ala Thr Gly Asn Asn Asp Thr Gly Lys Ala Gln
                1460                1465                1470
Thr Trp Asp Gly Asn Gly Tyr Tyr Ile Thr Ile Asp Ser Asp Ala Asn
                1475                1480                1485
Asn Thr Ile Gly Val Asn Thr Asp Tyr Thr Ala Tyr Ile Thr Ser Ser
                1490                1495                1500
Leu Arg Glu Asp Gly Leu Phe Ala Asn Ala Pro Tyr Gly Val Val Thr
1505                1510                1515                1520
Lys Asp Gln Asn Gly Asn Asp Leu Lys Trp Gln Tyr Ile Asn His Thr
                1525                1530                1535
Lys Gln Tyr Glu Gly Gln Gln Val Gln Val Thr Arg Gln Tyr Thr Asp
                1540                1545                1550
Ser Lys Gly Val Ser Trp Asn Leu Ile Thr Phe Ala Gly Gly Asp Leu
                1555                1560                1565
Gln Gly Gln Arg Leu Trp Val Asp Ser Arg Ala Leu Thr Met Thr Pro
                1570                1575                1580
Phe Lys Thr Met Asn Gln Ile Ser Phe Ile Ser Tyr Ala Asn Arg Asn
1585                1590                1595                1600
Asp Gly Leu Phe Leu Asn Ala Pro Tyr Gln Val Lys Gly Tyr Gln Leu
                1605                1610                1615
Ala Gly Met Ser Asn Gln Tyr Lys Gly Gln Gln Val Thr Ile Ala Gly
                1620                1625                1630
```

```
Val Ala Asn Val Ser Gly Lys Asp Trp Ser Leu Ile Ser Phe Asn Gly
        1635                1640                1645

Thr Gln Tyr Trp Ile Asp Ser Gln Ala Leu Asn Thr Asn Phe Thr His
    1650                1655                1660

Asp Met Asn Gln Lys Val Phe Val Asn Thr Thr Ser Asn Leu Asp Gly
1665                1670                1675                1680

Leu Phe Leu Asn Ala Pro Tyr Arg Gln Pro Gly Tyr Lys Leu Ala Gly
                1685                1690                1695

Leu Ala Lys Asn Tyr Asn Asn Gln Thr Val Thr Val Ser Gln Gln Tyr
            1700                1705                1710

Phe Asp Asp Gln Gly Thr Val Trp Ser Gln Val Val Leu Gly Gly Gln
        1715                1720                1725

Thr Val Trp Val Asp Asn His Ala Leu Ala Gln Met Gln Val Ser Asp
    1730                1735                1740

Thr Asp Gln Gln Leu Tyr Val Asn Ser Asn Gly Arg Asn Asp Gly Leu
1745                1750                1755                1760

Phe Leu Asn Ala Pro Tyr Arg Gly Gln Gly Ser Gln Leu Ile Gly Met
                1765                1770                1775

Thr Ala Asp Tyr Asn Gly Gln His Val Gln Val Thr Lys Gln Gly Gln
            1780                1785                1790

Asp Ala Tyr Gly Ala Gln Trp Arg Leu Ile Thr Leu Asn Asn Gln Gln
        1795                1800                1805

Val Trp Val Asp Ser Arg Ala Leu Ser Thr Thr Ile Met Gln Ala Met
    1810                1815                1820

Asn Asp Asn Met Tyr Val Asn Ser Ser Gln Arg Thr Asp Gly Leu Trp
1825                1830                1835                1840

Leu Asn Ala Pro Tyr Thr Met Ser Gly Ala Lys Trp Ala Gly Asp Thr
                1845                1850                1855

Arg Ser Ala Asn Gly Arg Tyr Val His Ile Ser Lys Ala Tyr Ser Asn
            1860                1865                1870

Glu Val Gly Asn Thr Tyr Tyr Leu Thr Asn Leu Asn Gly Gln Ser Thr
        1875                1880                1885

Trp Ile Asp Lys Arg Ala Phe Thr Val Thr Phe Asp Gln Val Val Ala
    1890                1895                1900

Leu Asn Ala Thr Ile Val Ala Arg Gln Arg Pro Asp Gly Met Phe Lys
1905                1910                1915                1920

Thr Ala Pro Tyr Gly Glu Ala Gly Ala Gln Phe Val Asp Tyr Val Thr
                1925                1930                1935

Asn Tyr Asn Gln Gln Thr Val Pro Val Thr Lys Gln His Ser Asp Ala
            1940                1945                1950

Gln Gly Asn Gln Trp Tyr Leu Ala Thr Val Asn Gly Thr Gln Tyr Trp
        1955                1960                1965

Ile Asp Gln Arg Ser Phe Ser Pro Val Thr Lys Val Val Asp Tyr
    1970                1975                1980

Gln Ala Lys Ile Val Pro Arg Thr Thr Arg Asp Gly Val Phe Ser Gly
1985                1990                1995                2000

Ala Pro Tyr Gly Glu Val Asn Ala Lys Leu Val Asn Met Ala Thr Ala
                2005                2010                2015

Tyr Gln Asn Gln Val Val His Ala Thr Gly Glu Tyr Thr Asn Ala Ser
            2020                2025                2030

Gly Ile Thr Trp Ser Gln Phe Ala Leu Ser Gly Gln Glu Asp Lys Leu
        2035                2040                2045
```

-continued

```
Trp Ile Asp Lys Arg Ala Leu Gln Ala
    2050                2055

<210> SEQ ID NO 17
<211> LENGTH: 2835
<212> TYPE: PRT
<213> ORGANISM: Leuconostoc citreum

<400> SEQUENCE: 17

Met Arg Asp Met Arg Val Ile Cys Asp Arg Lys Lys Leu Tyr Lys Ser
1               5                   10                  15

Gly Lys Val Leu Val Thr Ala Gly Ile Phe Ala Leu Met Met Phe Gly
            20                  25                  30

Val Thr Thr Ala Ser Val Ser Ala Asn Thr Ile Ala Val Asp Thr Asn
        35                  40                  45

His Ser Arg Thr Ser Ala Gln Ile Asn Lys Ser Ala Val Asp Lys Val
    50                  55                  60

Asn Asp Asp Lys Thr Thr Leu Gly Ala Ala Lys Val Val Ala Val Ala
65                  70                  75                  80

Thr Thr Pro Ala Thr Pro Val Ala Asp Lys Thr Val Ser Ala Pro Ala
                85                  90                  95

Ala Asp Lys Ala Val Asp Thr Thr Ser Ser Thr Thr Pro Ala Thr Asp
            100                 105                 110

Lys Ala Val Asp Thr Thr Pro Thr Pro Ala Ala Asp Lys Ala Val
            115                 120                 125

Asp Thr Thr Pro Thr Thr Pro Ala Ala Asp Lys Ala Val Asp Thr Thr
            130                 135                 140

Pro Thr Thr Pro Ala Ala Asn Lys Ala Val Asp Thr Thr Pro Ala Thr
145                 150                 155                 160

Ala Ala Thr Asp Lys Ala Val Ala Thr Pro Ala Thr Pro Ala Ala Asp
                165                 170                 175

Lys Leu Ala Asn Thr Thr Pro Ala Thr Asp Lys Ala Val Ala Thr Thr
            180                 185                 190

Pro Ala Thr Pro Val Ala Asn Lys Ala Ala Asp Thr Ser Ser Ile His
            195                 200                 205

Asp Gln Pro Leu Asp Thr Asn Val Pro Thr Asp Lys Ser Ala Asn Leu
    210                 215                 220

Val Ser Thr Thr Gln Lys Ser Thr Asp Asn Gln Val Lys Ser Thr
225                 230                 235                 240

Glu Thr Ser His Leu Gln Glu Ile Asn Gly Lys Thr Tyr Phe Leu Asp
                245                 250                 255

Asp Asn Gly Gln Val Lys Lys Asn Phe Thr Ala Ile Ile Asp Gly Lys
            260                 265                 270

Val Leu Tyr Phe Asp Lys Thr Ser Gly Glu Leu Thr Ala Asn Ala Pro
            275                 280                 285

Gln Val Thr Lys Gly Leu Val Asn Ile Asp Asn Ala His Asn Ala Ala
            290                 295                 300

His Asp Leu Thr Ala Asp Asn Phe Thr Asn Val Asp Gly Tyr Leu Thr
305                 310                 315                 320

Ala Asn Ser Trp Tyr Arg Pro Lys Asp Ile Leu Lys Asn Gly Thr Thr
                325                 330                 335

Trp Thr Pro Thr Thr Ala Glu Asp Phe Arg Pro Leu Leu Met Ser Trp
            340                 345                 350

Trp Pro Asp Lys Asn Thr Gln Val Ala Tyr Leu Gln Tyr Met Gln Ser
            355                 360                 365
```

Val Gly Met Leu Pro Asp Asp Val Lys Val Ser Asn Asp Asn Met
    370                 375                 380

Ser Thr Leu Thr Asp Ala Ala Met Thr Val Gln Lys Asn Ile Glu Ser
385                 390                 395                 400

Arg Ile Gly Val Ser Gly Lys Thr Asp Trp Leu Lys Gln Asp Met Asn
                405                 410                 415

Lys Leu Ile Asp Ser Gln Ala Asn Trp Asn Ile Asp Ser Glu Ser Lys
                420                 425                 430

Gly Asn Asp His Leu Gln Gly Gly Ala Leu Leu Tyr Val Asn Asp Asp
                435                 440                 445

Lys Thr Pro Asn Ala Asn Ser Asp Tyr Arg Leu Leu Asn Arg Thr Pro
    450                 455                 460

Thr Asn Gln Thr Gly Gln Ile Thr Asp Pro Ser Lys Gln Gly Gly Tyr
465                 470                 475                 480

Glu Met Leu Leu Ala Asn Asp Val Asp Asn Ser Asn Pro Val Val Gln
                485                 490                 495

Ala Glu Gln Leu Asn Trp Leu His Tyr Met Met Asn Ile Gly Thr Ile
                500                 505                 510

Ala Gln Asn Asp Pro Thr Ala Asn Phe Asp Gly Tyr Arg Val Asp Ala
                515                 520                 525

Val Asp Asn Val Asp Ala Asp Leu Leu Gln Ile Ala Gly Asp Tyr Phe
    530                 535                 540

Lys Ala Ala Tyr Gly Thr Gly Lys Thr Glu Ala Asn Ala Asn Asn His
545                 550                 555                 560

Ile Ser Ile Leu Glu Asp Trp Asp Asn Asp Ser Ala Tyr Ile Lys
                565                 570                 575

Ala His Gly Asn Asn Gln Leu Thr Met Asp Phe Pro Ala His Leu Ala
                580                 585                 590

Leu Lys Tyr Ala Leu Asn Met Pro Leu Ala Ala Gln Ser Gly Leu Glu
    595                 600                 605

Pro Leu Ile Asn Thr Ser Leu Val Lys Arg Gly Lys Asp Ala Thr Glu
    610                 615                 620

Asn Glu Ala Gln Pro Asn Tyr Ala Phe Ile Arg Ala His Asp Ser Glu
625                 630                 635                 640

Val Gln Thr Val Ile Ala Gln Ile Ile Lys Asp Lys Ile Asn Thr Lys
                645                 650                 655

Ser Asp Gly Leu Thr Val Thr Pro Asp Glu Ile Lys Gln Ala Phe Thr
                660                 665                 670

Ile Tyr Asn Ala Asp Glu Leu Lys Ala Asp Lys Glu Tyr Thr Ala Tyr
    675                 680                 685

Asn Ile Pro Ala Ser Tyr Ala Val Leu Leu Thr Asn Lys Asp Thr Val
    690                 695                 700

Pro Arg Val Tyr Tyr Gly Asp Leu Phe Ser Asp Asp Gly Gln Tyr Met
705                 710                 715                 720

Ser Gln Lys Ser Pro Tyr Tyr Asp Ala Ile Thr Ser Leu Leu Lys Ser
                725                 730                 735

Arg Ile Lys Tyr Val Ala Gly Gly Gln Ser Met Asn Met Thr Tyr Leu
                740                 745                 750

His Glu Cys Phe Asp Pro Ala Lys Asn Glu Thr Lys Pro Gln Gly Val
            755                 760                 765

Leu Thr Ser Val Arg Tyr Gly Lys Gly Ala Met Thr Ala Asp Asp Leu
    770                 775                 780

```
Gly Asn Ser Asp Thr Arg Gln Gln Gly Ile Gly Leu Val Ile Asn Asn
785                 790                 795                 800

Lys Pro Phe Leu Asn Leu Asn Asp Glu Gln Ile Val Leu Asn Met
            805                 810                 815

Gly Ala Ala His Lys Asn Gln Ala Tyr Arg Pro Leu Met Leu Thr Thr
            820                 825                 830

Lys Ser Gly Leu Gln Ile Tyr Asp Lys Asp Ala Gly Ala Pro Val Val
            835                 840                 845

Tyr Thr Asn Asp Ala Gly Gln Leu Ile Phe Lys Ser Asp Met Val Tyr
            850                 855                 860

Gly Val Ser Asn Pro Gln Val Ser Gly Tyr Phe Ala Ala Trp Val Pro
865                 870                 875                 880

Val Gly Ala Ser Asp Ser Gln Asp Ala Arg Thr Gln Ser Ser Gln Ser
            885                 890                 895

Glu Thr Lys Asp Gly Asp Val Tyr His Ser Asn Ala Ala Leu Asp Ser
            900                 905                 910

Asn Val Ile Tyr Glu Gly Phe Ser Asn Phe Gln Ala Met Pro Glu Lys
            915                 920                 925

Asn Asp Asp Phe Thr Asn Val Lys Ile Ala Gln Asn Ala Lys Leu Phe
            930                 935                 940

Lys Asp Leu Gly Ile Thr Ser Phe Glu Leu Ala Pro Gln Tyr Arg Ser
945                 950                 955                 960

Ser Thr Asp Asn Ser Phe Leu Asp Ser Val Ile Gln Asn Gly Tyr Ala
            965                 970                 975

Phe Thr Asp Arg Tyr Asp Val Gly Tyr Asn Thr Pro Thr Lys Tyr Gly
            980                 985                 990

Thr Val Asp Gln Leu Leu Asp Ser Leu Arg Ala Leu His Ala Gln Gly
            995                 1000                1005

Ile Gln Ala Ile Asn Asp Trp Val Pro Asp Gln Ile Tyr Asn Leu Pro
1010                1015                1020

Gly Glu Gln Ile Val Thr Ala Val Arg Thr Asn Gly Ser Gly Lys Tyr
1025                1030                1035                1040

Asp Tyr Asp Ser Val Ile Asn Asn Thr Leu Tyr Asp Ser Arg Thr Val
                1045                1050                1055

Gly Gly Gly Glu Tyr Gln Glu Lys Phe Gly Gly Leu Phe Leu Asp Gln
1060                1065                1070

Leu Lys Lys Asp Tyr Pro Ser Leu Phe Glu Thr Lys Gln Ile Ser Thr
            1075                1080                1085

Asn Gln Pro Met Asn Pro Asp Val Lys Ile Lys Glu Trp Ser Ala Lys
            1090                1095                1100

Tyr Phe Asn Gly Ser Asn Ile Gln Gly Arg Gly Ala Trp Tyr Val Leu
1105                1110                1115                1120

Lys Asp Trp Ala Thr Asn Gln Tyr Phe Asn Val Ser Ser Asp Asn Gly
            1125                1130                1135

Phe Leu Pro Lys Gln Leu Leu Gly Glu Lys Thr Ser Thr Gly Phe Ile
            1140                1145                1150

Thr Glu Asn Gly Lys Thr Ser Phe Tyr Ser Thr Ser Gly Tyr Gln Ala
            1155                1160                1165

Lys Asp Thr Phe Ile Gln Asp Gly Thr Asn Trp Tyr Tyr Phe Asp Asn
            1170                1175                1180

Ala Gly Tyr Met Leu Thr Gly Lys Gln Asn Ile His Asp Lys Asn Tyr
1185                1190                1195                1200

Tyr Phe Leu Pro Asn Gly Val Glu Leu Gln Asp Ala Tyr Leu Phe Asp
```

-continued

```
                1205                1210                1215

Gly Asn Gln Glu Phe Tyr Tyr Asn Lys Ala Gly Glu Gln Val Met Asn
            1220                1225                1230

Gln Tyr Tyr Gln Asp Ser Gln Asn Gln Trp His Tyr Phe Phe Glu Asn
        1235                1240                1245

Gly Arg Met Ala Ile Gly Leu Thr Glu Val Pro Asn Ala Asp Gly Thr
    1250                1255                1260

His Val Thr Gln Tyr Phe Asp Ala Asn Gly Val Gln Ile Lys Gly Thr
1265                1270                1275                1280

Ala Ile Lys Asp Gln Asn Asn Gln Leu Arg Tyr Phe Asp Glu Ala Thr
            1285                1290                1295

Gly Asn Met Val Val Asn Ser Trp Gly Gln Leu Ala Asp Lys Ser Trp
        1300                1305                1310

Leu Tyr Leu Asn Ala Gln Gly Val Ala Val Thr Gly Asn Gln Lys Ile
    1315                1320                1325

Asp Gly Glu Glu Tyr Tyr Phe Asn Ala Asp Gly Lys Gln Val Lys Gly
        1330                1335                1340

Asn Ala Ile Ile Asp Asn Asn Gly Asp Gln Arg Tyr Tyr Asp Gly Asp
1345                1350                1355                1360

Lys Gly Val Met Val Val Asn Ser Trp Gly Glu Leu Pro Asp Gly Ser
            1365                1370                1375

Trp Leu Tyr Leu Asn Asp Lys Gly Ile Ala Val Thr Gly Arg Gln Val
        1380                1385                1390

Ile Asn Asn Gln Val Asn Phe Phe Gly Asn Asp Gly Lys Gln Ile Lys
    1395                1400                1405

Asp Ala Phe Lys Leu Leu Ser Asp Gly Ser Trp Val Tyr Leu Asp Asp
        1410                1415                1420

Lys Gly Leu Ile Thr Thr Gly Ala Lys Val Ile Asn Gly Leu Asn Met
1425                1430                1435                1440

Phe Phe Asp Lys Asp Gly His Gln Ile Lys Gly Asp Ala Ser Thr Asp
            1445                1450                1455

Ala Asn Gly Lys Arg His Tyr Tyr Asp Lys Asn Asp Gly His Leu Val
        1460                1465                1470

Thr Asn Ser Trp Gly Glu Leu Pro Asp Gly Ser Trp Leu Tyr Leu Glu
    1475                1480                1485

Glu Gln Gly Asp Ala Val Thr Gly Gln Arg Val Ile Asp Gly Lys Thr
        1490                1495                1500

Arg Tyr Phe Asp Glu Asp Gly Lys Gln Ile Lys Asn Ser Leu Lys Thr
1505                1510                1515                1520

Leu Ala Asn Gly Asp Lys Ile Tyr Leu Asp Gly Asp Gly Val Ala Ala
            1525                1530                1535

Thr Gly Leu Gln His Val Gly Asp Lys Ile Met Tyr Phe Asp Glu Asp
        1540                1545                1550

Gly Lys Gln Val Val Gly Lys Phe Val Ser Ala Lys Asp Gly Ser Trp
    1555                1560                1565

Tyr Tyr Leu Asn Gln Asp Gly Val Ala Ala Val Gly Pro Ser Ser Ile
        1570                1575                1580

Asn Gly Gln Ser Leu Tyr Phe Asp Gln Asp Gly Lys Gln Val Lys Tyr
1585                1590                1595                1600

Asn Glu Val Arg Asn Ser Asp Gly Thr Thr Asn Tyr Tyr Thr Gly Leu
            1605                1610                1615

Thr Gly Glu Lys Leu Thr Gln Asp Phe Gly Glu Leu Pro Asp Gly Ser
        1620                1625                1630
```

Trp Ile Tyr Leu Asp Ala Gln Gly His Thr Val Thr Gly Ala Gln Ile
        1635                1640                1645

Ile Asn Gly Gln Asn Leu Tyr Phe Lys Ala Asp Gly Gln Gln Val Lys
        1650                1655                1660

Gly His Ala Tyr Thr Asp Gln Leu Gly His Met Arg Phe Tyr Asp Pro
1665                1670                1675                1680

Asp Ser Gly Asp Met Leu Ser Asn Arg Phe Glu Gln Ile Thr Pro Gly
            1685                1690                1695

Val Trp Ala Tyr Phe Gly Ala Asp Gly Val Ala Ile Thr Gly Gln His
            1700                1705                1710

Asp Ile Asn Gly Gln Lys Leu Phe Phe Asp Glu Thr Gly Tyr Gln Val
        1715                1720                1725

Lys Gly Ser Gln Arg Thr Ile Asp Gly Thr Leu Tyr Ser Phe Asp Ser
        1730                1735                1740

Gln Thr Gly Asn Gln Lys Arg Val Gln Thr Thr Leu Leu Pro Gln Ala
1745                1750                1755                1760

Gly His Tyr Ile Thr Lys Asn Gly Asn Asp Trp Gln Tyr Asp Thr Asn
            1765                1770                1775

Gly Glu Leu Ala Lys Gly Leu Arg Gln Asp Ser Asn Gly Lys Leu Arg
            1780                1785                1790

Tyr Phe Asp Leu Thr Thr Gly Ile Gln Ala Lys Gly Gln Phe Val Thr
        1795                1800                1805

Ile Gly Gln Glu Thr Tyr Tyr Phe Ser Lys Asp His Gly Asp Ala Gln
        1810                1815                1820

Leu Leu Pro Met Val Thr Glu Gly His Tyr Gly Thr Ile Thr Leu Lys
1825                1830                1835                1840

Gln Gly Gln Asp Thr Lys Thr Ala Trp Val Tyr Arg Asp Gln Asn Asn
            1845                1850                1855

Thr Ile Leu Lys Gly Leu Gln Asn Ile Asn Gly Thr Leu Gln Phe Phe
            1860                1865                1870

Asp Pro Tyr Thr Gly Glu Gln Leu Lys Gly Gly Val Ala Lys Tyr Asp
        1875                1880                1885

Asp Lys Leu Phe Tyr Phe Glu Ser Gly Lys Gly Asn Leu Val Ser Thr
        1890                1895                1900

Val Ala Gly Asp Tyr Gln Asp Gly His Tyr Ile Ser Gln Asp Gly Gln
1905                1910                1915                1920

Thr Arg Tyr Ala Asp Lys Gln Asn Gln Leu Val Lys Gly Leu Val Thr
            1925                1930                1935

Val Asn Gly Ala Leu Gln Tyr Phe Asp Asn Ala Thr Gly Asn Gln Ile
            1940                1945                1950

Lys Asn Gln Gln Val Ile Val Asp Gly Lys Thr Tyr Tyr Phe Asp Asp
        1955                1960                1965

Lys Gly Asn Gly Glu Tyr Leu Phe Thr Asn Thr Leu Asp Met Ser Thr
        1970                1975                1980

Asn Ala Phe Ser Thr Lys Asn Val Ala Phe His Asp Ser Ser Ser
1985                1990                1995                2000

Phe Asp His Thr Val Asp Gly Phe Leu Thr Ala Asp Thr Trp Tyr Arg
            2005                2010                2015

Pro Lys Ser Ile Leu Ala Asn Gly Thr Thr Trp Arg Asp Ser Thr Asp
            2020                2025                2030

Lys Asp Met Arg Pro Leu Ile Thr Val Trp Trp Pro Asn Lys Asn Val
        2035                2040                2045

```
Gln Val Asn Tyr Leu Asn Phe Met Lys Ala Asn Gly Leu Leu Thr Thr
     2050                2055                2060

Ala Ala Gln Tyr Thr Leu His Ser Asp Gln Tyr Asp Leu Asn Gln Ala
2065                2070                2075                2080

Ala Gln Asp Val Gln Val Ala Ile Glu Arg Arg Ile Ala Ser Glu His
             2085                2090                2095

Gly Thr Asp Trp Leu Gln Lys Leu Leu Phe Glu Ser Gln Asn Asn Asn
         2100                2105                2110

Pro Ser Phe Val Lys Gln Gln Phe Ile Trp Asn Lys Asp Ser Glu Tyr
             2115                2120                2125

His Gly Gly Gly Asp Ala Trp Phe Gln Gly Gly Tyr Leu Lys Tyr Gly
         2130                2135                2140

Asn Asn Pro Leu Thr Pro Thr Thr Asn Ser Asp Tyr Arg Gln Pro Gly
2145                2150                2155                2160

Asn Ala Phe Asp Phe Leu Leu Ala Asn Asp Val Asp Asn Ser Asn Pro
             2165                2170                2175

Val Val Gln Ala Glu Asn Leu Asn Trp Leu His Tyr Leu Met Asn Phe
             2180                2185                2190

Gly Thr Ile Thr Ala Gly Gln Asp Asp Ala Asn Phe Asp Ser Ile Arg
         2195                2200                2205

Ile Asp Ala Val Asp Phe Ile His Asn Asp Thr Ile Gln Arg Thr Tyr
         2210                2215                2220

Asp Tyr Leu Arg Asp Ala Tyr Gln Val Gln Gln Ser Glu Ala Lys Ala
2225                2230                2235                2240

Asn Gln His Ile Ser Leu Val Glu Ala Gly Leu Asp Ala Gly Thr Ser
             2245                2250                2255

Thr Ile His Asn Asp Ala Leu Ile Glu Ser Asn Leu Arg Glu Ala Ala
         2260                2265                2270

Thr Leu Ser Leu Thr Asn Glu Pro Gly Lys Asn Lys Pro Leu Thr Asn
         2275                2280                2285

Met Leu Gln Asp Val Asp Gly Gly Thr Leu Ile Thr Asp His Thr Gln
         2290                2295                2300

Asn Ser Thr Glu Asn Gln Ala Thr Pro Asn Tyr Ser Ile Ile His Ala
2305                2310                2315                2320

His Asp Lys Gly Val Gln Glu Lys Val Gly Ala Ala Ile Thr Asp Ala
             2325                2330                2335

Thr Gly Ala Asp Trp Thr Asn Phe Thr Asp Glu Gln Leu Lys Ala Gly
             2340                2345                2350

Leu Glu Leu Phe Tyr Lys Asp Gln Arg Ala Thr Asn Lys Lys Tyr Asn
         2355                2360                2365

Ser Tyr Asn Ile Pro Ser Ile Tyr Ala Leu Met Leu Thr Asn Lys Asp
         2370                2375                2380

Thr Val Pro Arg Met Tyr Tyr Gly Asp Met Tyr Gln Asp Asp Gly Gln
2385                2390                2395                2400

Tyr Met Ala Asn Lys Ser Ile Tyr Tyr Asp Ala Leu Val Ser Leu Met
             2405                2410                2415

Thr Ala Arg Lys Ser Tyr Val Ser Gly Gly Gln Thr Met Ser Val Asp
             2420                2425                2430

Asn His Gly Leu Leu Lys Ser Val Arg Phe Gly Lys Asp Ala Met Thr
         2435                2440                2445

Ala Asn Asp Leu Gly Thr Ser Ala Thr Arg Thr Glu Gly Leu Gly Val
2450                2455                2460

Ile Ile Gly Asn Asp Pro Lys Leu Gln Leu Asn Asp Ser Asp Lys Val
```

```
                2465                2470                2475                2480
        Thr Leu Asp Met Gly Ala Ala His Lys Asn Gln Lys Tyr Arg Ala Val
                    2485                2490                2495

Ile Leu Thr Thr Arg Asp Gly Leu Ala Thr Phe Asn Ser Asp Gln Ala
                2500                2505                2510

Pro Thr Ala Trp Thr Asn Asp Gln Gly Thr Leu Thr Phe Ser Asn Gln
                2515                2520                2525

Glu Ile Asn Gly Gln Asp Asn Thr Gln Ile Arg Gly Val Ala Asn Pro
                2530                2535                2540

Gln Val Ser Gly Tyr Leu Ala Val Trp Val Pro Val Gly Ala Ser Asp
        2545                2550                2555                2560

Asn Gln Asp Ala Arg Thr Ala Ala Thr Thr Thr Glu Asn His Asp Gly
                    2565                2570                2575

Lys Val Leu His Ser Asn Ala Ala Leu Asp Ser Asn Leu Ile Tyr Glu
                    2580                2585                2590

Gly Phe Ser Asn Phe Gln Pro Lys Ala Thr Thr His Asp Glu Leu Thr
                    2595                2600                2605

Asn Val Val Ile Ala Lys Asn Ala Asp Val Phe Asn Asn Trp Gly Ile
                2610                2615                2620

Thr Ser Phe Glu Met Ala Pro Gln Tyr Arg Ser Ser Gly Asp His Thr
        2625                2630                2635                2640

Phe Leu Asp Ser Thr Ile Asp Asn Gly Tyr Ala Phe Thr Asp Arg Tyr
                    2645                2650                2655

Asp Leu Gly Phe Asn Thr Pro Thr Lys Tyr Gly Thr Asp Gly Asp Leu
                    2660                2665                2670

Arg Ala Thr Ile Gln Ala Leu His His Ala Asn Met Gln Val Met Ala
                    2675                2680                2685

Asp Val Val Asp Asn Gln Val Tyr Asn Leu Pro Gly Lys Glu Val Val
                    2690                2695                2700

Ser Ala Thr Arg Ala Gly Val Tyr Gly Asn Asp Asp Ala Thr Gly Phe
        2705                2710                2715                2720

Gly Thr Gln Leu Tyr Val Thr Asn Ser Val Gly Gly Gln Tyr Gln
                    2725                2730                2735

Glu Lys Tyr Ala Gly Gln Tyr Leu Glu Ala Leu Lys Ala Lys Tyr Pro
                    2740                2745                2750

Asp Leu Phe Glu Gly Lys Ala Tyr Asp Tyr Trp Tyr Lys Asn Tyr Ala
                    2755                2760                2765

Asn Asp Gly Ser Asn Pro Tyr Tyr Thr Leu Ser His Gly Asp Arg Glu
                    2770                2775                2780

Ser Ile Pro Ala Asp Val Ala Ile Lys Gln Trp Ser Ala Lys Tyr Met
        2785                2790                2795                2800

Asn Gly Thr Asn Val Leu Gly Asn Gly Met Gly Tyr Val Leu Lys Asp
                    2805                2810                2815

Trp His Asn Gly Gln Tyr Phe Lys Leu Asp Gly Asp Lys Ser Thr Leu
                    2820                2825                2830

Pro Gln Ile
                2835

<210> SEQ ID NO 18
<211> LENGTH: 1888
<212> TYPE: PRT
<213> ORGANISM: Leuconostoc citreum

<400> SEQUENCE: 18
```

```
Met Glu Met Lys Glu Thr Ile Thr Arg Lys Lys Leu Tyr Lys Ser Gly
 1               5                  10                  15
Lys Ser Trp Val Ala Ala Thr Ala Phe Ala Val Met Gly Val Ser
             20                  25                  30
Ala Val Thr Thr Val Ser Ala Asp Thr Gln Thr Pro Val Gly Thr Thr
                 35                  40                  45
Gln Ser Gln Gln Asp Leu Thr Gly Gln Thr Gly Gln Asp Lys Pro Thr
     50                  55                  60
Thr Lys Glu Val Ile Asp Lys Lys Glu Pro Val Pro Gln Val Ser Ala
 65                  70                  75                  80
Gln Asn Val Gly Asp Leu Ser Ala Asp Ala Lys Thr Pro Lys Ala Asp
                 85                  90                  95
Asp Lys Gln Asp Thr Gln Pro Thr Asn Ala Gln Leu Pro Asp Gln Gly
             100                 105                 110
Asn Lys Gln Thr Asn Ser Asn Ser Asp Lys Gly Val Lys Glu Ser Thr
         115                 120                 125
Thr Ala Pro Val Lys Thr Thr Asp Val Pro Ser Lys Ser Val Ala Pro
 130                 135                 140
Glu Thr Asn Thr Ser Ile Asn Gly Gly Gln Tyr Val Glu Lys Asp Gly
145                 150                 155                 160
Gln Phe Val Tyr Ile Asp Gln Ser Gly Lys Gln Val Ser Gly Leu Gln
                 165                 170                 175
Asn Ile Glu Gly His Thr Gln Tyr Phe Asp Pro Lys Thr Gly Tyr Gln
             180                 185                 190
Thr Lys Gly Glu Leu Lys Asn Ile Asp Asp Asn Ala Tyr Tyr Phe Asp
         195                 200                 205
Lys Asn Ser Gly Asn Gly Arg Thr Phe Thr Lys Ile Ser Asn Gly Ser
 210                 215                 220
Tyr Ser Glu Lys Asp Gly Met Trp Gln Tyr Val Asp Ser His Asp Lys
225                 230                 235                 240
Gln Pro Val Lys Gly Leu Tyr Asp Val Glu Gly Asn Leu Gln Tyr Phe
                 245                 250                 255
Asp Leu Ser Thr Gly Asn Gln Ala Lys His Gln Ile Arg Ser Val Asp
             260                 265                 270
Gly Val Thr Tyr Tyr Phe Asp Ala Asp Ser Gly Asn Ala Thr Ala Phe
         275                 280                 285
Lys Ala Val Thr Asn Gly Arg Tyr Ala Glu Gln Thr Thr Lys Asp Lys
 290                 295                 300
Asp Gly Asn Glu Thr Ser Tyr Trp Ala Tyr Leu Asp Asn Gln Gly Asn
305                 310                 315                 320
Ala Ile Lys Gly Leu Asn Asp Val Asn Gly Glu Ile Gln Tyr Phe Asp
                 325                 330                 335
Glu His Thr Gly Glu Gln Leu Lys Gly His Thr Ala Thr Val Asp Gly
             340                 345                 350
Thr Thr Tyr Tyr Phe Glu Gly Asn Lys Gly Asn Leu Val Ser Val Val
         355                 360                 365
Asn Thr Ala Pro Thr Gly Gln Tyr Lys Ile Asn Gly Asp Asn Val Tyr
 370                 375                 380
Tyr Leu Asp Asn Asn Glu Ala Ile Lys Gly Leu Tyr Gly Ile Asn
385                 390                 395                 400
Gly Asn Leu Asn Tyr Phe Asp Leu Ala Thr Gly Ile Gln Leu Lys Gly
                 405                 410                 415
Gln Ala Lys Asn Ile Asp Gly Ile Gly Tyr Tyr Phe Asp Gln Asn Asn
```

```
                420             425             430
Gly Asn Gly Glu Tyr Arg Tyr Ser Leu Thr Gly Pro Val Val Lys Asp
            435                 440             445

Val Tyr Ser Gln His Asn Ala Val Asn Asn Leu Ser Ala Asn Asn Phe
450                 455                 460

Lys Asn Leu Val Asp Gly Phe Leu Thr Ala Glu Thr Trp Tyr Arg Pro
465                 470                 475                 480

Ala Gln Ile Leu Ser His Gly Thr Asp Trp Val Ala Ser Thr Asp Lys
            485                 490                 495

Asp Phe Arg Pro Leu Ile Thr Val Trp Trp Pro Asn Lys Asp Ile Gln
                500                 505             510

Val Asn Tyr Leu Lys Leu Met Gln Gln Ile Gly Ile Leu Asp Asn Ser
            515                 520                 525

Val Val Phe Asp Thr Asn Asn Asp Gln Leu Val Leu Asn Lys Gly Ala
            530                 535                 540

Glu Ser Ala Gln Ile Gly Ile Glu Lys Lys Val Ser Glu Thr Gly Asn
545                 550                 555                 560

Thr Asp Trp Leu Asn Glu Leu Leu Phe Ala Pro Asn Gly Asn Gln Pro
                565                 570                 575

Ser Phe Ile Lys Gln Gln Tyr Leu Trp Asn Val Asp Ser Glu Tyr Pro
                580                 585                 590

Gly Gly Trp Phe Gln Gly Gly Tyr Leu Ala Tyr Gln Asn Ser Asp Leu
            595                 600                 605

Thr Pro Tyr Ala Asn Thr Asn Pro Asp Tyr Arg Thr His Asn Gly Leu
            610                 615                 620

Glu Phe Leu Leu Ala Asn Asp Val Asp Asn Ser Asn Pro Val Val Gln
625                 630                 635                 640

Ala Glu Gln Leu Asn Trp Leu Tyr Tyr Leu Met Asn Phe Gly Gln Ile
                645                 650                 655

Thr Ala Asn Asp Ser Asn Ala Asn Phe Asp Ser Met Arg Ile Asp Ala
            660                 665                 670

Ile Ser Phe Val Asp Pro Gln Ile Ala Lys Lys Ala Tyr Asp Leu Leu
            675                 680                 685

Asp Lys Met Tyr Gly Leu Thr Asp Asn Glu Ala Val Ala Asn Gln His
            690                 695                 700

Ile Ser Ile Val Glu Ala Pro Lys Gly Glu Thr Pro Ile Thr Val Glu
705                 710                 715                 720

Lys Gln Ser Ala Leu Val Glu Ser Asn Trp Arg Asp Arg Met Lys Gln
                725                 730                 735

Ser Leu Ser Lys Asn Ala Thr Leu Asp Lys Leu Asp Pro Asp Pro Ala
                740                 745                 750

Ile Asn Ser Leu Glu Lys Leu Val Ala Asp Asp Leu Val Asn Arg Ser
            755                 760                 765

Gln Ser Ser Asp Lys Asp Ser Ser Thr Ile Pro Asn Tyr Ser Ile Val
            770                 775                 780

His Ala His Asp Lys Asp Ile Gln Asp Thr Val Ile His Ile Met Lys
785                 790                 795                 800

Ile Val Asn Asn Asn Pro Asn Ile Ser Met Ser Asp Phe Thr Met Gln
                805                 810                 815

Gln Leu Gln Asn Gly Leu Lys Ala Phe Tyr Glu Asp Gln His Gln Ser
                820                 825                 830

Val Lys Lys Tyr Asn Gln Tyr Asn Ile Pro Ser Ala Tyr Ala Leu Leu
            835                 840                 845
```

```
Leu Thr Asn Lys Asp Thr Val Pro Arg Val Phe Tyr Gly Asp Met Tyr
    850                 855                 860

Gln Asp Tyr Gly Asp Asp Leu Asp Gly Gly Gln Tyr Met Ala Thr Lys
865                 870                 875                 880

Ser Ile Tyr Tyr Asn Ala Ile Glu Gln Met Met Lys Ala Arg Leu Lys
                885                 890                 895

Tyr Val Ala Gly Gly Gln Ile Met Ala Val Thr Lys Ile Lys Asn Asp
                900                 905                 910

Gly Ile Asn Lys Asp Gly Thr Asn Lys Ser Gly Glu Val Leu Thr Ser
            915                 920                 925

Val Arg Phe Gly Lys Asp Ile Met Asp Ala Gln Gly Gln Gly Thr Ala
    930                 935                 940

Glu Ser Arg Asn Gln Gly Ile Gly Val Ile Val Ser Asn Ser Ser Gly
945                 950                 955                 960

Leu Glu Leu Lys Asn Ser Asp Ser Ile Thr Leu His Met Gly Ile Ala
                965                 970                 975

His Lys Asn Gln Ala Tyr Arg Ala Leu Met Leu Thr Asn Asp Lys Gly
                980                 985                 990

Ile Val Asn Tyr Asp Gln Asp Asn Asn Ala Pro Ile Ala Trp Thr Asn
                995                 1000                1005

Asp His Gly Asp Leu Ile Phe Thr Asn Gln Met Ile Asn Gly Gln Ser
    1010                1015                1020

Asp Thr Ala Val Lys Gly Tyr Leu Asn Pro Glu Val Ala Gly Tyr Leu
1025                1030                1035                1040

Ala Val Trp Val Pro Val Gly Ala Asn Asp Asn Gln Asp Ala Arg Thr
                1045                1050                1055

Val Thr Thr Asn Gln Lys Asn Thr Asp Gly Lys Val Leu His Thr Asn
                1060                1065                1070

Ala Ala Leu Asp Ser Lys Leu Met Tyr Glu Gly Phe Ser Asn Phe Gln
                1075                1080                1085

Lys Met Pro Thr Arg Gly Asn Gln Tyr Ala Asn Val Val Ile Thr Lys
                1090                1095                1100

Asn Ile Asp Leu Phe Lys Ser Trp Gly Ile Thr Asp Phe Glu Leu Ala
1105                1110                1115                1120

Pro Gln Tyr Arg Ser Ser Asp Gly Lys Asp Ile Thr Asp Arg Phe Leu
                1125                1130                1135

Asp Ser Ile Val Gln Asn Gly Tyr Gly Leu Ser Asp Arg Tyr Asp Leu
                1140                1145                1150

Gly Phe Lys Thr Pro Thr Lys Tyr Gly Thr Asp Gln Asp Leu Arg Lys
                1155                1160                1165

Ala Ile Glu Arg Leu His Gln Ala Gly Met Ser Val Met Ala Asp Phe
    1170                1175                1180

Val Ala Asn Gln Ile Tyr Gly Leu His Ala Asp Lys Glu Val Val Ser
1185                1190                1195                1200

Ala Gln His Val Asn Ile Asn Gly Asp Thr Lys Leu Val Val Asp Pro
                1205                1210                1215

Arg Tyr Gly Thr Gln Met Thr Val Val Asn Ser Val Gly Gly Gly Asp
                1220                1225                1230

Tyr Gln Ala Lys Tyr Gly Gly Glu Tyr Leu Asp Thr Ile Ser Lys Leu
            1235                1240                1245

Tyr Pro Gly Leu Leu Leu Asp Ser Asn Gly Gln Lys Ile Asp Leu Ser
            1250                1255                1260
```

```
Thr Lys Ile Lys Glu Trp Ser Ala Lys Tyr Leu Asn Gly Ser Asn Ile
1265                1270                1275                1280

Pro Gln Val Gly Met Gly Tyr Val Leu Lys Asp Trp Asn Asn Gly Gln
            1285                1290                1295

Tyr Phe His Ile Leu Asp Lys Glu Gly Gln Tyr Ser Leu Pro Thr Gln
            1300                1305                1310

Leu Val Ser Asn Asp Pro Glu Thr Gln Ile Gly Glu Ser Val Asn Tyr
            1315                1320                1325

Lys Tyr Phe Ile Gly Asn Ser Asp Ala Thr Tyr Asn Met Tyr His Asn
            1330                1335                1340

Leu Pro Asn Thr Val Ser Leu Ile Asn Ser Gln Glu Gly Gln Ile Lys
1345                1350                1355                1360

Thr Gln Gln Ser Gly Val Thr Ser Asp Tyr Glu Gly Gln Gln Val Gln
            1365                1370                1375

Val Thr Arg Gln Tyr Thr Asp Ser Lys Gly Val Ser Trp Asn Leu Ile
            1380                1385                1390

Thr Phe Ala Gly Gly Asp Leu Gln Gly Gln Lys Leu Trp Val Asp Ser
            1395                1400                1405

Arg Ala Leu Thr Met Thr Pro Phe Lys Thr Met Asn Gln Ile Ser Phe
            1410                1415                1420

Ile Ser Tyr Ala Asn Arg Asn Asp Gly Leu Phe Leu Asn Ala Pro Tyr
1425                1430                1435                1440

Gln Val Lys Gly Tyr Gln Leu Ala Gly Met Ser Asn Gln Tyr Lys Gly
            1445                1450                1455

Gln Gln Val Thr Ile Ala Gly Val Ala Asn Val Ser Gly Lys Asp Trp
            1460                1465                1470

Ser Leu Ile Ser Phe Asn Gly Thr Gln Tyr Trp Ile Asp Ser Gln Ala
            1475                1480                1485

Leu Asn Thr Asn Phe Thr His Asp Met Asn Gln Lys Val Phe Val Asn
            1490                1495                1500

Thr Thr Ser Asn Leu Asp Gly Leu Phe Leu Asn Ala Pro Tyr Arg Gln
1505                1510                1515                1520

Pro Gly Tyr Lys Leu Ala Gly Leu Ala Lys Asn Tyr Asn Asn Gln Thr
            1525                1530                1535

Val Thr Val Ser Gln Gln Tyr Phe Asp Asp Gln Gly Thr Val Trp Ser
            1540                1545                1550

Gln Val Val Leu Gly Gly Gln Thr Val Trp Val Asp Asn His Ala Leu
            1555                1560                1565

Ala Gln Met Gln Val Ser Asp Thr Ser Gln Gln Leu Tyr Val Asn Ser
1570                1575                1580

Asn Gly Arg Asn Asp Gly Leu Phe Leu Asn Ala Pro Tyr Arg Gly Gln
1585                1590                1595                1600

Gly Ser Gln Leu Ile Gly Met Thr Ala Asp Tyr Asn Gly Gln His Val
            1605                1610                1615

Gln Val Thr Lys Gln Gly Gln Asp Ala Tyr Gly Ala Gln Trp Arg Leu
            1620                1625                1630

Ile Thr Leu Asn Asn Gln Gln Val Trp Val Asp Ser Arg Ala Leu Ser
            1635                1640                1645

Thr Thr Ile Val Gln Ala Met Asn Asp Asp Met Tyr Val Asn Ser Asn
            1650                1655                1660

Gln Arg Thr Asp Gly Leu Trp Leu Asn Ala Pro Tyr Thr Met Ser Gly
1665                1670                1675                1680

Ala Lys Trp Ala Gly Asp Thr Arg Leu Ala Asn Gly Arg Tyr Val His
```

-continued

```
                1685                1690                1695
Ile Ser Lys Ala Tyr Ser Asn Glu Val Gly Asn Thr Tyr Tyr Leu Thr
            1700                1705                1710

Asn Leu Asn Gly Gln Ser Thr Trp Ile Asp Lys Arg Ala Phe Thr Ala
            1715                1720                1725

Thr Phe Asp Gln Val Val Ala Leu Asn Ala Thr Ile Val Ala Arg Gln
            1730                1735                1740

Arg Pro Asp Gly Met Phe Lys Thr Ala Pro Tyr Gly Glu Ala Gly Ala
1745                1750                1755                1760

Gln Phe Val Asp Tyr Val Thr Asn Tyr Asn Gln Gln Thr Val Pro Val
            1765                1770                1775

Thr Lys Gln His Ser Asp Ala Gln Gly Asn Gln Trp Tyr Leu Ala Thr
            1780                1785                1790

Val Asn Gly Thr Gln Tyr Trp Ile Asp Gln Arg Ser Phe Ser Pro Val
            1795                1800                1805

Val Thr Lys Ala Val Asp Tyr Gln Ala Lys Ile Val Pro Arg Thr Thr
            1810                1815                1820

Arg Asp Gly Val Phe Ser Gly Ala Pro Tyr Gly Glu Val Asn Ala Lys
1825                1830                1835                1840

Leu Val Asn Met Ala Thr Ala Tyr Gln Asn Gln Val Val His Ala Thr
            1845                1850                1855

Gly Glu Tyr Thr Asn Ala Ser Gly Ile Thr Trp Ser Gln Phe Ala Leu
            1860                1865                1870

Ser Gly Gln Glu Asp Lys Leu Trp Ile Asp Lys Arg Ala Leu Gln Ala
            1875                1880                1885

<210> SEQ ID NO 19
<211> LENGTH: 1244
<212> TYPE: PRT
<213> ORGANISM: Lactobacillus reuteri
<220> FEATURE:
<223> OTHER INFORMATION: CNCM I-2451

<400> SEQUENCE: 19

Ile Pro Asp Thr Asn Val Gln Gly Asn Thr Asn Trp Tyr Phe Val Lys
1               5                   10                  15

Asp Gly Ile Ala Gln Ser Gly Val Gln Gln Trp Ala Gly Ser Tyr Tyr
            20                  25                  30

Tyr Phe Asp Pro Val Thr Tyr Leu Arg Val Asp Asn Arg Tyr Val Gln
        35                  40                  45

Ser Gln Trp Gly Leu Lys Tyr Met Phe Gly Lys Asp Gly Arg Ile Ala
    50                  55                  60

Thr Gly Leu Tyr Lys Trp Asp Lys Asn Asn Gln Trp Tyr Tyr Phe Asn
65                  70                  75                  80

Pro Ile Thr Tyr Leu Ala Val Thr Asn Asp Tyr Ile Gln Ala Asn Asp
                85                  90                  95

Gly Asn Trp Tyr Leu Phe Thr Ala Asp Gly Thr Ala Ala Ser Arg Val
            100                 105                 110

Ala Gln Trp Ala Gly Thr Tyr Tyr Phe Asp Pro Val Thr His Leu
        115                 120                 125

Arg Val Asp Asn Asn Tyr Val Gln Ser Gln Trp Gly Asp Trp Tyr Leu
    130                 135                 140

Phe Gly Asn Asp Gly Arg Ile Leu Ser Gly Val Gln Gln Trp Ala Gly
145                 150                 155                 160

Thr Tyr Tyr Tyr Phe Asp Pro Thr Thr Tyr Leu Arg Val Asp Asp Asp
```

```
            165                 170                 175
Tyr Val Thr Ser Gln Trp Gly Leu Lys Tyr Met Phe Gly Lys Asp Gly
            180                 185                 190

Arg Ile Ala Thr Gly Leu Tyr Lys Trp Asp Lys Asn Gln Trp Tyr
            195                 200             205

Tyr Phe Asp Pro Thr Thr Tyr Leu Ala Val Thr Asn Asn Tyr Ile Gln
210                 215                 220

Ala Asn Asp Gly His Trp Tyr Leu Phe Thr Ala Asp Gly Thr Ala Ala
225                 230                 235                 240

Ser Arg Val Ala Lys Trp Ala Gly Thr Tyr Tyr Phe Asp Pro Val
            245                 250                 255

Thr His Leu Arg Val Asp Asn Tyr Val Gln Ser Gln Trp Gly Asp
            260                 265                 270

Trp Tyr Met Phe Gly Asn Asp Gly Arg Ile Ile Thr Gly Arg Thr Leu
            275                 280                 285

Trp Tyr Gly Asn Tyr Tyr Phe Asp Pro Val Thr Tyr Leu Lys Val
            290                 295                 300

Thr Asn Lys Trp Val Asp Gly Asn Tyr Asp Glu Asp Gly Ala Gln
305                 310                 315                 320

Ala Ile Ser Lys Leu Val Thr Ile Asn Asn Arg Leu Tyr Tyr Phe Asp
                325                 330                 335

Asp Gln Gly Lys Glu Ile Ser Asn Gln Phe Arg Thr Ile Tyr Gly Asn
            340                 345                 350

Thr Tyr Tyr Phe Gly Asn Asp Ser Ala Ala Val Thr Gly Gln Gln Thr
            355                 360                 365

Ile Asp Gly Lys Val Tyr Asn Phe Ser Lys Tyr Gly His Leu Leu Gly
370                 375                 380

Asn Arg Tyr Gly Lys Ile Glu Asn Gly Lys Leu Asn Ile Tyr Ser Leu
385                 390                 395                 400

Ala Asp Asn Ser Leu Ile Lys Thr Val Glu Ala Gly Pro Trp Glu Asn
                405                 410                 415

Met Ala Tyr Ser Met Asp Ser Asn Ser Ile Asn Asn Ile Asp Gly Tyr
            420                 425                 430

Ile Ser Tyr Thr Gly Trp Tyr Arg Pro Tyr Gly Thr Ser Gln Asp Gly
            435                 440                 445

Lys Thr Trp Tyr Pro Thr Thr Val Ala Asp Trp Arg Pro Ile Leu Met
450                 455                 460

Tyr Val Trp Pro Ser Lys Asp Val Gln Ala Lys Phe Ile Gln Tyr Phe
465                 470                 475                 480

Val Asn His Gly Tyr Glu Asn Ser Asn Tyr Gly Leu Thr Thr Gly Ser
            485                 490                 495

Val Lys Asp Leu Ser Glu Asn Thr Ala Ser Ile Lys Leu Asn Glu Val
            500                 505                 510

Ala Gln Asn Leu Arg Tyr Val Ile Glu Gln His Ile Val Ala Ala Lys
            515                 520                 525

Ser Thr Ser Gln Leu Ala Asn Asp Ile Asn Asn Phe Ile Thr Thr Ile
            530                 535                 540

Pro Glu Leu Ser Ala Ser Ser Glu Leu Pro Tyr Gly Gln Val Ile Phe
545                 550                 555                 560

Val Asn Asn Asp Asn Thr Ser Tyr Ala Asp Ser Lys Tyr Arg Leu Met
                565                 570                 575

Ser Arg Thr Ile Asn Asn Gln Thr Gly Asn Asp Asn Asp Asn Ser Asp
            580                 585                 590
```

```
Asn Gly Tyr Glu Phe Leu Thr Gly Ile Asp Ile Asp Asn Ser Asn Pro
            595                 600                 605

Val Val Gln Ala Glu Asn Leu Asn Trp Glu Tyr Phe Leu Leu Asn Tyr
    610                 615                 620

Gly Lys Leu Met Gly Tyr Asn Pro Asp Gly Asn Phe Asp Gly Phe Arg
625                 630                 635                 640

Ile Asp Ala Ala Asp His Ile Asp Ala Asp Val Leu Asp Gln Thr Gly
                645                 650                 655

Gln Leu Met Asp Asp Met Tyr His Met Lys Gly Asn Pro Gln Asn Ala
                660                 665                 670

Asn Asn His Leu Ser Tyr Asn Glu Gly Tyr Arg Ser Ser Ala Ala Arg
            675                 680                 685

Met Leu Asn Lys Lys Gly Asn Pro Gln Leu Tyr Met Asp Tyr Val Gly
        690                 695                 700

Ser Thr Leu Gly Asn Val Leu Gly Arg Ala Asn Asn Arg Asp Thr Ile
705                 710                 715                 720

Ser Asn Leu Val Thr Gly Ser Ile Val Asn Arg Gln Asn Asp Val Thr
                725                 730                 735

Glu Asn Glu Ala Thr Pro Asn Trp Ser Tyr Val Thr Asn His Asp Ser
                740                 745                 750

Arg Ala Asn Leu Ile Asn Gly Leu Ile Ser Lys Asp His Pro Gly Ala
            755                 760                 765

Tyr Lys Ala Glu Tyr Ala Asn Gln Ala Trp Gln Glu Phe Tyr Ala Asp
        770                 775                 780

Gln Lys Lys Thr Asp Lys Gln Tyr Ala Gln Tyr Asn Val Pro Ala Gln
785                 790                 795                 800

Tyr Ala Ile Leu Leu Ser Asn Lys Asp Thr Val Pro Gln Ile Tyr Tyr
                805                 810                 815

Gly Asp Leu Tyr Asn Glu Thr Ala Gln Tyr Met Gln Glu Lys Ser Ile
                820                 825                 830

Tyr Tyr Asp Ala Ile Thr Thr Leu Met Lys Ala Arg Lys Gln Phe Val
            835                 840                 845

Ser Gly Gly Gln Thr Met Thr Lys Leu Ser Asp Asn Leu Ile Ala Ser
        850                 855                 860

Val Arg Tyr Gly Lys Gly Val Thr Asn Ala Asn Ser Glu Gly Thr Asp
865                 870                 875                 880

Ser Leu Ser Arg Thr Ser Gly Met Ala Val Ile Val Gly Asn Asn Pro
                885                 890                 895

Gln Met Ala Glu Gln Thr Ile Ser Ile Asn Met Gly Arg Ala His Ala
                900                 905                 910

Asn Glu Gln Tyr Arg Asn Leu Leu Asp Thr Thr Asp Asn Gly Leu Thr
            915                 920                 925

Tyr Asn Ala Asp Gly Ala Glu Asn Pro Glu Thr Leu Thr Thr Asp Asp
        930                 935                 940

Asn Gly Ile Leu Lys Val Thr Val Lys Gly Tyr Ser Asn Pro Tyr Val
945                 950                 955                 960

Ser Gly Tyr Leu Gly Val Trp Val Pro Val Val Ser Gly Asn Gln Asp
                965                 970                 975

Val Thr Thr Asn Ala Ala Thr Val Ser Ala Asp Ser Asn Lys Ile Phe
            980                 985                 990

Glu Ser Asn Ala Ala Leu Asp Ser His Met Ile Tyr Gln Asp Phe Ser
        995                 1000                1005
```

-continued

```
Leu Tyr Gln Pro Glu Pro Thr Ser Thr Glu Asn His Ala Tyr Asn Thr
        1010                1015                1020

Ile Ala Gln Asn Ala Glu Leu Phe Asn Asn Leu Gly Ile Thr Asp Phe
1025                1030                1035                1040

Trp Met Ala Pro Pro Tyr Thr Gln Tyr Ser Glu Ser Arg Tyr Asn Asp
                1045                1050                1055

Gly Tyr Ser Val Thr Asp Arg Tyr Asn Leu Gly Thr Asn Ala Asn Pro
            1060                1065                1070

Thr Lys Tyr Gly Ser Gly Glu Leu Ala Asn Ala Ile Ala Ala Leu
            1075                1080                1085

His Ser Ala Gly Leu Lys Val Gln Val Asp Ile Val Met Asn Gln Met
    1090                1095                1100

Ile Gly Leu Pro Gly Gln Glu Ala Val Thr Val Thr Arg Ala Asp Asn
1105                1110                1115                1120

Arg Gly Ile Gln Thr Tyr Val Asn Gly Lys Thr Tyr Ala Asn Gln Met
                1125                1130                1135

Tyr Phe Ala Tyr Thr Thr Gly Gly Gly Asn Gly Gln Glu Thr Tyr Gly
            1140                1145                1150

Gly Lys Tyr Leu Ser Glu Leu Gln Ser Lys Tyr Pro Asp Leu Phe Thr
            1155                1160                1165

Thr Arg Ala Ile Ser Thr Gly Val Ala Pro Asp Pro Thr Thr Arg Ile
        1170                1175                1180

Thr Lys Trp Ser Ala Lys Tyr Glu Asn Gly Thr Ser Leu Gln Asn Ile
1185                1190                1195                1200

Gly Ile Gly Leu Ala Val Lys Leu Pro Asn Gly Glu Tyr Ala Tyr Leu
            1205                1210                1215

Arg Ser Ser Asp Asn Lys Ala Phe Asn Thr Thr Leu Pro Glu Thr Met
            1220                1225                1230

Ser Ser Ala Asp Tyr Tyr Ala Asn Ile Glu Asp Asp
        1235                1240
```